United States Patent
Georges et al.

(10) Patent No.: US 10,174,374 B2
(45) Date of Patent: Jan. 8, 2019

(54) DETECTING THE BRACHYSPINA MUTATION

(75) Inventors: Michel Georges, Villers-aux-Tours (BE); Wouter Coppieters, Landen (BE); Carole Charlier, Sprimont (BE); Jørgen Steen Agerholm, Hvidovre (DK); Merete Fredholm, Lyngby (DK); Peter Karlskov-Mortensen, Hilleroed (DK)

(73) Assignees: Universite de Liege, Angleur (BE); University of Copenhagen, Copenhagen K (DK)

( * ) Notice: Subject to any disclaimer, the term of this patent is extended or adjusted under 35 U.S.C. 154(b) by 1006 days.

(21) Appl. No.: 14/117,195

(22) PCT Filed: Sep. 22, 2011

(86) PCT No.: PCT/EP2011/066524
§ 371 (c)(1),
(2), (4) Date: Apr. 9, 2015

(87) PCT Pub. No.: WO2012/155995
PCT Pub. Date: Nov. 22, 2012

(65) Prior Publication Data
US 2015/0247195 A1    Sep. 3, 2015

Related U.S. Application Data

(60) Provisional application No. 61/485,915, filed on May 13, 2011.

(51) Int. Cl.
*C12Q 1/68* (2018.01)
*C12P 19/34* (2006.01)
*C12Q 1/6883* (2018.01)
*C07H 21/04* (2006.01)

(52) U.S. Cl.
CPC ...... *C12Q 1/6883* (2013.01); *C12Q 2600/118* (2013.01); *C12Q 2600/124* (2013.01); *C12Q 2600/156* (2013.01)

(58) Field of Classification Search
CPC ............ C12Q 1/6883; C12Q 2600/118; C12Q 2600/124; C12Q 2600/156
See application file for complete search history.

(56) References Cited

FOREIGN PATENT DOCUMENTS

WO    WO-2010/012690    2/2010

OTHER PUBLICATIONS

Agerholm, et al. "Familial occurrence of Danish and Dutch cases of the bovine brachyspina syndrome", BMC Veterinary Research (2007), vol. 3, No. 8, pp. 1-6.
Database Geneseq [Online] Feb. 15, 2008 (Feb. 15, 2008), "Bos taurus breed Hereford Ctg75.CH240-313J1, whole genome shotgun sequence", XP002668706, Database accession No. AAFC03040853.1.
Database Geneseq [Online] Jul. 18, 2010 (Jul. 18, 2010), "Bos taurus Fanconi anemia, complementation group I (FANCI), mRNA", XP002668705, accession No. NM_001191454.1.
Database Geneseq [Online] Jul. 30, 2008 (Jul. 30, 2008), "Bos taurus breed Hereford chromosome 21, alternate assembly Btau_4.6.1", XP002668707, Database accession No. NC_007319.5.
International Preliminary Report on Patentability & Written Opinion in PCT/EP2011/066524 dated Nov. 28, 2013.
International Search Report in PCT/EP2011/066524 dated Mar. 13, 2012.
Liu, et al. "Bos Taurus genome assembly", BMC Genomics (2009), vol. 10, No. 180, pp. 1-11.
Zimin, et al. "A whole-genome assembly of the domestic cow, *Bos taurus*", Genome Biology (2009), vol. 10, Issue 4, Article R42, pp. 1-10.

*Primary Examiner* — Stephen T Kapushoc
(74) *Attorney, Agent, or Firm* — Foley & Lardner LLP

(57) ABSTRACT

This invention relates to methods for the detection of a bovine that is affected by or carrier of brachyspina. It is based on the identification of a 3.3 Kb deletion in the bovine FANCI gene that is shown to cause the brachyspina syndrome. The present invention provides methods and uses for determining whether a bovine is affected by or carrier of brachyspina by analyzing its genomic DNA or its RNA. The methods can be used to perform marker assisted selection or genomic selection for increased fertility in said bovine.

16 Claims, 3 Drawing Sheets

Specification includes a Sequence Listing.

SEQUENCE LISTING

<160> NUMBER OF SEQ ID NOS: 13

<210> SEQ ID NO 1
<211> LENGTH: 65700
<212> TYPE: DNA
<213> ORGANISM: Bos taurus

<400> SEQUENCE: 1

| | | | | | |
|---|---|---|---|---|---|
| tcgctaaata | gtgaccaact | ctttgcaacc | ccatgaactg | cagtacatca | ggcttccctg | 60 |
| tctttcaata | tcttttggag | tttgctcaaa | ctcatgtcca | ttgagtcaga | gatgccatcc | 120 |
| aaccatctca | tcctctgtta | cccacttctt | ctcttgccct | caatctttcc | cagcatcagg | 180 |
| gtcttttcca | atgaatcggt | tctttgcaac | aggtggccaa | agtattggag | cttcagtatc | 240 |
| agtccttcca | atgaatgcag | gaatctaggt | tcatttaaat | tattccttag | atttgcattt | 300 |
| tcactatcta | aggatcggta | cattcaaaac | acagaacgtt | tcctgttttc | ccttcaggca | 360 |
| cactgagacc | ggagactgca | gggctacgga | cttgattcct | gaagtacagg | aattgcacgc | 420 |
| aacatttatt | tttcctttac | agggcaact | ggcacctctt | acggcacaag | ggagtaagga | 480 |
| gacttcctct | gccttccagg | catttcccat | gcaacaaagc | attactttga | ttcattggct | 540 |
| ctctcactga | cccttttcccc | aattgtacat | aggaaaggcc | ttaactgggt | caggacatcg | 600 |
| tggtgactat | gcccgggaca | cacttcccct | gctcattctg | aggtccccgaa | ttagcgtcag | 660 |
| agaatgtgtg | cccccccccc | cactttgaga | tgggaacgtt | cgagagaatc | gctccaagca | 720 |
| cgagctcccg | ggtaacggaa | ataagccgca | gggggcggga | cccgttgctc | agggtaacgg | 780 |
| aaggacggaa | acggcaggtt | gcgcgggttt | tttggaattc | agtggctgcg | ttgaagtgga | 840 |
| agtgaccggc | tagaggagct | tcgcgcgtcg | caggggagga | gggactcagc | tcccgggagg | 900 |
| taaggggtct | gggaggacag | gacggcgccc | cttccgaatg | gcgttctggc | ttttccttg | 960 |
| gcccgaaaga | gtctgtgccc | tggcgtctcc | cgttgtggcc | tttagcgttt | cctgctcctc | 1020 |
| gggcggccta | cacccttggc | cctctcgtta | aattcttcct | ctccatcagc | gttcagctcc | 1080 |
| tacgtctgag | acatttctct | aaacccgttt | cgcctttgta | gctcggtcac | agcgattatc | 1140 |
| cccagctgcc | ttgttttata | gtttctctgt | gtttacttct | cgctctccga | gaagcccggg | 1200 |
| tgctaaaccc | gcggcgtctc | cctttcgtgg | tgcctcacta | acctcagggc | ctttggacaa | 1260 |
| ggagtctgct | atccgcacag | ggacttaaca | gccaccatc | tgtgtgctac | tcaattctgg | 1320 |
| ttttaggact | aatttagcaa | atgtaccgtc | tgaaatagaa | ggagttcagc | atcttccctt | 1380 |
| tagggctgga | cgtttctttg | gttgatatcc | cttttctgaa | tcctctacca | ttcagcccct | 1440 |
| aatagaggg | ctaatcgtag | gtaagagtcc | ccagtagtac | gtaaaagcat | gggtttggg | 1500 |
| gtctggaatt | ggacagactt | aggtttcagt | tctacttctg | caacttacta | gccttctaac | 1560 |
| ctttggggga | cgttccttaa | tttctctgaa | tctcaaatga | tcttcatctg | aattgggagt | 1620 |
| aatagcacca | acctcagagg | actggtgtga | ggatcaatgt | cattttcccc | acaaatattt | 1680 |
| attgggcacc | tattacgagc | ttactgtgct | aagtcttgga | gattcagtga | taaaaccaga | 1740 |
| ggtggcccc | tgccctcttg | gagtttgtaa | tggagtggga | gatgtaattc | ttaatctaat | 1800 |
| aataagtgta | atgttaaaag | tgtggtgatg | gtgagagatt | acagttgcct | tgaaagaatg | 1860 |
| taataggga | gtgtttagac | tgagcttgta | aaggagtgtg | ggattgagct | gagacctgaa | 1920 |
| ggatttttag | gaattaacaa | taaaagatc | ggtgggcagg | ggatgaaaga | aggggtattt | 1980 |
| atttttatat | aagttccaga | cagaaaatca | tgtggaattg | actgtggcag | gaggaacttg | 2040 |
| ggggtttgaa | ggactgagca | gttcagtgta | gctggaatat | agagtgatga | aaaggaatta | 2100 |

```
acatggacca gccatgaaat taaaagacgc ttagtccttg aaggaaagt tatgtccaac     2160 ctagatagca tattcaaaac cagagacatt actttgccaa caaaggtctg tctagtcaac     2220
gctatggttt ttcctgtggt catgtatgga tgtgagagtt ggactgtgaa gaaggctgag     2280
cgccgaagaa ttgatgcttt tgaactgtgg tgttggagaa gactcttttt ctttttttg      2340 gactatgaat atgctttatt ggagaagcaa agaatagaca cgctaattgc tcatggggtc     2400
aagatcacag tgcagataca gacacacaga tggcaaagag agatcaagcg atgatcctgc     2460
tgctcttcca caacgtggt gtcagcttca ggaagcaagc cttttctctg ccagctgtca      2520
gtccaggagg gagattaagg aagatacaat ccatcaccat ggccaaaggg aggacaatgg     2580
gagagcctgg atcttgtttc ttggtccaga tgaaatctgg tgctgttact tccacttggg     2640
tggacacttc tgctcgcatg gtgggcatgg tggcccagga gggcatttct tctggcttag     2700
tggaggtggg catggatgag gtgggcaaga ctcatggcac ttgggtgggc acacttttgg    2760
aggtggatgg cagggctcct tgcactgatg gtgatgctga tgctgatgtt gatgcggatg    2820
cggatgggga tgcggatggt cagacatctt cctgggtctc aaggaatcaa atccaagctt    2880
gttccacttg ctgcagtgaa tctgagatga ggtgtctaga gtaggctgca ggcgtccttc    2940
cgttctcccg aaggagagga gacctggaga agactcttga gagtcccttg gactgcaagg    3000
agatccaacc agtccattct gaaggagatc agccctagga tttctttgga aggaatgatg    3060
ctaaagctga aattccagta ctttggctac ctcatgggaa gagttgactc attggaaaag    3120
actctgatgc tgggaggggt tgggggcagg aggaaaaggg gatgacagag gatgagatgg    3180
gctggatggc atcactgact cgatggacat gagtctgaat gaactccggg agttggtgat    3240
ggacagggag gcctggcgtg ctgcgattca tggggtcgca aagagtcggg acacgactga    3300
gcgactgaac caaaccttta tatcctgacg tcagggattt tggactaata atggaaagcc    3360
accgagtagt ttttaagatg aggatgaatc acaaatctgg tttgtgtttc aaagacattt    3420
tagctgctgg gtggggaatg agttaggaag ctgtgtagta gtttaggtga gagatgatgg    3480
tgactttgga ataatgtggc agtagtgaat ctcagaagta gacttgagag atgtttgggg    3540
acacaggact tggtagtgga tgtgaaggat gaaggtgaag tggttaagaa tgttgcccag    3600
gtttcttgtt tcagcagctg ggtggatgat ggtataattt agggagattg aaagcagcag    3660
gaaatacagg aggaggtttt cttttccacca gtctgcattg ccctcttctc gtaatactcc    3720
catagctact cactgctcac taaatcctat ctgcctaatg tgcttccatt tcacccttc      3780 ctttgcagtc tccagagtca ggccccaaca ccagcctttg tcactaccac taaaatagct     3840
cccagtagac tcttagcctc tgctcttctt ccttattccc tccctacttt aatctgcgca     3900 ttgatgcat atttagttc ctcaaacact gtttcagtct tgtcagattc tcttttactc       3960
cagaactttt tgtcactatt acttacagaa taaggcctaa cttccttaat tcgacatttg     4020
agatcttgca cagcttagcc cctccctttt actagccttc cttctcactg ctcccctagt     4080
tgaactctct acctcaggct acgtactcat ttttcccgag taagttttc acattctctt      4140 atgaatgcct tgttgacag taccttcctc cccagtaatg tacaccatgt ggttctggtg      4200
actatctaca tttaatcttt aaattccagt tcaaggtttc ctttgctagg aagcctgctt     4260
gatgtttgag cacacttta tttcttagcc ttgttaactt ctcatttatt tttgtaccgt      4320
ttaattggta taaatgtgtt tacagtgcta ttgctttatt catttattgt gtatgtgtag     4380
ataatagtat atatttgcaa tactgttaaa tgacagcttt gttctaggta gcataatggg     4440
```

```
tagatactta aaaaaaaaaa aagaaaatgt gaacaattga attatgagac gacttaattt   4500
gactacagct ttctaataag gaaattccag gggattctcc agattctttg gtttggttaa   4560
gaatcaccta ctcctacagt tggtagtcct tagcctgttg agtattcatt gtgtacataa   4620
catatttgaa atactcagtt aacaagtaga aagggaaaa aatcaaactt gtttactttt    4680
gggagtttta tccagctctt gacattttc cttttcagtt ccttgtttgt gcaacaatgg    4740
accagaaaat tttatctcta gcagcagaaa aaacagcaga tggcctacag gaatttcttc   4800
aaatcctgaa agaagatgat gtgagtattg ggaagcaagt tctgccaaaa gtagatgcca   4860
ggcatgatga gagatgtaag ggacatgtta gaattaattc tgccgcttca tctatccccc   4920
actcacctta ggagacaagg gtttatttga taacaactca tagatgtaac agaggaggca   4980
atggcacccc actccagtac ttttgcctgg aaaatcccat ggacggagga gtctggtagg   5040
ctgcagtcca tggggtcgct agagttggac acgactgatc gacttcactt tcactttcct   5100
gcattgagaa aggaaatggc aacccactcc agtgttcttc cctggagaat cccagggaca   5160
gggaagcctg gtgggctgct gtctctgggg tcgcacagag tcgacacga ctgaagtgac    5220 ttaggagcag cagcagcagc acagatgtaa agaaatgggg gagaggaaga gatatggact   5280
acttaagggc atttggagaa ggcaatggca ccccactcca gtactcttgc ctggaaaatt   5340
ccatggatgg aggagcctgg tgggctgcag tccatggggt cgctaagagt cggagacaac   5400
tgagtgactt cactttcact tttcactttc ctgcagtgaa gaaggaaatg gcaacccact   5460
ccgctattct tgcctggaga atcccaggga cggcggagcc tggtgggctg ctgtctatgg   5520
ggtcgcacag agtcggacat gactgaagtg gcttagcagt aagggcattt gtgtacattt   5580
atacaactat aatttcttgg gaacatacag tttaatgaaa tcaacccaat ttgagatgga   5640
gtgcttaaac agatcaattt tcataaaaga aaaaagtta gcagttatac ttcaacaaaa    5700
ataccaggcc cagatagttt ttcaggaggc ttctaccaaa cctttagaaa tcagaggtaa   5760
gatctagata gtcccagtgc tacacaagtt gttttagagc acacatatta cgtaatgtat   5820
gtatatacat aaggaaagct tcctgataaa gacagcttga aggggcttcc attggtgaaa   5880
tgtgaacatc aaaataatca agttcagtta tgaattataa accactgaaa tataaagaaa   5940
tctgtgagtc catattgata aaaaaaaaat aaatggtggg aaaggttctt gcttaccata   6000
aagttagaaa atcgtcattt ggcaacagtc atgatcaaga ttggatcagg cagaagcagc   6060
agtggatgct aaatccaggg agcagttttt tgaactttt atttttgaatt gattttagat    6120 ttacagaaaa gttgtaaaaa tagtagagtt tctgtatagt tctctcccca gtgttaacat   6180
cttacgtaat aatttcagta aaattttaca agccaggaag ttaatatttg tacagtacct   6240
ttagtgagac taaagagtat ttgaacccta cctggtagtt ttttcactga tacccgtttt   6300
ttttttatgt tccagaatcc cactcaggat cctacactgc acttaattgt tatttcccc    6360 tgattttctg caatcagcaa ctgctcctca gtctttctct gtcttttgag aacactgaag   6420
agttttgatc cattattttg ctgactgtct gatgtgtctc atgattggac tcaggacatg   6480
catccttagc aaaaagacca cagaaatggc tccatgcctt ttcactgtgt gttatatcac   6540
tgggcttgtg atgtgccata cctggtgatg ctgactttga gaacctgata ttagaggttg   6600
ctgctgggct ttttcattat acaagagaaa gtgagatgag gaacacaata cttgcatggt   6660
cttaaagtta cttccacaaa ctgcatactg gttgcaaagg gagggaaaa aataattata    6720 aagtgggaaa atcaggcaac acatttgact gggtgatcag actcatacta ccagtgaagg   6780
acagatggta tcacatgcct ccaggtgtaa tactccaaga aggacacagt atcacttgta   6840
```

```
ttctggccaa gaatgcgtaa actcaagtct actcacgagg aagcatcaga caacagaaaa      6900
tgaggaatgt cctgtcttat aaaaatctat tttcacggtg ccattaactt ggtagttcca      6960
gtctgtccac taaaagaaaa aatgttaagc cttccaatat agcaaggata cttaatctta      7020
cttgggcctt ttctggtggc tcagatggta aagaatctgc ctgcaatgca ggagacctgg      7080
gttcagtctc tgggtgggga agatcccctg gagatgggaa tggctaaccc actctagtat      7140
tcttgcctaa gggaatcccg tggacagaag agcctggcgg gctacagtcc atggggtcac      7200
agagtcggaa atgactgagt gactaacaca cacttggttt acttttgcat tttaaaatgc      7260
agtaaaaagg taactgaata aggtcaaaaa ctaagactgc agatcatgta actagaggga      7320
ggaggacgaa acaggaatag aggacaggag gaatgggaga gagccagcat ttgtttggaa      7380
cctgctgtgc actagaactg cacagggtcc tctctgcctg tcatctaatg taacccttct      7440
agcagtgctt tgaggcaggg actagacacg cataacaggt tagataactt gaggttgtaa      7500
agctaatata tggcaaagcg aggattcata tctgggtctt ctgattctgg ggccagtttt      7560
tttcccgtat gccatgttgc cttctcttaa aactgaattt tttcaagaag agtcagggtt      7620
tctcagcctt ggcactgtgt atattttaga gtggataatt ccttattgag ggaggttgtc      7680
ctaagcattg taggatgttt aatagcatcc ctggcctaca cccattaggt gacagcaccc      7740
ttccagttat aacaactaaa aatgtctcca gacattgccc tgtataccct gcctggggtg      7800
gaggtaaggg ggtaatccct ggttgggaac ctctcctcta ataagggtta tgtcaagggc      7860
tattggaggt tccaggcgga gcagtcagct acttccttat taagtattta agaagggaga      7920
gagaaactcc agtcagaaag accaggcaca tgtagaaggc ttctgtggta gtcctttgtc      7980
tggatattat caacctcatc ttctcagttt tttctggctg ctgctgctta atcactgaat      8040
gtttgtgctt tttttatctt tacatttct ccctggatga tcttacatgt tcccattgac      8100
ctctttcctc tctgagctct actttggcat atccagttat caacttgaca tctccacttg      8160
gatatcttag aaatagtagt tctgagcccc acatcagatg tgctaaatca gaaactgcaa      8220
gtgagggtct ctgttttaac aagccctctg gaagatttag atgcttgctt aatcccaaat      8280
tttcaccatg tcagtaaatg gtgtcaccat ctagccagtt agttgcttaa gccagaaatt      8340
tgagttctcc ttaattttc tttttccttt atcaccacag ccatttcact tctaaaccat      8400
gaggaaatct gtctttgtct tagtccattc aggctgctat aacaaaatac agtagactgg      8460
gtgacttata acaacaatta tttctcatag ttctggagac caaaagtcct ggatgatggt      8520
tccaatatgg tcagtaagc gctctcttct ggatttcagg cttcacattg taccttcata      8580
tggtagaaag agcctgggag ctctgtggga tctctcataa gagctctaat cccatttgtg      8640 ggattttccgt ccttataccct attcacctgg caaagtctcc acctccaaat accattacaa      8700
tgggtctgaa gagtccaaca catgaatttt ggaggacata acattcaga cccgagtaaa      8760 gtcctcctga tcaagctctc aaatatatct tcagtgtact gattttcaaa ttaaggtggg      8820
gttatatccc aataaaccca ttttaagttg aaaatataca ttgaaaaata tcgtaaatcg      8880
aaaatgcatt taatacacct accaaacatc gtagcctaac cttaccttaa atgtgccaag      8940
aatactttaa tattagtctt cagttgggta aaatcatcca acagcctgtt ttttaataaa      9000
gtcttgaata tctcatgtaa tttattgaat actgttctga aagtgaaata ctgaatggtt      9060
gcatgggtgc agaatggttt aagtgtattg gtggtttatc cttgtgatcc caaagctgat      9120
cactagccca ggaaagggca aaatttgaa atacagtatc tactgaaagt gtatcacttc      9180
```

```
tgcaccactg taaagttgaa aatcaaagtt gatccaatgt tttaagttgg ggaccacctg    9240
tacttcatct tacaaagtac ttcaaactac agtagctatt tttacagttc tgaggactag    9300
aagtccagga tcacagtgtc ggcgttgttg gttcctacta aggctgtgac tatccgtttc    9360
acgcctcttg cctagcttct cgtcgattgc tgacaatctt tgagattcct ggccttgcat    9420
cacccacccg tggtttctgc cttcatcttc acatagcgtt cttgctttgt atgtgtttct    9480
gtcccaagtt tcccattctt ctaaggacat tagtcatatt ggattagggc ctacccatgt    9540
gacctcacct taactaatta cacctacaat gaccctgttt ccaaataaaa tgacattctg    9600
aggtgctggg gattagaact taagcatgaa ttttgcaggg gaacacagtt cagctcatga    9660
cttctctgat gacgtcagtg taggccatta tctctctatt gatcactgta gcaatctcct    9720
agcgtatttc tagttcattc ttaaacccct ctatagtgta gtttctgcca taggaggaag    9780
actgatttat tttttaaaca tctgtcatgt ccctctcctc ttttctcttt agttacttct    9840
gttgcatttc gacaaaaatc tgaacttcct accatggcct acaagattct tatcatctgg    9900
ttctctcgaa attcatcttg tgccactctt ccttactact tttcatccaa attggtcttt    9960
aaaattttt ttcaggccat ccaacttgcc aaacgccttg ctccttcagg acctttgcgt   10020
gtaacaatgc cttcatctga agtgtcttcc ttttcccct tgcataacc agcttttct     10080
catcctccaa ttctctatat ggaaatgtcc tccacctcag agaagctttc tccctgacta   10140
ctctagcgga agttgcctcc ctttcctcaa ttactatctg tttcagtctt ttcaaccatt   10200
tcttttctg attttttttc ctgttatcct ttttgcttct gtcttactgt aaactgagtc    10260
agactgtgtc tgtcttgttc attcttgtat acctaatgct gaggaagagg aacatattca   10320
gagtatttgt tgaatgaatg tatatcccca agaacatagc tcaatacca gtgctgatta    10380
aatacttaat aaatgtttgt agaatgaacg tatgaataaa tttcatcttg accacccagt   10440
atcatcttat gatccaccct ctataatgtg aacacatatc ttattttga tgcctggagt    10500
ttctgaaaga tatgattctg acagatgagc gttttcata ttgggagttt aggtcattca    10560
aatagggaaa ttgttgccag acttgtacct tttccttccg ttctttgtag ctgactgacc   10620
tccttcagaa tcaggcggtg agaggaaaaa ctgctggagc actgctgaaa gccatcttca   10680
aaggtaataa taatgcctct tctctctctg ggttcactgg tatgtttgtt acttttggc    10740
tcctattgct actctttgta ttgcttgaag ccccgctgaa acttttctgt tttgggatt    10800
ttacagaatc aatagcacta tcttgtggac ttaaataatt tttctaaggc aggtagaagt   10860
ggctatctga gattgtattg ctagttttag aacctgtaaa ggttgtactt cataaaatac   10920
ggtttggttt acttgtgctt ttaagcttgt ggagaacggc aatgtttaat acttaatctg   10980
tgtttaacaa gaggctaggg agctctgagt taaagaaatg gaataccctta gttgacttat  11040
ttagagatgc ttaattccca gtggggaata tttgtttctg tatcttgaac aagggccagt   11100
tttatattgt ggcagattgt aactcacaat cattttataa attgtagtag aataaaattc   11160
tataagcaca aattaaaagt ggctttagac tcttaggagg ttattttaac ttggtttatt   11220
tttcttaccc cctcaagtaa ttgggtcttg ccttgcaagg gttcaaaaac acatatttaa   11280
aatttggaaa cttttaaat gactgttctg tagaaatatc tgagaccagg aagtaacaga    11340
gaatcaggag ctgctgccta tgtatactaa gtgaaagtaa taagagtaaa actgggaaca   11400
gattatcatg gctcccactt gtgtaactaa ccttattttt accttattta aaatcataga   11460
tttggaaatc tgagtttcaa attagcatga attatcgaat atttatgaa actgcctcat    11520
aactatttta atcctgttaa atcagtgctg tgaaggacca atagttagct aatgatacgt   11580
```

```
tttataaaat tgagatataa tccatgtact aaaaaattca ccctttttaaa gtatatatta    11640 ttttattgag atgtaattga catcataaaa ttcacccact taaaatatca attcatcggc    11700
ttttaatata ttcaccaaga tgcacgcctg tcaaaatttt cgagtatttg tattatccct    11760
gaaagaaacc ttacattcct tagctgtcac ctcctaaatt cctgatccac tccagcccta    11820
agaaaccact tatctgcttt ctgtctatag atttgcctat tctggatatt tcataaaagt    11880
ggaatcatac tgtatgtgtc ctttgtgact ggctgctttt acttcctgta aggttactaa    11940
gattcgtcca tgttgtaacc tgtatcagta tttcatttat ctgttgaata atattccatt    12000
atctgaatag atcatacttt tccattcatg aatgggtgga catttaggtt atctacactt    12060
tttagcaatt atgaatcctg ctacaaattt ttgtgtaaaa cattttcatt tctgtttggt    12120
aaatatttaa gagtagaatt gctaggtcat attggacaca agcgaagcgc cttagtagca    12180
gtggcagcat ggtgactctg tgtctaagtg tttgaggact gatgagctgt tttccaaagc    12240
tgctgcatcc tgtttccatc actattgaat aagaattccc aatgcccaca tcctttgtca    12300
acacttgtta ttgtcttttt cattctagcc actctggtga gtgtgaaggg gtatctaatt    12360
gtgggtttga tttgcatttt gctgatggct aatgatattg aatatctatt cttgtgctta    12420 ctgaccatt tgtatgtcttt ggagaaatgt gtgttcaaat tatttgacct tttaaaaatt    12480
gattgtcttt ttattactga gttgtaatat ttaaatgttc tagatatagg tcccttatta    12540
gatgtatgaa tcacaaagtt tttttccatt ttaggttctt ttcatttttt taatggtatc    12600
ttttgatgca tgaagtttta aatttgatt tttttttta attaaaaaaa attaattttt    12660
tgtagcttgc acttttggtt tttatctaaa agatcattgc ttaatccaaa gttacaaaga    12720 tttataccttt ttcaagattt cttgaaaaga tttcttgtgt tttcttttca agattataat    12780
cttagctttt acatgtaaaa cttttatcca tttttgagtt aattttttgta tatgatgtga    12840 ggtaggagtc cagcttcatt ttttccccatt ttttttcttct ttttaaaaaa tattttatttt    12900 atctggctgt gctatgtctt agttgcagca tgtgggatct agttccataa ccagggattg    12960
aacctaggcc gcctgcattg ggagcacagt cttagccact gaaccaccat agtaccttta    13020
ttgagaatca attgcccata gatgcgaggg tttatttctg gactcagagt tgtattccct    13080
tgatcgagat gtgtctcttt gtgtcagcac cacactgtct tgattagaat agctttgtgg    13140
taagctttaa aattgcgaag tgtaagtcct ccactgtttt ctttttttaga attagtttgg    13200 atattctggg tctcatgagt tctcatatga attttaagat tagcttgtca atttctgcaa    13260
aaacggaaac tgagttttttg gtagggatta tgttgaatct atctatggaa agtattgcta    13320
tctttatatg tcttccatta ataaacatga catatctttc catttactta ggttctttttt    13380 catttctttc aacaatattt tgttcttttc agagtacaag tgttgcacta cttttattaa    13440
atttattctg aagtattctt tgagtgtgat tgtaaatgag attctttttct taatcttctc    13500 attgttcagt gctagtgtat agaaacacag tagatgagta tattgatctc atatcttgca    13560
accttcctgt acttgctgat tagttctagt agtttcttttt ttgtggagcc cttataaaca    13620
aaattatgtc atcttcaaat agatgtaact ttacctcttt ctcaatctag atgcctttta    13680
tttttctaac ctagttacct cagttggaac ctccagtaca gtattgaata gaaatgctga    13740
gagtgaacat ccttgttttt ttccctgatt tcagggggaa atctttcagt tttttattag    13800
caagtatgat gttaagttag ttaagtctct cacttagtca tgtccgacct ctttgcgacc    13860
ctgtggactg tagcccacca ggctcctccg tccatgggat tctccaggca agaatactgg    13920
```

```
agtgggttgc catttccttc tccagggat cttcccgacc cagggatcga acccaggcct   13980
cccacattgt gggcagacac tttaacctct gtggtttttt catggatgcc ctttatcagg   14040
ttaaggagtt ttccttctat tcctagtttg ttgagtgttt ttttttttt aatcatgaaa   14100
cagtactgaa attttcaaat gctttctctg tatctgctga ggtgatcatg tgacttctat   14160
cctttattct atttatgtgg tatatgaaat tgattttcat acattgaacc agtattgggt   14220
tactgggtta aatccagttt ggttagagag tacagtcttt gttttatgtt ggtgaattta   14280
gtttgctaat attttgttga ggattttgc atctgtagtc acaaggaata tcattcatag   14340
ttttcttaga atgtctttgt ctgctactgc tgctaagtca cttcagtcgt gtccaactct   14400
gtgcgacccc atagacggca gcccaccagg ctcccccgtc cctgggattc tccaggcaag   14460
aacactggag tgggttgcca tttccttctc cagggcatga aagtgaaaag tgaaagtgaa   14520
gttgctcagt cgtgtccaac tcttcgcgac cccgtggact gcagcccacc aggctcctcc   14580
gcccatggga ttttcgaagc aagagtactg gagtggggtg ccattgcctt ctccggtctt   14640
tgtctggttt aggtataaag gtaatactga cctcatagac tcagtttgga aatgttacct   14700
tctcttctgt ttttttggaa gagttgctgt taattcttta aatgtttggt gaattcaccg   14760
gtaaagccat ttggttctgg acttttcttt gtagaagagg ttttattgct aattcagtct   14820
ctatttataa gtctgttctg gttttctatt atctttttta gtcaattttg ataactttgt   14880
gtctttacag caatttattc atttcatatg ttgtttattg tattacttta ttttatttt    14940
ttttaatttc tgcaagatta gtagtaatgc cactctcatt cctgattta gtaatttgat   15000
tcttctctct tttttcttg gtcagtctga agatttttca actttgttta tcttttcaaa   15060
gaaaaagatt tggtttcctt gattttttatt attctattct ttcatttatg tctgatttta   15120
tttttatatt cttttcactt ggtttgactt tagtttcatc tctttataat tccttatggt   15180
agaagcttgg gttattgatt tgagatcttt tttaatgtag gtatttacaa ctgtaggttt   15240
cgttttaagc tctactttag ctgtattcaa taacttttgg aatgtgtttt tttcttccca   15300
ttcacctcaa ggtattttc tctcttttcc tgctgacttc actcagtgat gatgttttga   15360
agtaaagtat gttacttaat ttgggttatt ggatcccgaa aagctttaag aaatattaga   15420
aggtgttcct tcttctgcac tataaaatta ttttaaaaat taatggcatg gatggaagtg   15480
tacagaaaaa ctggtatttc agttttctgt ctaaattaaa aaactttttc aaagctccta   15540
aatattggct gttctaagta ccatagtaag tattttgata attctgtttc tgtattcaac   15600
tgcaaagctg tttgttattc ctgtttgccc ttcaaccttg tcagacttct tccttttttc   15660
tttctttgtt tctgtgctac ctgttgaaaa tgataaggtt taccctgttc tgaggaagct   15720
ggagctctta agagacttaa gatatacagt tgttgtatcc agttgttgga atcagggat   15780
ttacagaaag aagtagcatc tgaaatcaca ggattgctaa tgctggaggt gagatggaaa   15840
acaaaactgt tttggttttg gttgaatttg gagcggggtt ggttatatgt tgagggaggg   15900
aaaatgtaaa cgtctcagac ccaccatagt tcctacttac aagtaagaac taccgttcta   15960
aaacaaaata gccgatgaat gagccataaa ccacctagat gtttatgtta cgtttccagt   16020
atcatgggca tgtgtctctt tcaagagctg aatatttaa gaacatcagg gaactaatgg    16080
aagatcctga cctttgaaa tccttaccca gagcagaatg attccctgaa tcactttag    16140
aacccgtttt gggcttcaat gccagttctg tcaactcagc aaaagactga ttttggaaa    16200
gaggtatcaa acatctagat atctgctgaa tgttttttaa tcccatgaac tttaggttca   16260
ccgttttccg ggacagctat tggttgaatt agccaatgag tttgttagtg ctatcaatga   16320
```

```
aggcaagctc acaaacggaa aatctttgga gctgttgccc gtcattctca ctgcccttgg   16380
taccaaaaag gaaaatctga cttatggaaa aggtaatttt tcttccaatt tcagtggctt   16440
gttctttctt cacttaatcg gatttattct tcagtgtatt ttgcatttct aggtgaacta   16500
agtggggaag aatgtaagaa gcagttgatt aacaccctct gttctggcag gtaagtcctt   16560
aataatatga agaattttc tcaggactat aagtcaccaa aaaaggaat accattattt   16620 tgggaattta tatcactgaa gttttagtcc attttttgt ttatgattta ccactataaa   16680
accatttagt ctgtgatgag ttttttgagag aggttatttg ctgtattctt tattctaaca   16740
ttatacatat agtctctact tacttaactg tcatcctaac acagcaattt agccctatag   16800
tattatttgg agtcccaggg tcttcaaggc tagaaagtca ccttgccact atcttttatt   16860
ttggggcggg ggggatatat aagtgatatt tttatcatta agcctgatat ttgtatcttt   16920
aaacctgaaa tacaagtgtc tatgctaagg aaaaactgca ttgtataaga aagtcttcat   16980
acatgaacat ttcaatacag aaatttgtga ctagcttaag gacacaataa tagagatatg   17040
taagttgtgg tatgtaagct ataaaagagc cactccatgc aatttatacc cattaaaaat   17100
gaaatatata aagacatata gcgaagatga aagatctttg tgtatatatg tatatatata   17160
gtaaatcctt aatacgtgtt tttatatata tagcctgaaa tgaatagaat actaagttac   17220
ataatactgt gattatactt caatatgttg aaaggaacta gattatccaa accagagata   17280
actgctttca tggttcataa ggtctcttac agaaataatt ttaagcatgt atcagctcag   17340
gtatgtttat ccatttattc ttaattacac aaaatattat tcattctaca ttgtaatgta   17400
ccttgcattt ttcatttaac acatatgttc atgtcagcat atactacttt acatcattct   17460
ttttaatagt tccatagtat tctaatattt ggctaatctc taattgttag attatttagt   17520
ttttgccagt aaataatatt ggctatttgg gtttttgcta ttataaaaga tgttgcagtt   17580
aacattcttt tatgtctggg tgaccttta taagcatgta catgggatat attcctaata   17640
gtaagctggg tggctctttg gttatgtgca tgtttaaagt cggtaagtag tattgccaac   17700
ttgtcttccc agaaggatta tatcagtgta tgttccacaa aatagtatgt gaagtgtttg   17760
ttcaccaaaa tctcaccagc actgaatgtc atcaggcttt gattgtgcca gtccagtagg   17820
ttaaaagctg ttatttcatt gttttaaatg tcatttctttt gatgttattt cccagtagca   17880
gcaaatcaaa cttgaaatgg ccctaattct tttcttcctt gctaatttta taagtaaca   17940 tgtaaataag ttaaaacaac ataaacttt ctttttcatt tttaatcaga tgggatcatc   18000
agtatgtaat ccaactcacc tctatgttca agtaagtatc atcattccct tcttttttaa   18060
tcctgctgtg agaacttacc tgctagaaat tgaaatgtag taagctcaaa taccactgtt   18120
cctgagtaag agtattgata cctctgtttt ctgttacaag atttccccc accctttttt   18180 gctttaattt cttatttaaa gtatatgatg ttttatttcc aagataactt tgctgaggaa   18240
agattattgg tttcctttaa ggttctccat tagagaaaaa tcaaaagacg caattaacaa   18300
cattctgata tctcccaaat tggtctctaa cctttagaat ctttgatcca cagggctgtc   18360
cctctgacta cagaagaggt ggaatttgtg gtggaaaaag tgttgaaggt gttctccaaa   18420
ttgaatcttc aagaaatacc acccttggtc tatcaacttc tggttctctc ctcaaaggta   18480
taaataaaat attttttttaa actctggtgt aatgaccaat tattaccatt cagtttattc   18540 atactctttta ttttatgtac taggacatag aaactttcat ttcacatatg acaatttggt   18600
ctactaaaaa tgtcatggtc ctcagagtga atgtgtgtta tctctggtct cgtgtgtgtg   18660
```

```
gtaggaagag ggatgaagag ctctgaaagg gtggattgta ggcccctag agtctgatat    18720 taagatgtat ttcaaactct gtttcaaaaa gtgttttat gaaagtgttc tataaattct    18780
tagtgtgagt ctagcttata atttatttaa attcatactt gaaaattctt taagttgaaa    18840
agtagtttaa cttgcccctta tttattttgt tttattcttt ttcagggaag ccggaagagg    18900
gtcttggtag gaatcatagc tttcttcaac aagctagatc agcaacacaa tgaggaacaa    18960
agtggtgatg agtgagtcaa agagtataga aataaaatca tttttccaaa ttcatcatct    19020
cattatctaa ctcttcagtc cctaccttcc cctcagctgc tcagtaataa agttaaaaaa    19080
tagtgtagtc tcctcaactc ttattttaat cttcctgga aaacagcaat aatgactctg    19140
tagttataga cttcaaaggc atttattaag tgtttactct gtgccagaag ctattggacc    19200
tgggacagtg atgaaccagt caaagttcct gctctcatgg agaaatttta atgagaaaag    19260 aaagaaatg acaagaaaag tattagagtg gaaagggcta tgcatacgtt tcaagtggat    19320
gacgtgacag tgacagcatg gctacgttag gttgagggt cagggaaacc tctgagaatg    19380
tgctgtgtta cctgaagcct gaaggataag agccataata tgtagctcaa ggaaaaaaac    19440
attctcagtg gaagagttag tccaaaggca ggacacagca cggtatggct ggaaaagagt    19500
ttttgaagca aatatttgta gaatgcttgc tgtgtgccaa gtactgtttt ttagcactt    19560 aaacttcaca gcaactccat tttgtctctc ttttatacat ggagaaacca aggcacagag    19620
aaattaaggg atttcctggg gttatatagc cataaattgg tggagctgtg atttgaatgc    19680
aagcaatttg tctgcagcat ttgtgctttt aatcctatct caatctacta acctggaata    19740 acaatttaa gttgttgtac ttgagcagtt gatgagaagt tgttcttgta tactgagtca    19800
ggaaagactg acagaacaag caggtttaga ggagaagaag ctcagttttt accatggaag    19860
tttgagatat gtattagtat cttatatgaa ggtgctgagc aggcagtctg gagtttcagg    19920
gagaggttgg gaccagagat acagattgga agggactgaa gcctgcaggc tctttagggt    19980
ccctggggaa gttgtgaaaa gagaaaagga acccaagatt gaactctcag aggcattcca    20040
ccacttgaag gatgagccag cacaaataat ttgaggccag tgacagtgcc ccaggagcta    20100
agagaagaac atgtttccag aaagaaaggg attaactgtg tcagatctac tgaggcttta    20160
attagggtga gacttgagta ttgattttga caatgtagag gtcatttgta gcccttgcaa    20220
ggataatcaa atagcattgg aagggaggtt agggagggca cagaagctta attgagttgg    20280
atttaactgg ggagaggtaa acaagtggaa ataatgacca tagacagttc attcaggaag    20340
tttcatgaaa aggagcaaag aataagtaga ttttgtactt tctgcctgcc tccagtgatc    20400
ctgttagttc agcctgagtt tttctattcg ttcatatgag caaatgcact gttgtctctt    20460
ggtcaagcta tagctcaaac cttctgttg aatcttttag gtacttggat cttattactg    20520
taccattgga tgaacttcgt cacgtggaag gcaccattat tctacatatt gtgtttgcca    20580
tcaagttgga ttttgagcta ggcagagaac tcctgagaca cttgaaggta gtaaccagac    20640
tcttaaggtg atccaggatc tctatgaaac aaggacgttt gaactcaagc ctctttttat    20700
gccgtttaat gactggaaac caatacatag aaatactata gaaagaccct gggtctagag    20760
ggtctctttt ttaactttga agtggaaga tacatgatac cactacattt ttaagcaagt    20820
ccctttttaa aaccagacct taagtgttct agtgttttc tgtttgtttg tttgtttaaa    20880
gatgaagact gttctgtagg aaattcaaaa tttagcctta gctccattat tatatgaact    20940
tcactcttga cttgtttcct tatttgcaaa ttggggaaat tgtctctttc tcatagtaaa    21000
tcatggagtt ttgtgaagct aagtcattgt taaatattg tgaagtagta agataaaaat    21060
```

```
tagaaatgtt ttgaactctt aagtattttg ctacatttac cttatctcac ctctctcaag    21120
tatatttttt ctgaaccatt taaaagaaga aatattgaca cttcagtgcc tgaatatgtc    21180
cacatgtgtc tcataagaat aaggattaat acctttttat tgaattttt taagaatcct    21240 gcccagtttt cttgtgtctc atattgtcag atttgtctta ttgtctcccc atgattagat    21300
tcaagttaaa cattttttggt gagaatatgt ctcaagtgct gttgtgtttt ttctcttgtt    21360
ggagtcagca aactttctct gaaggaccag ataaactatt tcaggctttg cggatgacat    21420
ggcctctgtc accactacac tactcttgta gcaagaaggc agctggagac aacacatgaa    21480
tgaatgagtg tggctgtggg ccagtgaaac tatatgggca ctgagtttta atttatttta    21540
attttcatgt gttatggaat actattactc ctttgacttt tctcccctca acaattaaaa    21600
atgtgaaaag cagtcttagc tcatgggctg tacaaaaaaa ggtggtgagc tagtttgtc    21660 ccagaggctt taattctatt gcatcacatc aaaaggctca tagtatcagg cagtcttagc    21720
caaatcattt tattaagaca aggaccagca gttttcttca cttgcaaaga tatatgtttc    21780
cctttgtaat tagaaaattaa tccatggggt cataatttga gacatgtgaa aatcctttcc    21840
ttagcaatct tccacacagt ggattttggt ttcccatcta ttaatgattc ttgtcctaaa    21900
tcagtaatta tactgggagt tgcaaaatgg tagaattaaa atcagaagtt tttattggtc    21960
attccttcta gttggttttc tgtgaaaaga gccccacacc tccctctttt ttttttttga    22020
atattgttat gcaaccatga accttttaaa attccatgta ctcataaaca gtacccagaa    22080
tgatccctat ttggccattt ggatccctga ggttggctta tgtgtccttc taacatggcc    22140
atgttagtct ttgagcactt catggcgtaa gctatccaaa acacacctgt gctttcctta    22200
ttgcatctga tttctccaag gagcctcagg tcccttttgt aggagaagat atttaaagac    22260
caaatgtgaa aagtagcctt taaagctcct ttatcttctc tgtgtctata tactcttttt    22320
ttatttaggt ttctagtaac tgttcttttc aaagaacaag ctttgtattt gtttactgtt    22380 ttattttttgt tttttggttt tctctttat tcatctttga tttattttt tcttttgttg    22440 tctgccattt cttttagggc tcaaaaacct attttttaac tttattgagt tacaatttat    22500
gtaatataga atacactcat tttaaagtat aattcagtga ttttcttaa gtttacccag    22560 ttgtgcaaca accatcatca taattcagtt gtggaacatt ttcatcacct tgtaagatcc    22620
ttcatgcctg tttctataga tttacctttc ccagacattt catatgaatg aaatcactta    22680
atatataatc ttttgtgtat agcttctttc attgagcata attttttcaag gttttatcc    22740 atgttgtagc atttaccagt atttcattct tgtttgttgt tgaatggtct tccactgtgt    22800
gtgtgtgtgt gtgtgtgt gtgtgtgtcc gttgattaga tgtccaccag ttgatggaca    22860
ctgcagttgt ttttactttt tggctattag gactaatgct gctgtgaaca tccaaatgca    22920
tgtctttgtg tagagacata tgttttcatt tctcttgata gatacctacc agtagaattt    22980
ctgggttttg taatacattc atgttatat tttaaagaaa ctaccaaact gtcctctaaa    23040
gtggctacaa cattttacat agccaccagc actgtatgag gactcctttt tttcccacat    23100
cctggccaac atttgttact gtctgttttt ttatacctat tctgatagct ataaaacagc    23160
ttattggcca ttctaatatc tttggtattg cagagtcaga catgacttaa cagctgaaca    23220
gcaacatcaa caatctttga tgaaatgtct attcaaatct tttccccatc ttttgattgc    23280
atggcttaca cagtttttaag atttcttgt atattatggg tacaagtcct ttatcgtgta    23340
tgtgattagc aaatattttt ttcagtctgt ggcttgtttc ttaatggtgt ttctttgaa    23400
```

```
gcaccagagt tttgattttt aatgaggccc agtttatcag ttttttactt acataaatta    23460
tatttttggc attgtatctg agaaatcttt aatccgaact cttgaagatt ttctgctgtg    23520 tttccttttta ttttttttttc ttgtttccag ttctttatat ataaacaaat tctatccttc  23580
caaatgtaag ctatacatta cttcccccaa gtttattcaa ttcacatgtg aaaaaattat    23640
gatttaaaat accaagctgt gtttcctttt aaaagttttt gtaggctttt tttttttttg    23700
gtcatactgt gttatatggg atcttagttc cccaaccagg aattgaacct gcactccctg    23760
aattggaaac acagagttaa ctgctggact gccagcgaag tcccaaaagt tttatagttt    23820
tagctcttag gtttaggttt ctgatccact taaggacctg ttattaagta gaatatgttg    23880
tatttttcaa atgtaagtta tgacttcttt ttggtttgtc tgttctaggc aacacagcaa    23940
ggagatttca gcagtatttg tccttcagc atcgccctct tgctctctgt aacaagaata     24000
caaagatttg aggaacaggt atttatgagt gacttttggt ttccttctgt agttgataag    24060
gagtgtaaga gcctgtttat cctttcctaa ataatttcac tcccatcctg ccagcagcaa    24120
attcccctgt aagaatgtag gcccacactc ttctctggga gctgcttgaa gacttcttca    24180
gatacttgat ttatacttct gtttcaaact atgtggcaag ccagaggctg agatgggaat    24240
agcagtggga acatcacaca gtccaggtag caagaatggc aagtttagct gggtattcat    24300
agcagtcgta ttatgttgta gcttctctaag aaatattcct tgaccaagtt gaaattaatg   24360
agaataggtt tcaacttggt caaggaatat ttcttagaaa tattatttgc aagaatgaaa    24420
atataaaatc ctttacccctt ttttctcata cgtgtttccc tgggtgtggg taatattgat   24480
ttttagccat ttttctctca agtcaggcat gtcttcagct ccttttaagt tctcactgaa    24540
agttataatt tttgcgtcat gctcatctag tgaaacagtt atagggatat gagtgtgtgg    24600
cagcaagtag gaacagttac agggttaaga ttctctagta tgggctatac attttttgctt  24660 cattttccta tttctttcat tatgttaggt gtttgacttt ttaaagtctt cagttataaa    24720
aaactttaag gatcttcagc ttctccaagg ctcaaaatat attcagagtc tatttcctaa    24780
tgaatgttgt atttcaacca tgatcttgga agtggtaaat aataggtaag tttatgaacc    24840
ataaggttta agctatttag tgctagaaaa tgcagtgcgg taccatactt atggcccatc    24900
agagaaaact gttgactata gttgttgact tcacatatca aggtttaaat cccttaaaat    24960
tgatcaagca gacttcccct gtatcaacag attctaaaat cccaaggctt gatttcttgg    25020
ccaccttgtt agcaagaata cgaaactgaa gtcggctcct ttagtactat tactgctctg    25080
ttggtctaag tcttcattgg ctttttaggt aaataaaaaa cagatttttt tactgtaact    25140
gttggagttt gggaatgatg gatggaattg aattagtagt tttagacaac tgacgagcag    25200
ttttaggcaa atctatcttt aaccaaatat agaagtaaaa atagaaaaaa tagaaaaaaa    25260
actggttacc atcctggttg ttatttcat ggttaatgtt gtatttcatt gtatacatgt      25320
atacatcagc cgttataata ttctttactg agtcatgctt ttttgtggt tttggtttgc      25380 tgtatttagc tctgttgaca atttctgtgc ttacctgcag ataatctgaa ggtgcaaaac     25440
attaatgtac taggaaaaaa atcactatga accaatacaa cttctaggtt gtacttactc    25500
ccatctgtac caatcacata tgaactcttt cacattacag ataagacatt ttgtagcaaa    25560
atggattgta actgcctctt ctctccaaaa tgagaacttt agggcacaat ttctccactt    25620
ccttcttgtt cagcattatt actaacaagc aatacttact tagacttcat tattttactg   25680 gtttcttttgt ttgcatttat cttttgaatc tcatactttg gcccatctga tttctgcttg   25740
gtgtttaatg taccctttcca ctataaggat tcatgtattt cctcttgaaa tgttttctctt  25800
```

```
cattttttt   gagtactctc  tccttttct   cttggaatat  cttgctctgt  atactatgtc  25860
tcaatttttc  tttcatactt  tatgtatttt  tgtcttttg   tgtcaagttc  tacaaaaatt  25920
cctgggactt  tgctcatggt  ccagtggcta  aaactccatg  ctcccaatgc  aggagccctg  25980
ggtttgattc  ctaatcagag  aactagatcc  tgcatgccac  aactaacacc  tggcacagcc  26040
aaaataaaat  aaaaattcct  gagctcattc  tttagttact  tcttcagttc  tgtgcatttt  26100
attcttaggc  catctgctga  ggttttcact  ctatccatca  tgttttttat  ttccaaaatt  26160
tccacttggt  tgtttttca   taacagttta  tttttgttt   cttgcaatag  tctttcttct  26220
ctgagaatat  tcattagact  tttaaaatct  tctatttgtt  ccattaatct  tttcccatag  26280
gattggttct  ctttgttgag  tttggtgctt  ctctttcctg  gtcgtattat  tttcttgtat  26340
ttggtgatta  cttatttcct  tattatcata  tttgacgttc  cccattagtt  tgtctgagag  26400
tgctgtattt  atttaacaca  ctctacctca  gggatacgag  ggtagcagta  ggatgtacca  26460
ggggctgatc  ttctaggtat  ggtgtctccc  tcatccttca  gcatgttgtc  atcctctcag  26520
agtgctgctc  tgcctctcag  gccccagatg  cagtgaggtc  ttggagaaaa  aggtggagaa  26580
ggttgatgtg  tactgaactt  catccagggg  tatcctagcc  agtcaccaca  aaagttgccc  26640
cagggttcct  tccagttccc  agcatacccta  cccttggcat  ccgcttttgg  aggcacccctt 26700 tcagtctgca  taatgctgtc  tatgatttct  tttttccttc  tattactttc  attttttaag  26760
gattcttcat  aatttctaga  cagtcaaagc  acctcttatt  tttccacgtt  atcatggatt  26820
gtatgcatgc  accacatata  gacattcaca  cacagttata  tctatctttt  ctgtcatttg  26880
taagtattca  ggttgggaaa  atggagcat   gtactcattt  tattatcttg  atcccagatc  26940
cccagagtgt  gactgttgtt  aaaatctgtc  agaatgttat  gagaatctat  tcacaactct  27000
ttcattcttt  aatgctgcat  tataatttgt  tgctgtttag  caggtagatg  taatgatata  27060
aaggttatta  taaacatgat  ttccactata  gtgggtaaca  ttaagtggta  taaaatcacc  27120
agggattctc  ttgcttttcca aaggttggtt  gtagttttat  ttcatgcttt  tgaaatccag  27180
tcattcatca  gaccaattcc  tactataaat  atgaatatga  aataaatatg  aatataaatg  27240
ttcctattat  aaatatttac  cgagtacctt  ctatatgcca  gaatttgtgc  taggctctat  27300
gagcaaaaat  atgactacag  tgtgctctcc  accatagaga  atctcaatct  agagaggaag  27360
acaaacttgt  aagcatatgt  atatgtgttg  ttattggcat  gagggaata   gtagaagcag  27420 aaattaaaat  gtagtcatga  aatcttgagt  ggcaatctct  aatgatctgt  acactgaaat  27480
attccagttt  cttccatatg  ttgcttcatg  ttccatagtt  tctggatttt  catggtgatc  27540
tgtcggtaga  gattgcttgc  ctaccaattc  cccattactg  ttcctccaaa  aattcagaat  27600
tttgccagat  taagggtaca  tgaaaaggaa  agactcatgt  ggggtgttgg  ttatacaggt  27660
caggtttggg  aaatgtgtaa  catggcaaag  agtgtagagg  taaggtgttt  tattaagttt  27720
ttcttcttaa  ctaaactttg  ttttcctgca  gtgttcatag  ttgggatcat  gttactcagg  27780
gcttggtaga  atttggcttc  atttaatgg   attcctatgg  gccaaagaag  attcttgatg  27840
gaaaaactgc  tgaaaccagc  tcaggtcttt  ctagaatgcc  aaaccagcat  gcttgtaagc  27900
tgggagctaa  tatcctattg  gaaactttca  aggtgagact  cgagttcagc  aaccattccc  27960
tcattttgtt  gtattatact  acaaatagga  cattcacctg  ggagtttggg  ggactgggca  28020
atttgagtat  gtagcagttt  ctgagaacag  aaactgggat  aatagttgaa  acattaatag  28080
atgcagtttg  atgaatactt  tctcagtctt  tatctgagtt  tttcatctat  tctaatttct  28140
```

```
gttctttctg accatttctt agaagtttga atataggtta gcttccttat gatttcctct    28200
tcttcctcca gcagtaaatc atttctgaat ttttttttat acccttatac aaaaaataat    28260
cttttaggtc gctgtagaac atcaaatttg aagaatcatg cctattggtt tattgttttt    28320
gaagaacccc aaatgggaaa ttcatattct tttaattcat taccatatta cgattgttat    28380
ctcaatctaa ataagatcat atctgaggct aaacaaattt gctttgctag tgatttctct    28440
aagtcatctt gacatccatt cttcagtgta tctacatacc aaaagtatct gctaacagtg    28500
ttatttggag gtcaatttaa atgtaaatct gatgttctga tccagaagta aagtgaatac    28560
catataatag tccttgaggg ttgtatgtta gatacacatg actctttaac agtaatctga    28620
ttttaaaaca ttcttagaat aagagactta atatttttg tttaaaatt agtcttttt    28680 ttaaatcaag gttctacttg gttcacacag ttgttggcct tgtcacggta tctgtagaac    28740
atagaattta ctaataatca aattattaat ccagagtctg aaagaaatca gtctctaccg    28800
aaagtaatca agttcaggta tgaaatttag ctaaagttca agtaaaaatt caaaacaggt    28860
cctttttaag gcaactactc tgcttctaga aactgaggac agggttattg aagattttct    28920
agattttcag ggtttttta tgggctttta aattttaata tgaaagttgt gcatactgtc    28980
agaaatatgg acgttgacct aatagtagat acctaggtag aattattcct gtttgctgct    29040
ggaccttaca tgtagcagta ctttcatatg atctctctat aaggctaata aaagtttgcc    29100
tggttaatga atcatttgag tacaggatga taattcaatg attctttcca gatgattcgc    29160
ataatgtttg tctttgaaat aagcagtcca gttttaccca tattcaaact tttctttatt    29220
ctgcctaata ggtattaata caattgtaag ctgaagttca ccaaggaata ttttattgat    29280
tcttctgctc cttttagatc catgagatga tcagacaaga aattctggag caggtcctca    29340
acagggttgt taccagagca tcctccccca tcaatcattt cttaggtatt gaactttgaa    29400
agggtggaaa aagttgtcag gaatattttt atttaaatgt cataatgctt tggatcctgg    29460
gaaaaaacct gaatgatata gtagattaat gcaagatctt tgattatgat gccagtaaaa    29520
ataaattctt ttatattgtc tatggttgtc aagaaggaaa ggagcatatg agtgaaactt    29580
ctactttgca tcagctttct ctcttttttg ttttaataat tgtcaagtga gtcctgtcct    29640
tctgctgtct acttattgac ctcccactct cttaaccctt gacattctga cttcattggt    29700
cagagtgacc agtggtcatt tggtgacctc tttggtctct ttggtgacct ctgaattttt    29760 tgttttttc gtacatattt cctaatgcct aaatccactc atcttaatca tcaacttcct    29820
taatttcctt ttcattctac actatttata actctcctga agttctctga taactgtaat    29880
agtttgcatc ttttatcctg cctttgatca gttttctttt cttcttagag attggttttc    29940
tttcttctat ccttaaatgt caaggttctc caaagttcta tacttgacat tcattctac    30000 tttttctttc tttacattca gctttactga aatacaatga ggtacagtaa tgtacacata    30060
tttacagtat aacagtttga cttttggtgt gtgtgtacac ccgtgaaatg gagaccatca    30120
ccacagtcaa gatgaacata tctgtgtggg cgctaagttt tcagtcatgt ccaacccttt    30180
gcaacctcct ggactatagc ctgccagagt cctctgtcca tgggatttcc ctggcaagaa    30240
tactggagtg gtttgccatg ccctcctcta ggggatcttc ccaacctggg tattgaaccc    30300
ttatctcctg cattgcaagc agattcttca cctgctgagc cactggggaa gaccatgaac    30360
ctatctatca cccagaaatg ttcctggtg ccttttctg atgtattctt gcatctctct    30420
tttccttccc tgacctatct agtctggtct gcttctgtc actataaatt ttaaatattt    30480
tgtgtaaatg gaatcctaca atatgtacct ttttttttct ttttcctttt ggtttagttt    30540
```

```
tttcagcata attttgaaat ttttccaaat cctttgtcag atacaggttt tgcaaatatt    30600
ttctcctggt ctgtggtttg acttttaatt tttgtaacaa tgtcatttga agagcaaata    30660
tttttgtcag ttcatcaatt tctttgtata gttgctgctt tttgtgtcat gtatttaaaa    30720 aattttttg ccaaatccaa ggtccctaag gtttctccta tattttctac tagaagtttt     30780
atattttcat ctgttgtact taaatatatg atccagtttt gttaaattct gtgtatggta    30840
taatataaca gtttgttttt ttgcttatag ctatccaatt gttccagcac agttttttga    30900
aaagattatc tttccttcat tgaattacta tggcttcttt attgaaatca actaactata    30960
taatgtgtgg atctatttta ggaatcttct attccagtga gctatgttat gtcttgattg    31020
ctatagcttc atattgagtc ttagaatcaa tagtgtaagt cctttaactt tgttctttt     31080 caaaataatt ttggctattc taggtccttt atatttccaa gtaaatttac taatcagttt    31140
gtcaagtttt ataaaaagtc tgctcaagtt ttgatggaga ttgcctcaaa tctatggatt    31200
aatgtggaag agaattggca tcttaaccat attgagtcgt ctaactcatg aatacagtat    31260
atctctccat ttatttaggt cttcaatttc tttcaacact gttctatatt tttagtgtgt    31320
gtatcttgta tcttttgtca gttgatccct atttcatttt tttgacactg ttgtaaatag    31380
tatttaaaaa ttttcaatt tgtagattgc taactgttgt catgtagaaa tagttgcttt      31440
tttaatgctg accttatccc ctgcagccat gctaaaccca tttattagtt ctagtagctt    31500
ttcagcaatt cttcaagatt ttctacatag aaatcacgtc atctgcaaac tcaggcattc    31560
ttgatatcag tgatttgtct ttttttcttt atcaatctgg cttagaaact tgtcagctta    31620
cagcctttca aagaatggga ttttagtttg aattttctct attggttttt tattttcaat    31680
ttcaccaaat tttgcttttt attatttcct tcctcttgct tgcattgggt tcattttgct    31740 ttttaaagt gggtgaaaaa aatcaataga agaatatttc tgatacatga aaattttaga     31800
tttcagagtc cataaaatat agtattattg gaatactgtg tttaccagca agaggtttcg    31860
gagaaggcaa tggcacccca ctccagtact cttgcctgga aaagcccatg gatggaggag    31920
cctggtaggc tgcagtccat ggggtcgcga agagtcggac acgactgagc gacttcactt    31980
ttacttttca ctttgctgca ttggagaagg aaatggcacc ccactccagt gttcttgcct    32040
ggagaatccc agggacgggg gagcctggtg ggctgccgtc tatggggttg cacagagttg    32100
gatacgactg aagtgactta gcagcagcag caagaggttt atcaatttta ttgattttt     32160 tctaagaccc tgcttttcat ttcattgagt ttctctgttg ttttttctgtt tttagttttt    32220 attgatttgt gtgctttttt gggtcctttc cacttcttac cttgggttta gtctgtgcta    32280
cctttggtta aatgcatgtg tcattaattt gaggtctttc tcttttttt caatacaggc     32340 gttacactgt aaatttccat ctaaacattg ctttagctgc atcctataaa ttttgttttt    32400
tattttcatt ccgttccaca tactttttca tttctcttgt gatttgttct ttaatgcatg    32460
ggttatttag aagtgtgtta tttaggtttg gtctactaat tctatcattg tgttgtttct    32520
gatatgtttt tgttgattta tgtcgtcttc atcatgagtt gtgttttcct gcttctttgc    32580
atcattaata agttttgatc agatggcaga ctttatgagt ttcacattgt tgatttgctg    32640
gatttttttt tccttcaaat attccttgagc tttaagttcc ctggtgactc agatggtaaa    32700
gcgtctgccc gcaatgtggg agacctgggt ttgatccctg agttggaaag atcccctgga    32760
aaaggaaatg gcaaaccact ccagtactct tgcctagaaa attccataga tagaggagcc    32820
tggtgggcta tagtccatgg ggtcacaaag agtcagacac aactgagcga cttcactttc    32880
```

-continued

```
acttgtttct tggaaagtat ttaatccttt tgatgattat ttctgtgttg tgtaatgaaa    32940
gaccattcag cttttaatct agggctaact tgatgctgca attaaggcaa tgttccttgt    33000
atattatgag gtgtgtacag tgtgggtgtt gtgaatgtga actatttcct gcccttatg     33060 acctcagaga atggatttgc ctactccttg ccagtaactt ttagcttcac tcaggttgtt    33120
ttttcacata catatgctga ggagcactca gctcacatgc aaggagagcc ccctgcacat    33180
ctccagggtg cttcactgc agcccttcc tttctagtgc tagctgcctt ggctttcctg     33240
aattctcaac tctgtctcta actcaggaag accactggct tctgagttt tctctgtgtt     33300 cctgtctaga agctctccag gcagtaacat gggacaatta taagcctctc ctcatgtatt    33360
tccctctctc agggatcatt ttgtgtactg cttattatct agtgtttgaa aattgttgtt    33420
ttatgtaatt tggcttgttt tgttgtaggt gtttaaagtg aagataactg gttagtgtta    33480
ctccatcgtg gtggaaagtg tctcttcctc tttttataca ttctcttact tgtagatatc    33540
atcacctctg ttctcacgat ttcagttttg ttttggtttt tttttgtggg ggggagcttt    33600
tgtgggcatg gctcccaaat cttatgtca ggactatttg cttagttcag tgcctgagtg     33660
ccttcattcc tgctagctgt ttccatttag cttttttttt ttttctttta tttcaaatgt    33720
aatactgttt ccttcgaaca acctctttct ttgtccctat ttctgttagc tgaaacatgg    33780
atgtctgagt cccagaggct agaatttctt ttagtcttct ggaatacatt tggtacctaa    33840
gttctctcat tctttccctc atggttttta tcttcttttt tataccctcc ctgccacaca    33900
cagacatcaa tttgtctaat tcccaacttt atataacctt ccatttaggc tactgcagca    33960
gcttcctaac tggcttccct gctttctttt ctctctgcag caattcaccc tgcaaattgc    34020
taccagaaca gtattcccaa aacatctgtc tgtcacccag aaatcaccag taccttgttt    34080
cataaattac caggtcttta tcctcttact tcaagttctt gatggagcac cctggctgtc    34140
cggtggttag gacttggtgc tttcactgat gtgagcctgg gttcatccct ggtttcgaaa    34200
cttaagatcc tagatgccac atggcatggc caaaaaaaaa caaaaaagtc cctgacaatt    34260
tgattgaatc tcactttcca gcattaactt ccattattta cttttctgaa tccttcaccc    34320
cacctccaca gagttcccca ccatcctttg aatatgtctt acacttacct tcctgtactt    34380
ttacttggac ttttccctgt ttctttgtgc attctttaga atataactta aatttccttt    34440
tcctctttgc tcacctaaag cataccatcc cataatgatc actttcttta cactcctatt    34500
taaattctct actgtttcat agacagtgaa cagtgtttgg aattattaga tacttgatat    34560
gattttgtta cttctttcat tcttttaaaa tattttttc ttggaagatg ggagggaggt    34620
ttcagaggga gggaatataa gtatacctgt ggctgattca tgttgatgta tggcagaaac    34680
cagcacaata ttgtaaagta attatcatcc aattaaaaat aaaattaaaa aaaattttt     34740 ttcttgatt tcatctaaat tatcattctt gaaggaagag agaccgtgtt ttgtgtttct     34800
gtatattcct tgtaggacca tataattatg cttgtttata ataaaaattc ataaatattt    34860 attgattat ttcagcttgg aaatatgaag acaatgtgtg ctggttgttc aggcactata     34920
atgagtttct tccttccttt tagacataaa attttttaaa agtatctggt taccattgac    34980
cttacagtat ataggatcag cagaaatgta tattacttgc cttatttgag aaaggagcag    35040
aaaacttttt tatcatttct ttttctatat ttatgctcct tttatttaaa acctctttag    35100
ttatttgagg caactgatca tagcttccat ttttcagacc tactttcaga tatcatcaag    35160
tattcaccat tagttcttca aagttgttca tctaaagtta cagaaacttt tgactatttg    35220 tccttttctac ccgttcaaac cgtacaagga ctgctgaagg cagtgcaggt aagtcttttg    35280
```

```
actcctaagc agctcatgaa caaggttgca gtggaagtct gatgtatttc ttcataatta   35340
cgtatgtata agaaatcctg tttcccttga ttctaagaca gaaccttcta ttaaaagagc   35400
agaagcactg agctagggtt tattttccaa gtttatcccc tcttcatagt actattctct   35460
ctcctttgat tctgtttcaa gtcagtgaag taattgaaag gctcttagga aattattaat   35520
tgaagacaat agatataaag gtattcacaa ctagtttcaa tttagcatta gtattaactc   35580
ttcttattac taagtgcaat aaacattgca gcgtgtttat aaaatggaac caagctttct   35640
taagccaaat ggtgacagta ttgaatagaa atgtgctaag gctaataaac aaattgctgt   35700
ttttaacact gattcttcct cttcagccc cttctcaaag tcagcatgtc aataagagac   35760
tccttgatac ttgtccttcg gaaagccatg tttgccaggt atgtagcatc ccctgagatc   35820
ctaggaaatg acgctctcta atgttaccta aagtcctctc tgcagtcacc tctagtacag   35880
cagtcatgca aatttctaaa gcacgatcga gatgacagta ccatctccta aagggattat   35940
gagatgagta ctgtggaaag aatttgctac tttaaggata aaataccaaa ttattgtcac   36000
attgtccata ttatagtaca ctcatgggta ttcagaggag caactagtaa gcagccaaat   36060
gctgtttctc catgttgtag agcggacagt ttttgttagt cctttcccag aagcgtgtgt   36120
gataggccag cattgtatgt tgtagtctca gtgagatgaa tggtttctct ggatggaggg   36180
tttacaaggt gccaagcact gcactcctct aagtagaagg gaagtctcct ttagactcag   36240
aaaatcaaca atttcctttg ttgtttagta cttatgtttg acttatcaac tcattgtgca   36300
gcctctcagg actcttgttc tcactgccca caaaggcttg tcagcaggat agagaagagt   36360
agagatggtg tcatgaggtt aagtagataa aaacttcagc tgaattcctg tccttcctaa   36420
ttgatgtgaa cagctatgcc ttgtttagta tgtttatttt gctctgttct tcattgttaa   36480
tacacattct ttttctgtat aaaactaact ggattttct gacacaaaag cttattcctg   36540
tgaaatcagt actgtttggt aacttcttct ctgtctattc ctgagctagc cagcttgatg   36600
cccgaaaatc tgcagttgct gggttttac tgctattgaa gaacttcaaa gttttaggca   36660
gcttgtcgtc ttctcagtgc agccagtcta ttggtgttag ccaggtaagg acttttttc   36720 acaccagctt atcatgtgtg tactgatgca gtagttgatg atgtaaagat ttttttactc   36780
gggttctggt tgtacagatg atcctgaaac tgaggatctg atgatgataa tatcagccat   36840
cacttactga tggcaaattt gctgtatggt agcctctagc ttcaagttgg ctcttgaact   36900
gtatgttgat tgaaatgtgg ctagttcaaa ttgagttgtg ctgtatatat aaaacaacac   36960
actggatttt gaagacttag tgtgagataa aagtgtaaaa tatatcataa ttttttattt   37020
tgattatgtg ttgagataat attttggctg tgttgggcta agtaaaatgt taaaattaat   37080
ttcaccaatt tctttttact cttttgattt ggctattaga aaacttaata ttatatatac   37140
agcttgcatt tgtaatttgt attgtgtttc taatggacaa cactgtgcta gacactgttc   37200
tgagtgcttt acatttattt tctcatttaa ccttcacagc agttctctag gtaaatactg   37260
ttactgtcct cagtttaat agttattta tttgcacacc tgataaaacc tgtaatctaa   37320
gaaaacaaag cttttacaa taatatgata atctaggctt tgcagcagta aaattgtcat   37380
ttaaattcag tactaatatg atttgtaaat aagagacatc tgtatagcag tttcttagg   37440 aatcctttat tgctgttaca acagctcacc acttttgttt ataacttatg ccatagatta   37500
aatattagga acactggata tcatttatga atggctaata tccctatttt aaatataaga   37560
aaactgagac agagagaggt taataatttg ccctaagtga tatagccagt aaagtgtaga   37620
```

```
actaggattt gacctcagaa ggaaatggca acccactcca gtgttcttgc ctggagaatc    37680
ccagggatgg gggagctggt gggctgccgt ctatggggtc acacagagtc ggacacgact    37740
gaagtgactt agcagcagca gcagcagtat taactacctc actaagatgc ctgaaataag    37800
gattagggtt cttggtctat aattgctgaa attattatgt aaatcaaaca ggcagtatta    37860
ttctttgtca tgtccatatc taaacaaaac tacctgcctc taaacctctc aggagttcat    37920
ggaaccctca gaagagctca attctcagcc ttttaagtaa aattaagttt attatgacta    37980
ctaaattcta gtggcatgaa ataatctgtg tgccttccta agtaggtgac ttaggaatat    38040
tgtaccacat tgccaaggaa aatcttaagg aatgagtaag ttaattttt ttaagtgctt     38100 gaaaattctt attccaaaat agaataagat acttatcatg gcttgataat gattatagtg    38160
tctgcctcag ccctgggttt tgccatatgg ggaaagctaa atgtaaggtt ctttaaccaa    38220
aaataccagc tcatttact ccttaatgga actattaata cttactcagg taagatcttc     38280
atgaactgac ctctcttcct ttcaggtcca tgtggatatc catagccgtt acaattctgt    38340
tgccaatgag acctttgcc ttgagatcat ggatagtttg aagagatgct taggtcagca     38400
ggcagatgtt cgactcatgc tttatgaggt aaatcaatag ggtgaaagag atgtagtact    38460
ccactcccca actccactga tcctttaat tttaataatt tttcttacca gagtacagta     38520
gatatgctct tatttagtgc agtgaggact agtagttatt gatgcttggc caaaaattca    38580
ttgaaggtga ggaagcataa agaatagttg aaacatgtta aatgttttca tttgaaatat    38640
ttaaatgtac tgttaattta ccagccttt gttttaagga aagttctt tgcttttgag       38700 tatgaaaaat actccagatt agtcttagta gagaaatctt ctaaatgtgt ttagttttt     38760 ctgtttttag aattgtctta ccctccccc aatccatcag aaatcagttt tacagattta     38820
cttttattaa atatttccaa aatattcaac ttagttttca taaaacaac ttcttggggt     38880 tttttgtttg tgttttagt gggttttggg ttttttggc catgcttgca tgccttgtgg      38940
gatcttagtt ccctgaccag ggattgaaca cacacactca ggaatgaaag agcagagttc    39000
taaccgctga actgctaggg aattccccca gacagcttgt cattttgctc ttggtttcca    39060
acagtttaca gaatgtcttg agtagattac gtaatgacag tacaattagc aaaaaatgaa    39120
tggaacaaat attactactg acttgtaatt aggatataat tcagccagtg gaacaaaagt    39180
ctgcagtcat gggagactgc agtacaattt ctagcattta gtatgctttg tgcttcagca    39240
cacatatttt ataggatgga gaacattagg taatctagca ggtagattaa gtgcaagtca    39300
tttcagagca cagctatact ttcatttggc attttttaaaa tagcatttat tgagctactg    39360
tagttgccaa gcaccacacc tgacattgga ttttcaggt ttattgtaaa aaatatagaa      39420
agtatagaaa aaatttttt ttattattac tagtcctacc actcatatgc atacttacac     39480
aaaattggaa tcatagattt ctctagcttt ttatctctta atattatgct gtaagcattt    39540 cctatttat taaatgttct ttgccacata atttgaatg ctaaaaagtg ctctttttgt      39600
atacagtaat ttatttaact tttttttatt ttgggggcat ttttgtggct tccagttttt    39660
cactatgaat attgttgtac cacattgact gtttgacagt aatgtaccac tgtgaatgac    39720
cacattggcg ggttaaagat acaacatttt caggtctata gcatatgctg tcaagcagtg    39780
aatttttttt tttaatgatt aagaatacct tgtttaac atttgtgatg aaaaatcgca      39840
gatactcttt gcaaatgagg attagagggg aaatttctca atttaataaa aggggtctat    39900
gaatcctaca tctaatttaa atagtgagag aacttaatgc gtttctcctc tggtcaggaa    39960
caggatattt gttcacaaaa cttctgttct acattgaagt gaaggtctga tccaatgcag    40020
```

```
caaggcaaga aaaagaaata aaggcttata gatttgaaag tatgaagtaa agctgtcttg   40080
attcacatag tgtacataga ccataccaaa gagtctacaa aaaatgatat agtaaggttg   40140
tagaatacaa gatcagtaac catgtaatag tcacttatag ttctgcttac tagcaacaaa   40200
cagttcaaaa ttgaaagtag tatttatagt agatgaaaaa tacttaagga gaggttccac   40260
aaagtatatg caggatatgt acactgaaga cctcaaaata tcactgagag aaattaaaga   40320
agagttaagt aattggaaag atacgcagtg ttcacagaat agaataatca atattgtcaa   40380 tattttaag tatcagaaag atctgtaaat tgagtgaaat cccaggcttt tttggtagaa    40440
attaagaagt tgattctaca agttatatgg catgtaagca cctctaagat gaacagcaca   40500
attgaaaagt ataaagttgg tcagtagagt tttgacaaag atcccaaggt aattcaatag   40560
aaagaggata gtcttttcaa caaacaatgc tggaacaatt gtactggcgg ggggtcccc    40620 aaagccacct ctatttaaaa atttctttag gagtcataaa acagaatgta tttgttctca   40680
tggctaagat tatagttaag aatacaaagc aaaaaatagc acaagcaaga ggctcataga   40740
ggaaagtcct caggaaacca gattcctctt taagaacata aactatattg tttatacagt   40800
ttaggcacag taagcttctc attgttttgg gagttttata tcagtataag aaactgttga   40860
tcagccagat tcacagccac cagccaaagg gctaaccttt ccatggaagc ggaccttacc   40920
aaggatagca gtctcagact actaagttaa ctcttctcca cagtcatctg tattaaaaag   40980
aagaaatcct caacccttat ttagctccca atttaaaaaa ttactttgta atgtctcgta   41040
gtcctaaatc tgttaggata ttggtattca tttattcatc aaagacttaa gttagtactt   41100
ttgatttgta aaaaactcta cgtattatta acataaatac cttttgtcat acttgttgta   41160
agtacaggcc agattgccat ttgctttttt tttttaatg ataatcattt tagagctaga    41220
aatttagatt ttacagtttg gttgtaatct tcacctttga gatacctact gtctcttttg   41280
tgtggagtcc atatccttcc agtgaatatt tactagcatt ttcttttatt ttttttaatg   41340
cttttgttta actaaattct tctgcagttt ttatattaat atataaagac ccaactcctc   41400
cgagattagc catttctttt ttcaggtata atatattgcc tctttcatgt gtactgagtc   41460
tttctgtttg tatgctatgc ctttattttt ctgtaatttt tgtgccagga acacagttgt   41520
ctttttatta ccattatact tttataaaat atcctaatac ttattagggc tgatcatcct   41580
ttgtttttta aaaaaaaat ggggggggt ggtcaattct cattttctgt ttctcactgg     41640
tagactgtat aacctctgtc tcaggttcca aaaagaaaag cgtccccagg attttaatct   41700
gagcagtttt aaactaagac tgggaaattt tggatgggaa gaaatgtcat agtcattcac   41760
attagggtgc ttaggtccag gaggcacttt tgaatcactg gagagtaggg gagtgcccta   41820
aaaaggaagg ctgctaatgt atgataagag gaaaaaatga ggtctgggaa agggaaaagt   41880
accccaaagc cagacgagac ctgatgtcta acagttgtga ggattatggt cagtttataa   41940
tccagttctc attgtcagag atctcacatt agcgtaggcc aataacctaa actttctgaa   42000
ttgtttctcc ctctagcata tacggcctcc atcttttttt cagagagctg agaataggta   42060
aagaaacaca aagttatttt aaagttaaga ttgtgcaaat cactagtgac tctgatagag   42120
agcttatttg tcctctgatt ccttttaggg gttctatgat gtccttcgaa ggaattctca   42180
gctggctaac tcagtcatgc aaactctgct ctcacaggta aattatattt tcatggatat   42240
aagggaacag gtaccaaggc attaagtaat tgacattttt aataatttc aaaatataaa    42300 ataattccta agtagtccac tggtacgttg taaacatgcc tagggtacat gatgctattt   42360
```

```
catgttgttt tattttaatc actgtttatc tgtctaccat attgccattg tctgacaatt    42420
aaccttctca gttaacatcc taagtcagaa gggcattttg tagaaccatt tatacaaagg    42480
ccatcagtag tagtatctgt tatgtttatt tctgataaag aagagtgatt tggagaaaac    42540
agtaaaatat tgacatttct caaatctgag tgacatattc atgagtgtct cttaggttat    42600
tttctatatt tctcagcttt tttaaaaagc tgcaaattat gaaatatttc aaaggaccat    42660
caagatgaga agaatttagc tgaagagttt ctaatgtgaa taagacccttt ttactctcag    42720
catttattat taagcattta tttgaattag tgaattcaca aagtgcaacc atcaccagtc    42780
aattgagaac gttttatctt ctcataaaaa accacaccgt ttagctaccc cccccttttaa   42840
ttttcccatc cttcctcaaa ccttctaccc ctaagcaatc atcagtctta tttttctctc    42900
tatagatttg cctattctgg acatttcata aatagagtc aaacaatgtg tggtctttta    42960
tgactgactt ctttcactta acatgatgtt ttcaggggtc atccatattg tagggtgcat    43020
cagtctttat tccttttat ggctaaataa tatttcattg tatgatatat atatatttt     43080
tttttaatat atgttgagag agttcaagag actattatgt actaatagta ataacaacag    43140
tacttaatgt ttagcactta cagaggggca agcaatttat gaatggtata tggtggatga    43200
tctcatttag tcctcacaaa accctgtgaa ataactgctt agttccattt tacagatgta    43260
tgttttaagg ctccaagagg ttaagtaatt taatttgccc aaggtctcac agttaataag    43320
tgatggagct agaatttgaa ctcagatctg gctcaagagc tgaagcatgt gtttctccta    43380
tttggagttg attaagctat ttgaatcttt taagttgatg cttgtcacca aatttgagaa    43440
atgtccattc attatttcat cagattattt tttcctatcc cctctttctc tcctttctt    43500
ctggggcttc agtggtatgt atattggaat gcctgatact gttccacaga tcttggttca    43560
ttttcctca atatttttac actgttttct tcagatttta tattttctca taatctgtct    43620
tcaagtttac tttcttctgc catttcagtt ctgttgtttt actcttgaat gcatgttaaa    43680
ttttatcaga tgtttttctg tatctattga gatgaccata tgattttct ccttaatct     43740
gttaccgtga tgaattatat tatttgatct tttaaaaaaa cattgcattc ctagaataaa    43800
ctcaaattga ttatattacc ttttttatac actactgggt ttgatttcca tttaggacat    43860
acatacatct gtacaagaag gaatggccta taattttcat ttttcatact gaatttcttt    43920
ggtttagtat gagcttagta aaatgattgg ggatgttccc tctttttctg gttttttgtaa    43980
aatttgaaat ttcctttatt ccatttcccc ccttacttgt ttcaaagtta aacactttct    44040
ttaaactttc agctatattg tctaatgatt tggacagtct taactctaaa ataacctat     44100
atttgaagtc atgtgaattc tagcctcagc taactaactt atggttagaa agtccctgag    44160
aagactttc ccccttcacc tgaagtcaga ggtaggtagg taagtacata tccctcact     44220
atcttcctcc atgtggtgga tttatttttt aggttcatcc actaaggata tctgcttttg    44280
agaattccag ctttctgtga aggtctctga tacaatctca gatacaatct ctgatacaat    44340
ctagatataa tctctgatac aaccccatgc ggaccctagg ctctgtcttt aatttcatga    44400
tttcttttac tttcctttta tcttagctat ctatttaata aatgtatcta tataaaaatt    44460
ttaatgcagt gttttttatt ctttactgcg agggtttctc taaacccctag cccacccttt   44520
tgctataaat ggtacttctc gtcccctctc gctcttcctc ctttttttatg ccgttgcttt   44580
gtgctaattc tgctaaagaa gctccatttg gaagtggaga atgattgga aggtcttaca     44640
ctatcaaaag ttttcagtg gaccttggac ctgatcttat ataaaattta tatcttgtta    44700
tatttatct ttcaaactaa tgatcagtcc atctacattt gcacattaac atggcaagtt    44760
```

```
atgactgaaa gcatagagca gtgcttccca actcaggtta gtatgtggac caataaaatt    44820
atatagactc caaaagttaa aaagaggaaa atggcaatta acattttttt ttatgaaagt    44880
atagttgatt tgcagtgtat ttgtttctgg tatacagcaa agttattcag ttacatatat    44940
attctttttc attatgagtt attacagtat attcaatata attccctgtg ctatacactg    45000
ggatcttatt tatctatttt atatataata gtttgtttct gctaatccaa aagtcctaat    45060
ttatcctttc cccaccccct ttcccttttg ataaccataa gtttgttttc tgggtctgtg    45120
aatctatttc tattttgtaa ataagtttta tttgtatcat tttaaagatt ccacatataa    45180
gtgatatcat atagtatttg tctttctcag ttgacttcac ttagtatggt catctccagg    45240
tccatctatt ttgctgtaaa tggcatcatt tgattctttt ttatggctga gttaactaac    45300 ttttttttgag ctctgttatg tgctaaatag tatttgaagc tccttacatg tgttagcaca    45360
tttaatcgta tacaaatgtt tatgcttata ttaataatat cctcatttca cagatgagga    45420
accaagacat ctacctttct tgaattaata agtagtggta ctgggatttt agattcagtc    45480
agtctgactc tggagcctct attcttatta accaagctgt actgaaagtg cttgatagcc    45540
tatacaaatt aaggaactgg tgtgagagag catggtgttt taggagag gtgatgaagt    45600 ggactaggaa aggtgtcagt cagtgcactg cctgatgcaa gggcaaagga aggacagggt    45660
tgagccaaag caacagattt tcctgcagtg ttctttggac agttgggaaa caatgtctta    45720
gaaagcatta acattaaag ttgccattag cttgaccagt taaaaaagtg aaaagcattc    45780
atgaaccgtg atgtctttt ctttcccata cacagttgaa acagttctat gagccagaac    45840
ctgatgtact gcctcctctg aaattagaag cttgtattct gacccaagga gatcaggtct    45900
ttctacagga accactggtg agccattctt tcctcctccc ataaccatta tttttactct    45960
taagtaaaac taccagccct attgatatgg ttgagcttca gaaagagatg acttctctgt    46020
gaaacacctg gtactcccag tgaatttta ctcttgactc ttccctgacc catcaccacc    46080
ttggttctgg tggtgagata tctgcatatc aacacttgac taataatcaa ggcatctatc    46140
acttctccca aggagcattt tacctcccat taatggctct ttgattgcaa gtactaaaca    46200
gatatacttt agaattggaa gaaggaggtt acccagaagc aggtgaaccc aggcgatctg    46260
cttcattagt ctggagtgta tgatttaggc tgagctagaa ctggcattct gttgaacctt    46320
cagagaaact gggacagttg ttttctatt ctcatctagc gggaagaaag aaactgaaac    46380
tcctgagtga cttacaacag atgtcctcag cctagagaga agctatggtg gtctcccaaa    46440 gattcccta acctaaatcc atatgtttgg aatagccttt gggactcaaa ggtgctgctg    46500
ctgctgagtc acttcagtcg tgtctgactc tgcatgaccc catagacagt agcccaccag    46560
gctcccttgt ccctgggatt ctccaggcaa gaacactgga gtgggctgcc atttccttca    46620
ccagtgtgtg aaagtgaaag tgaagttgct cagtcatgcc cgactcagtg accccatgga    46680
ctgcagccta ccaggctcct ccatccatgg gatttttccag gcaaaggtgc tggagaggat    46740
ttaatttcac aacctggctc cttggtattt gtaccagatc agagatagca catttgatgt    46800
tacattctta ggtgtcagct acttgtgaaa ccactgtctt tgggaaaggc cagaaaacaa    46860
tgcctctgtt agttccattc ttttttttctg ttttgttttg ttttaactc cagattgact    46920 taatttgtga tgctaatgaa taactttatt tagccttata gataaggatt atttgtcagt    46980
tatcaacagt ttgataggtt atcctttaac aagaatattc agttattatc tttttcttcta    47040 caggattatc tgctatgttg tattcaacac tgtttggcct ggtataagag cagagtggta    47100
```

```
ccattacagc aagaagaaga ggaggaggaa gagggggttct accaatactt agatgatatg   47160
ttggagtcga ttacgaatag aatgattaag agtgaactag aggacttcga actggtaatt   47220
gctaagtcta agctgtgttg agtaatggag gttttttagta gcttactaat ttttatcttg  47280
tgtcttttag gacaaatcag cagacttttc tcagagcact ggtattggca tcaaaaataa   47340
tatctgcgct tctcttgtta tgggaatttg tgaggttcta atagaatata atttcttcat   47400
aagtaatttc aggtagggta tactctaact ctacttgtag ttcattttgt gtgtgggagt   47460
gtgttttctt aacactaaca ataggctagg tatgaacaga ctacagcgca tgacactctt   47520
agatggacct ctagcctaag accaaactat gttctttcta ccagggaaca tccaagcaca   47580
tgccaaacag gctcgtgaat tttgtctctc catcaggctt tactttactg aacattcccc   47640
agaccttgaa cataacaacc cctgatttta atagagaaat tttgattggt ggtagtattg   47700
aactttcatt ctctgcaatg actgatacaa ataaggggg aaaagaaatg acccagttgg    47760
gtattaccta ggagtactgt gttaatagtg aagatcgatt catttgtaat attgggtcta   47820
aagtatgaca tctaaagaag tattgtgatt tccttattac tgtcttgaaa gtaaaccata   47880
atattctgat gcctgtcctt ggtggactct ttccttttat acagtaagac taagtttgaa   47940
acaattctga gcttatttat gtgttacaag aagctctccg acatccttaa tgaaaaatct   48000
ggtaaaggca aaacaaaaat ggccaaccga ccaaccgata gttttttgtc catgaaattt   48060
gtgtctgatc ttctcacagc tcttttcagg taaggttcta acacagggct taaagacagc   48120
cttaaggtga gggttaaaaa cacctactga gggtcactga tattacctag tttggattca   48180
caattcttag catatataca gtaaaaagta agtcaacggg gttgtaattt tcttgaaagc   48240
agaacacata ggcatttaaa gagatgcttt gaattactaa agggaacatc agaaacagtg   48300
aactagtgga tgaaaagata ggatagattc caagaaatca acctaagtag catgaaaaga   48360
agggaaagaa aagcttgaat ttaaaaaaaa aggtgggggt gacaacaaaa aaaacattac   48420
agaaagttaa ctaagactga cctttaaatt tcatcaaagt taaaggattg agggaaggg   48480
gagaaaggga ggtaacgctg agaataatat ttgtagaaag acagccttgg cagtgactct   48540
tggtgtgggc tgcctggagt ctgtcttta gaactggctg ggtgctattg tgaactgtcc    48600
ctagaaaacg taatttcaag tcccagtagc aggggaatct ttctgtctct ttttcctgt    48660
ctagggacag tacccagagt catgaagaga gcctgtctgt tctgaggtcc agcaatgagt   48720
tcatgcgcta cgcagtgaat gtggctctga tgaaggtcca gcagctaaag gaaacagggc   48780
atgtgagtgg ccctgatggc caaaacccag agaaggtctt tcagaacctc tgtgacataa   48840
ctcggtaagc cccacacacc cttagagacc tgttccactt gctgtggcat ctccaagaga   48900
ggaaatcgac gacgggggtg gggagagaaa ggtggtttga agtttgggtag ggagaaaggt   48960
ggtttgaagt tcggcatacc caaaggtgga agtgcagtca ctcactatgt tggggttttt   49020
tcctagtcct gtttttggtgt ggattgttgg ccacatataa aatgttaatc taataccagg   49080
aataaaaagg gatattacat aatgactaaa taattcatca agcagacaga acagttttaa   49140
atgtatatgt acttaatagc acctaataac agcttcagaa tacttaaggc aaaaatggta   49200
atactgaggg agaaatacac aaataataat ctacctctct cagtaatcag tagaattaga   49260
tagaaaatca gaaaggatgt agaagactcg aacaacacta tcatccagct tgactttaat   49320
caatatttat agaacattaa ataagtattt aagatagtga gttattgcca gaatcagtgg   49380
aacagatggt tcagaactga tctacacaag tatggtcttg acttttgaca aaggtgccaa   49440
ggcaatggaa tggagaaaga aaagtctttt caaacaggtg tttctggaac aattgtacag   49500
```

```
gaatatgtga aaaaatgaaa ttaaaagaca ctgtttggaa gaaaagctat gcccaaccta   49560
gacagcatat taaaaagcag agacatgact atgccaataa aagtctgtct agtcaaagct   49620
acggtttttc tagtagtcat gtatggatgt gagagctgag ctataaagaa agctgagtgc   49680
caaagaattg atgcttttga atcagttggt gtgttgaaga agactcttga gagtcccttg   49740
gactgcaaga tcaaaccagt ccgtcctaaa ggaaaccagt cctgaatatc cattggaagg   49800
actgatgctg aagctgaaac tccaatactt tggccatctg atgtgaagaa ctgactcatt   49860
tgaaaagacc ctgatactgg gaaagattga aggcaggaag agaagggaa gacaggatgt    49920 gatgtttgga tggcatcacc gacttgatgg atatgagttt gtgcaagctc tgggagttgg   49980
tgatggacag ggaagcctag catgctgcaa tctatggggt cacaaagagt cagacacgac   50040
tgagcgactg atgtgaaaaa aaattgaact ttgatccatt tctcatgtta taaccaaata   50100
ttgaaatgaa tcagaggcat aagtataaaa ccaaatattg taaaacatct agaagacaga   50160 aaaacccttta caaccttgtt ttaggtaaaa aatttcctag gtataatacc agaagcacaa   50220
tcaatatttt ttttaaattt aactctgttc cttgaaaaac attcctaagg aaatttaaag   50280
acaagccaca aattaacagg aaatatttgc aaaacacgtg tctgatgatg gactggtaac   50340
cagagtatat aaagaactca aacttgttaa gaaaacaatc aaattgagaa aatggataaa   50400
gtgttttaac agacacttta ccaaataaga tatatagatg gcaaataaga acatgaaagg   50460
gtgatcaaca taattagtca ctaggttagt gcaaattaaa atcacaatga gatatcacta   50520
aacacctaat ttttttcctt ttaaaaattt acttatttgt tttaattgga ggctaattac   50580
tttacaatat tgtggtggtt tgccatacat tcacatgaat cagccatgag tgtacatgtg   50640
ttccccatcc tgaaccgccc cccctccccc tatcccatcc ctcaaggtca tcccagtgca   50700
ccagccctga gcaccctgtc tcatgcatcg aacctggact ggcgatctat ttcacatatg   50760
ataatacaca tgattcaatg ctgttctctc aaatcatccc accttgcct tttcccacag    50820 agttcaaaag tctgttcttt atatctgtat cttttttgct gtctcacata tagggtcact   50880
gttaccatct ttctaaattc catatatatg cgttaatata ctggattggt gttttctttt   50940
ctgacttact tcactctata ataggctcca gtttcatcca cctcattaga actgattcaa   51000
atgcattctt tttaatagct gaataatatt ccattgtata tatgtaccac agctttctta   51060
tccatttgtc tgccgatgga catctaggtt gtttctttgt cctggctatt gtaaacagtg   51120
ctgcgatgaa cattggggta cacgtgtctc tttcaattct ggtttcctca atgtaaacac   51180
ctattaaaat gcctaaaagt ttagattgac ataccaaag tgttgtcatg gatgtggaag    51240
aatttaaact ctttgttttt tggtttttaa tgtttattta tgtatttatt tttggctacc   51300
ctgggtcttc ttgctgtgcg ggcttttctc tagttgagtg agaggggggct actctagttg   51360 aggtacacgg gcttctcgtt gccgtggctt ctcatgttgt agaggacggg ctcttgagca   51420
cacaggcttc agtagttgca gctccgggct ctagagcaca ggctcaagta gttagttgct   51480
ccactgtatg tagaatcttc taagatcagg gatcaaaccc aggtctcctg attggtaggt   51540
ggattcttta ccactaagcc tccagggatg cccagaattt aaactctgat acactgttga   51600
cataaatgta aaatggtgca gccactttgg aaaataattt gtcagtttct taaaaagtta   51660
agcacacacc tatcttacgg tacacccatt ccactcttag gtatttacct aaaagaaatg   51720
aaagcagatg ttttttataaa agtttgtata tagtagtttt acctgtaata gcaaaatctg   51780
gaaacaacct aaagatgata aatcggtgac tatgcaatct gtggcgtatt catacctgg    51840
```

```
aatactgctc agcagtgaaa tgcgacaggc tgccagtacg tgcaacaaca gacgtgaacc    51900
tcagagctac atgctgttag caaagccgga cttcaaaagc tacagaatga atgataccat    51960
tcttatatga tagtttgtga attgtaaaac cgctgggaca ggaaacagat cggtggttgc    52020
ctgggaaatc aaagagaaag aactgactgc aaaggagcac atgagaactt ttggggtgat    52080
ggaaatacct agattgaggg ggatgagtac acaactgtgg aagtgagtca gcagagccat    52140
acagttacag gatgggaatt ttactgtatg taaattgtat ctcagtgaac ttgactttaa    52200
aaatcacttt tccccagggt cttgctttgg agatacactt caatccctac ctcagtggaa    52260
gagtcgggaa agagagagaa aggaaagaac atctcgctgc tgtgcttgga gggcatacag    52320
aagatactca gtgccgtgca gcagttctac cagcccaagt gtcatcagtt tctcaaggct    52380
ctgggtgggc atttcagttt tgataacttg gctcgatctg agtttctctt tctcaaccaa    52440
acctctcaat tccagttgtt agcccagcag aggacacctg cgaagagtcc cagtgtggct    52500
aaggagtgac atctagtgga ttcagaatcg gcacttactg gattccattt aaccacagat    52560
gggactggga aactgaatat agccttaaga agctgctgaa tgttaggaat ataattaaag    52620
ctgcctccag gcttttttgg cctcctaaaa ttttagcttg gcaaaaaaaa ataaccaagc    52680 cccttttcaaa gcagatagcg ttcttttcct tttcctagat gccacagata aggaggaaga    52740
agaggaggaa gtcagtgtca gtgagagagc agctttccag atccgtcagt ttcaggtgag    52800
acacctagga gactgctgtg agggtcctca gaaagggact gttaccaggc cagctgggaa    52860
caggcagacc gtccacaagt aggacagcag ttttttcctgg gtcatcattc aggcaacttg    52920
acagctctga gaatgaaagg taatgcattt aaaagcatca ttcaaggaag gatgtgtgtc    52980
aagccacccc aatctacagc actcattgcc tctaagaatc actgagctga tattatacaa    53040
agagctggcc aggagcccac tcgtgcaggg agtgtaactt ggctttgtct gtcagatggt    53100
tctaaccact agctgtcacg tatcaggatc ttttatccca gaggatttct ttaatgttcg    53160
tatcatgtgc caggaactgt tcaggtgctg aagttctagc aagaaataag agacaaaacc    53220
ctaccctcac atagcttaca tagtgggaag agactgacgg accaaagaca gtgttttggg    53280
tggtgagaga ggaacaaaga aaaggaaat ggacagtgtg tagggaatgc cagtgctggg    53340
gtatggtcta gccctcaggt cagtgaatgg gcctcaggaa gttgtgaacc acccaggcga    53400
tcagtggttg ggacacagca cttttcattgg gcccgtgttc tgtcccttgt tagggaacta    53460
agatcccaca agctgtgtgg tgcagcctaa aataaacaaa actgggtgca cagttcattc    53520
ctaatgtaca tgtggcaggg gtttgaggag tccatagcgc tcaagagaac actcagacgt    53580
ctgatcacaa aagggtagga gactacctgc tcaatccagg tcttatttcc agattttatc    53640
ctcttggatt tttggtattt ttgagtcatt tctgtcccag ccttaggaat ctctggctgg    53700
atgtctcttc tctttgctag tatcatgtct gctaatgttt ctgtgtgtcc tttctcagag    53760
gtccttgttg aatttactta gcagccaaga ggaagacttt aagagcaaag aagccctgct    53820
tctggccact gttctcacca gcttgtccaa gctgctgaag cccatctctg ctgaggtatg    53880
agcaccaatc agtcccactc tgcatccccc agaaggccag aatactacat cttacagtgt    53940
acaactaaat gtcctcttga aatctggctt atttaaaatc atgtatccag ttatgctcct    54000
gaattaatat aagatctgta agatgtacct ccacccaccc ctgccccgta catagtgttt    54060
ctaccatgac gtagttaact gcttttgttt atttggccac tgtcaagggt aaacaataag    54120
cactgtaaaa aaaaaaaaaa gtcttgttta tctgtggggc cttcaacctt cttgtgtttc    54180 cctacccccct tctaagatga aagtatgtta attatcaagg tagctgacat tcagcagtta    54240
```

```
accttctcat caaaattagc tgattctgag tttggggggat attcaacaaa aggtgataag    54300
tcagaaagca taattatagt cctaaaagag aatctgttct acccagatag attttaggta    54360
tatgtgcttg ggtttgcaca tgtacacgaa gaatatatgt acccacatga gcattcacac    54420
atgtgcaata agagaagcca tattctgtgg gtttgttcca ttcaggagta atttccctaa    54480
aggatgataa agagagttct tgagactagg gctgtgtggt cctcccacat ctatttcctg    54540
acctgtgggg agacaagttg agagtgctga ggtgcaggcc tccttgtgta agcccttgct    54600
tttaggaaga gctagccaga ctatagcctg gaatgttacg acatttgagc actgaaaaag    54660
caaacttcat tttcttgttg tcttagttcc aggtagccca agaaaatcc ccattgctac     54720 ttatttcatc ctagatcgga acaacgcatc cccactttac tttcagcttc attctttcat    54780
attgctactt ttgctgcaag gagcccaaga ctaggaaaga aacacaggga attggaacat    54840
ggggacagtt gaaggaaaat agatttggaa aggctaatat aaagaagaaa tttttaaaat    54900
tttaccaccc cctcataatt tcgggtagtg tgtctaaaat tttttaattt aactttgaat    54960
gggtaataaa gttcaatgat ttgaaaacca gacattataa aaaatttgc aggaaatggt     55020 cacctttcta tccgtgtcct ccatctgttc agttcttctc ccccagtagc taaatatctt    55080
ttagtgtctt gtgtaaagaa ttcttttatt cctgtacagc aatatgaata tagcttctta    55140
tgctcaaccc tacctcttc acacaaaagc ttttttcagca tcctgcttta tttatttatt     55200
acatttaaca ctgtattctg gacatctgta ttctacagta atcactgtat tctgggaaat    55260 attttttatat cagttcacag agaattttca tttagcctct gaagtttttt ttccctgaca    55320
gatcaaaacc tgaattctta ctggtcattt tacctttaaa catcactgca tttcagtgtc    55380
ttggtggcta gaagcctatc ccaaataact gctgaagcag aaagctgagt gtgtgtctag    55440
tgaaacatga cctactagtc caaggcctta agcttcccca actctttttct tttgccccctt    55500 ttcttttttt tccccctgct ccctttttaac ctcctgtggc ctcttggttc ctaaaggcta    55560
atttgactgt cactgtggcc aggatcttat tctcctatgc ctctattagc ttagtattct    55620
taaagatgtc tcagatgcag agagtgctgg gcatgggaag aggaagaagg gcactttagc    55680
cccaaactgt ggtgggaggg gccagggaag ctcaaataac agcccagacc ccaggacctt    55740
tggcccttaa tgagggcatt tgagaattga atcataggct atatttaaga aaagaatcag    55800
taattcagct cgtaactttg gacttacttt tatgctgttt ttcagtagag taccacttta    55860
gatccaggca tatgttttag taggtgattt gtttagactt gcaaaggcct agagctctct    55920
tagtctgata gcacctaggt ctgtcttttg aatgtttcta taatatccta atgatctcca    55980
gtttgtgcag atgttatcct ggacatctaa gatttgcacg gaaaacagtt gcggtaagtt    56040
tcctgccata tttcctttt caggtttata taaaatcatc agcaccaaac aacatttaga     56100
aaattacaca ttcaccggag tatccaaaac ttcaaataca caaaaccagc cccaagggtt    56160
ggtaagaata cagtgcagtt gaacctctca ttcactgctg ctggaggtgt cagttggtat    56220
aaccactctg ggaaattatt tagcaatact taactactaa aattaaacat aggcttacga    56280
tcaagcagtt ccactcccag cataagcagg tgggaaaatt ctcacagcag tactgttcta    56340
ataggcaaaa ccaaacccag acgtctgtca gcagtcaaat gggtcgaggg gttgcactgt    56400
gcgcgcagtg ggacactgga cggcggtggg agtgaacaga ctccactgac acgtgacatg    56460
gaggagtccg gcgcacacga cactcagcag atggcagaca cagacagagg acttactgca    56520
tggtgctact tagatcgagt tcaaaatcag acaaaactcg atatgaggtt acaaggcaga    56580
```

```
atgacagttt ccttggtgag gaggggagtg tcctggggtg ctgatatttc ttgacccgta   56640
tgctagttat atgttgacag tgactaataa atgggaaaca tccccctcat ttgcacctgt   56700
gggtcgaagt gtacctttgt ggacccgctg cctgggttgg agtgtgtgca gcatggggat   56760
gttgtgcctg aaacatgaca ggctagcatt ccagccaggc cacccccacc cgctacagga   56820
ctgacttggg ttataactga gttttctttc cttcctactc ctagaggatg cctccttttg   56880
caagggcatg ctgagtttgc tcttcaacct ccatgtttcg tgtaagagtc ctgttggtct   56940
gctgcgtgac ttgtcccagg atatccatgg acttcttgga gacatagacg aggtactgta   57000
gtgagccttc agtatggagc cctgagttgg gagtagaggc caggggaaca gccttactgt   57060
cattacatct cacctctctt tccgttccca ggatgtggaa gtggagaaaa caaacaactt   57120
tgcattggtg aatttgaaaa cagctgcccc tactgtctgt gtaagtgttg atccctggca   57180
cttgggaaat agccttgtca tcccttccat tttattccct gtgaggagtg aattacagtg   57240
gctaaagtcc tgaggcctct aacccgccca ctggtggccg tggctatcat gttacaccag   57300
cagctgtgtg cagtgagcca tgccaggcgt ttttttcttt cacagctgct tgttctgagt   57360
aaagctgaga aggtcctaga agaagtggac tggctgatca ccaagcttaa gggacaagca   57420
aatcaaaaaa tcataccagg taacatgggt tgagggaggg gttccaggaa ttgtgatcaa   57480
agcaaagcca actaaaacct gaactggaag agacataaag gcagagcccc tgagctctgt   57540
ctgtttgttt gtgctagact tcctaagtaa tgaaagtaga agatataatt attaatgtat   57600
tctgcatcca gacttcctag ttaatgatgt ttagttggtt tctaaatctc tttgacttga   57660
actagaaaat aaggtcagtt gggtttgaat gtgctaatta acttcatttc ctttcagaag   57720
aggcctcttc tcaggcagcc ctaacaaacc atcccatgga gaaaaccacc atcatacagt   57780
tgggaactct gctcacattt ttccacgagc tggtgcagac agccctgcca tcaggcagct   57840
gtgtggacac cttgttaaag gaccttggca aaatgtacac cactcttaca gcacttgtca   57900
aatatgtgag tatcggagag tcagtcacca ccatcattct gccccaccca gccaggacac   57960
tgcccctggt gctgaacacc ccagggcaga acccatgtct acatctctgc aagtcacagt   58020
ttgaccagta gatggcaggt gactccacag gcctggaaat aacagttgag gcataattct   58080
aaatctgttt ttagagctcc atatttcttt agcatatgag catgttgctc atatgattga   58140
gtataatgaa tgtaaatgcc tcttaattga gtataattga gtataaatgc cttttcaaac   58200
accttctaag actcagtcta aactttagct atagaattta atctgattcc aattacacaa   58260
aaagttagac aatttcagac cagtctggac accgaaaggg tatttgtcct ttaacaagta   58320
ggtgttaaat gcctcacagg tcaggtacac gagtagggaa taagtttatt ttttgaaaat   58380
acaaggtata cttgccctga gtttaagtta atgcttctta gtatccgtta acaagaaact   58440
ttttttgtat ttgcagtatt ttgattctca gcagacattc aagagtgcta ggaactacgt   58500
aatttagatc cgattctagc aatgacccac attacttagg aaggcacgga caaccaagda   58560
aagatggtgg accgcctcac accatgtacc caaacagcag cgctgccatt tctgagaagg   58620
tgccgctctg gctatagtgt gtggctaact agcttctgtg gtagaaatac ggagaacctc   58680
tataatcttt attggctttt tctaaaagaa aaacagcaaa gtcattggct ttctagattc   58740
agggactatc accctgaagg atttttaaag caataaatgg aacaagtcag aaacttaaat   58800
ctttcattgc ctcctgtctg ggaagctttg gagcttaggg gagggaaaaa aggaagcctg   58860
gagtcttaag attctgcacg aatctgggta gcttattttc ttttcctctc tccagccaga   58920
gcaatagtca tacaccatgt gctcactgag tcactacctg tagtttcatg ggacatctgt   58980
```

```
gtaggaatag cattctaaat ctggattccc aggtggctca gtgataaaga atctgcctgc  59040
caatgcagga aacgtacgag atgcaggttc aatccctggg ttggaaagta tcccccaggg  59100
taggtaatgg caacccactc cagtattctt gcctgggaaa tcccatggat ggaggagcct  59160
ggtgggcgac agtccatagg gtcacagagt tggacatgac tgagtatgca tgcatgtaag  59220
attccaacgc tttcccctag aactttatga aacctttgag agaagtgggt gtcctgccat  59280
tgcctaatac tgaatcttgg aatcttttgt tagtatctcc aggtgtatca gccctccaca  59340
ggaattccga aaaatatgga aaaactggtg agttgagaat gcctttccta ggaatgggga  59400
aagcatctta ttcctacagt tactgaattc tttctccttt gctgcaggtg aagctgtctg  59460
gttcacatct gaccccctcta tgctattcgt ttatttctta tgtacaggta agtgattgtc  59520
tgtatcacag tgtatcttca agtgagaaag gactccttgt attcccaggg gactgatcac  59580
taagtttgat ttagagagaa aaagtgtttg gtatgcttgc acttggagca gaggagaaac  59640
atgcatcctt aggctcagtg acttggtcta tttctgggtg attccaaacc cactcctttg  59700
ggaatgtgag tgaagtagta gcaggcatgg tgaggctaaa tgaggtaact tgtggaaagt  59760
gcttaacaca acaccaggca ggtgttctct aaatatttgc tgttccaata aaatgaacat  59820
gaccttagag catcatttcc caagctgtca gacataaggc caaaaacaga aaggttaaga  59880
ttccgagctt ctgatatagg gggcgtgggt ttgatcactg gttggggaac taacatccca  59940
cgtgctgtgt ggtacggcca gaaaaagggg caaagctgag gttcgaactg ggttctttga  60000
ctccgtgaca gtggtctgca aactttctgc aaagggccag atggtaaatg ctctgggttt  60060
tgcaggccat agagtcactg tcacaactca actctgccgt tgtggaataa aagcacccat  60120
agtcaatata caatgaagga gcttggctgt gttcagtgaa acttctgaaa acaagcagg   60180 agctggattt ggcctcttgg ttgtagttgg ccagcccctg ctctggaagc atacttgaca  60240
ctcactgact tgtaaaatgc tgggaggttt ggggttttgt gtttgaccca ttctcaagct  60300
tttcttctgc ttatcactag gcaccttcca gactatcttt ttttctacat tacacaaaaa  60360
ctggtttatg tattcttcct tggatatttc tcccttctc aatctgtgtt tgacttaaag  60420
ccttatttga caaatcagct gatccacagg cacttttgt ctttgtgaga tgtgcttaat   60480
gagtcaagag cccaaggttc cattaactct ctccaacttt tatctagaaa tctggattgc  60540
atttgccaca tctttcaaag agctgcttat tctcttttag ctccttttt cccatagcct   60600 tggatctcag tgagaagaaa gcagtgaaag ccattgctcc aaaacccgta gcttagcatc  60660
ctgctcagga ctgtatacct ttaaaagata cttctcttcc cactacagtt ttagtcctgc  60720
ctgaatcagc agaaacaggc catagctggg attgatttag ggagtttcaa caaggtccca  60780
tctggggtac aacttttagg aagatggctc acttcccatt tggtcacatg agttctacta  60840
cctgtgctgc ttctctgccc ctcccctaca aagtattcac cctctaccct gccttccagg  60900
gccaaaaata agtttcttca caccagcatc tctgggatcc ctacattttc ttattttcca  60960
gaacatgcca tgtgaaccaa gcctcctctc tctcacatgg ctgtagtagt gtgatttctc  61020
tctgtttgca ggcctctgtt tttaactgtt agttgtccca tgggccgtgg tctgtcattc  61080
ctagagggca cagaactccc cttcaagtaa aaggttcctg tttgtgtgcc tcacacttgg  61140
gtggtctctg cctcacgtgt cccttctctc ctgccttatc agaatcctgt acttcctggt  61200 cccccttcttg attgttcctt tctccaggag ccctttattt tgattatctg caacataggg  61260
aaacaaagtg tttctatgac ctttaaaccg tcctggagcc tgtaaccact tgtcatgtga  61320
```

```
gacacatggc tctgagaaca acctctccag cttcctatct tttctctagc ccttttagcg    61380
aatatcccag tagtgaacac ctagtcctac tccccccttg acagttcttt gtagctcatg    61440
agtcccttgg ctgccctagt gttaataacg gtgggtccta acctcacttc cctgtgatag    61500
acccatccaa gagcaagact gtaaatctcc caacaacaaa aagcgggaaa atatctgagg    61560
attatgaagt gtcccagaat gtttcccatt gcccagcatc tgcttcagga gaatctcttc    61620
acccagactt ggcccctaa gagttctccc gttatcgcta taatcatcgt attagaaaat     61680
taccactagc ctggtagctc tacagaaaaa ccttcaggaa tgagagaact tgtttccttt    61740
tctttagaac aagcacagta ggagcctaaa atgtaccgga gaaaggaga aaaccgctgc     61800 cggccccaca gccatcgtaa gttgctgaca gtgaccaaga cgtggccact gggaattccc    61860
tggtggtcca gtggttggga ctctgcgctt ccactgcagg ggggcaccag tttgatccct    61920
ggtcaaggaa ctaggatcct gcatgccgtg cagtacaaca aaaaaaaaaa ggttgctaat    61980
gaaccttgaa aatacgttaa gtaaaagaag ccagtcggac aaagactagg tgttatatga    62040
atccatttat ataaaatgcc cagaaaaggc aaatctaaaa agattagtgg ttgcctagaa    62100
ctggggagca ggagtggtta gggggatgtt agagaaactg ggaaggtgcc tgctaaaatg    62160
ggtataggat ttcttgtgca ggtgggttgt gtgaaaatgc tgtaaaatta tggtgatggt    62220
tatacaactc tgtgaatgca caaagaaaca cacacaaaaa agcatgcaat ataatgggta    62280
aatggctggt atgtgaatta catctcagta aagctgggga aaatgtgctt atttgtgtat    62340
ggctgcttct caactcatgg actttgttca aatggaacat cttttcctc tgtatatgct     62400 ctattcagga agtaccagga aatcttgaac tcttcaaaaa tagaaatagc ttaggataac    62460
cactgggaag gagctgattt taggaaaagt tagtgagtgc aaaaggtgcc ccttaaagga    62520
tgtgaaagat tggtgccgga aagtggattc tccaggtac tgctggcaaa gtaagaattg     62580
agtcctctct caaggggaac atttagcaat aactgttcac atgcaccagt ctttaatgca    62640
gcaattctac ttgtagaata tctctattgt caaggcctgt gtatattcag tcctagtaat    62700
gttgtaagta aaagtgaaat actgggaaaa ctaagatgcc cacaatagag ggctggcttt    62760
tacagtatat ttatactgta gaacaaacta tgcagacatg aaaaaataca aagctaaatg    62820
ttcagataca gaattctaag ataatgttaa agaaaaaaaa gatgtaaagt gtcttcattt    62880
gtagtttaaa aaatataaaa acatgtctat atgcataaga aacatatgga aggatctaca    62940
agctacaatt caagttgagg ggagagagaa tcgcagctat gaaaacgcat ctgtagacta    63000
gagcggaagc agagccagtg cagaggggct catcatcaca agaatcccaa gtcagagagg    63060
cagccagaca cccacaccac ggcccttccc tcagccagcc tctagaaaac acaggtttag    63120
gaattacaag tagaaaggat taattgccat ctccattagc atttaggtcc tttgatgaaa    63180
ctgaactgtc aaaaaaaaat cttaatgact ggtgtataag taaaactgca tttcattgga    63240
agttagactc tctttccctc aaagccacaa gcagttctgc tataggcagt ttcagagcac    63300
tttaccaccc ctgaacccca aatttaggtc ttctcttctt tgccctgtag gccagagctc    63360
ttcgggaaac caagccaatt cctaatctca tctttgccat tgaacagtat gaaaaatttc    63420
tcatccacct ttctaagagg tcaaggtaa gcatattctg taattttct actgatttcc      63480 acttagcctg tgagggacc tggcaaactg aagcaacaca actgcactgg ggggaggcga     63540
ctgcgtttct tttgtttctt tgctatttct gatctgatgg cctgaagcca aacattgaca    63600
caggggacct gatgtgaagt ctagtgggtg tgtacttgct tctctaggaa ctgaagggtt    63660
tatccgggat ggcttaggca gtcctgggca ggttttattg gtggcaaact gtgcctgtgt    63720
```
ttacaatcct gtcccaggtg aacctgatga agcatataaa gctcagcacc tcacgagact    63780
tcaagatcaa gggaaacatc ctggacgtgg ttcttcggca ggaggaggat gaaaatgaag    63840
aggtcagtgc ctgctcagac tagagtgcag gaggcttcag ctgccctcct ggctggctgt    63900
cagtagcctg tcagggagca gccacagaga aagagccaaa aggtggtcaa agacgaaact    63960
aagcattctc aagagaaagg ttgtaaacgg tgaaccatcc ccgaagtttc ccaggcttgt    64020 ataccttag ggtggacatt tccagaaagg gaatgttgaa aacaaggtct tactgtgggt    64080
cttctcccca taaccttta aaccattgga aaattatgag cctaagcact ctggctcaga    64140
aaccagtttt tccctcttct accatgctgt cattcaaagt agggccacta ctctgaatga    64200
gggtcagcac atttcttagc ctcctttccc ctctgctgag actaaaggga gaggaacagc    64260
acgctatgag ccctcagca tctctgaagc agaacccagt gtttccttac ctctggtgcc    64320
cagaatttct atcaccttac atatatccaa gataaactgg aagttgacat caaccaccct    64380
ggatttctag cttctcaaaa aatcctgaat ctacattctt ccatttacca cactctaagc    64440
cataatacac ctggccctgt ccactgcctc tgcctccctg gcatttgagt tcaggggagt    64500
tctgcagcat cttgatgccc cttctctgtc accgtgttcc ctgcgtcatt acagaagtcc    64560
aaagggaagg agtcagcacc accttgctct gctgcagagc ttgcccccat ctccaacagt    64620
tacctcccgt gagtgggacg ggggagaaag catgaccaac acaggctttg atgagaagat    64680
aaaggatttc tgttttatt tccactgcct ctgaacaggc ttctcatgtt acagcgttac    64740
ttctctcccc ttctagggca ctgcatcaga gcatgagggg cagaacaaag aaccagccaa    64800
gaagaaaagg aaaaggaaa tgaaatgcct gagttaatgt gaactttggg gcttctgctt    64860 tcttttacc caacaagcaa caatgccccc ttgtcctgct gcctgcacca cattggcatc    64920
ttggttctga actcaattgc accttcagtt tagaggcaat cattcttggc aggctctgct    64980
actgaaaaat ggctggcctc aggccagccc ttttgcaaaa agcagagctg aaagcctgag    65040
ttttaggagc ctgcactgcc ccaatgaagc tccatgggag caaatacaga gcctccaggc    65100
agggctatag tccaggctgg cttcattct ccagggagcc tttggtgagt tcaattatct    65160
ggtaaatatc cagcgcttca cctgaaaaat agtgcaattc gttaggatgc cccctcacga    65220
agcagtcaga agtgagaaac gcttaatgtt aaggtcaaaa aggattgcca agaatggtag    65280
ggtcatattt ggggaggatc tgttttcttt atttataaaa tgtttgtctt agatacattt    65340
taaatagact ttaagctttc taatttgttt ggcattcaga gcataatttt gtcacctaag    65400
aacccactgt gactttaaaa taaatctcgt ttaaatcttt tgtgtgtgtg tgtgtggtta    65460
aagaagaaag aaaccggagt caaacacttc gtttactagg aacatctttc tagaaacaca    65520
tgcctttgtg atctgaacat tatgctcact ttggactcag ggcccgttat aaaccgaacc    65580
agcccagtac atagcccaag ataggggtta ccctccagtc cccaagcctc tgttgtctga    65640
gaccactttc tagtccacct cccgtcccat gtgtaataag gaaggaaggt gttgtgctca    65700

<210> SEQ ID NO 2
<211> LENGTH: 62371
<212> TYPE: DNA
<213> ORGANISM: Bos taurus

<400> SEQUENCE: 2
tcgctaaata gtgaccaact ctttgcaacc ccatgaactg cagtacatca ggcttccctg       60
tctttcaata tcttttggag tttgctcaaa ctcatgtcca ttgagtcaga gatgccatcc      120

```
aaccatctca tcctctgtta cccacttctt ctcttgccct caatctttcc cagcatcagg        180
gtcttttcca atgaatcggt tctttgcaac aggtggccaa agtattggag cttcagtatc        240
agtccttcca atgaatgcag gaatctaggt tcatttaaat tattccttag atttgcattt        300
tcactatcta aggatcggta cattcaaaac acagaacgtt tcctgttttc ccttcaggca        360
cactgagacc ggagactgca gggctacgga cttgattcct gaagtacagg aattgcacgc        420
aacatttatt tttcctttac aggggcaact ggcacctctt acggcacaag ggagtaagga        480
gacttcctct gccttccagg catttcccat gcaacaaagc attactttga ttcattggct        540
ctctcactga cccttttcccc aattgtacat aggaaaggcc ttaactgggt caggacatcg        600
tggtgactat gcccgggaca cacttcccct gctcattctg aggtcccgaa ttagcgtcag        660
agaatgtgtg cccccccccc cactttgaga tgggaacgtt cgagagaatc gctccaagca        720
cgagctcccg ggtaacggaa ataagccgca ggggcggga cccgttgctc agggtaacgg        780
aaggacggaa acggcaggtt gcgcgggttt tttggaattc agtggctgcg ttgaagtgga        840
agtgaccggc tagaggagct tcgcgcgtcg caggggagga gggactcagc tcccgggagg        900
taaggggtct gggaggacag gacggcgccc cttccgaatg gcgttctggc ttttccttg         960 gcccgaaaga gtctgtgccc tggcgtctcc cgttgtggcc tttagcgttt cctgctcctc       1020
gggcggccta cacccttggc cctctcgtta aattcttcct ctccatcagc gttcagctcc       1080
tacgtctgag acatttctct aaacccgttt cgcctttgta gctcggtcac agcgattatc       1140
cccagctgcc ttgttttata gtttctctgt gtttacttct cgctctccga gaagcccggg       1200
tgctaaaccc gcggcgtctc cctttcgtgg tgcctcacta acctcagggc ctttggacaa       1260
ggagtctgct atccgcacag ggacttaaca gccacctatc tgtgtgctac tcaattctgg       1320
ttttaggact aatttagcaa atgtacctgc tgaaatagaa ggagttcagc atcttccctt       1380
tagggctgga cgtttctttg gttgatatcc cttttctgaa tcctctacca ttcagcccct       1440
aatagagggg ctaatcgtag gtaagagtcc ccagtagtac gtaaaagcat gggttttggg       1500
gtctggaatt ggacagactt aggtttcagt tctacttctg caacttacta gccttctaac       1560
ctttggggga cgttccttaa tttctctgaa tctcaaatga tcttcatctg aattgggagt       1620
aatagcacca acctcagagg actggtgtga ggatcaatgt cattttcccc acaaatattt       1680
attgggcacc tattacgagc ttactgtgct aagtcttgga gattcagtga taaaaccaga       1740
ggtggccccc tgccctcttg gagtttgtaa tggagtggga gatgtaattc ttaatctaat       1800
aataagtgta atgttaaaag tgtggtgatg gtgagagatt acagttgcct tgaaagaatg       1860 taataggga gtgtttagac tgagcttgta aaggagtgtg ggattgagct gagacctgaa        1920 ggattttag gaattaacaa taaaaagatc ggtgggcagg ggatgaaaga aggggtattt        1980
atttttatat aagttccaga cagaaaatca tgtggaattg actgtggcag gaggaacttg       2040
ggggtttgaa ggactgagca gttcagtgta gctggaatat agagtgatga aaaggaatta       2100
acatggacca gccatgaaat taaaagacgc ttagtccttg aaggaaaagt tatgtccaac       2160
ctagatagca tattcaaaac cagagacatt actttgccaa caaaggtctg tctagtcaac       2220
gctatggttt ttcctgtggt catgtatgga tgtgagagtt ggactgtgaa gaaggctgag       2280
cgccgaagaa ttgatgcttt tgaactgtgg tgttggagaa gactcttttt ctttttttg        2340 gactatgaat atgctttatt ggagaagcaa agaatagaca cgctaattgc tcatgggtc        2400 aagatcacag tgcagataca gacacacaga tggcaaagag agatcaagcg atgatcctgc       2460
tgctcttcca acaacgtggt gtcagcttca ggaagcaagc cttttctctg ccagctgtca       2520
```

```
gtccaggagg gagattaagg aagatacaat ccatcaccat ggccaaaggg aggacaatgg    2580
gagagcctgg atcttgtttc ttggtccaga tgaaatctgg tgctgttact tccacttggg    2640
tggacacttc tgctcgcatg gtgggcatgg tgcccagga gggcatttct tctggcttag    2700
tggaggtggg catggatgag gtgggcaaga ctcatggcac ttgggtgggc acacttttgg    2760
aggtggatgg cagggctcct tgcactgatg gtgatgctga tgctgatgtt gatgcggatg    2820
cggatgggga tgcggatggt cagacatctt cctgggtctc aaggaatcaa atccaagctt    2880
gttccacttg ctgcagtgaa tctgagatga ggtgtctaga gtaggctgca ggcgtccttc    2940
cgttctcccg aaggagagga gacctggaga agactcttga gagtcccttg gactgcaagg    3000
agatccaacc agtccattct gaaggagatc agccctagga tttctttgga aggaatgatg    3060
ctaaagctga aattccagta ctttggctac ctcatgggaa gagttgactc attggaaaag    3120
actctgatgc tgggagggggt tgggggcagg aggaaaaggg gatgacagag gatgagatgg    3180
```

```
ggcatgatga gagatgtaag ggacatgtta gaattaattc tgccgcttca tctatccccc    4920
actcacctta ggagacaagg gtttatttga taacaactca tagatgtaac agaggaggca    4980
atggcacccc actccagtac ttttgcctgg aaaatcccat ggacggagga gtctggtagg    5040
ctgcagtcca tggggtcgct agagttggac acgactgatc gacttcactt tcactttcct    5100
gcattggaga aggaaatggc aacccactcc agtgttcttc cctggagaat cccagggaca    5160
gggaagcctg gtgggctgct gtctctgggg tcgcacagag tcggacacga ctgaagtgac    5220
ttaggagcag cagcagcagc acagatgtaa agaaatgggg gagaggaaga gatatggact    5280
acttaagggc atttggagaa ggcaatggca ccccactcca gtactcttgc ctggaaaatt    5340
ccatggatgg aggagcctgg tgggctgcag tccatggggt cgctaagagt cggagacaac    5400
tgagtgactt cactttcact tttcactttc ctgcagtgaa gaggaaatg gcaacccact     5460
ccgctattct tgcctggaga atcccaggga cggcggagcc tggtgggctg ctgtctatgg    5520
ggtcgcacag agtcgacat gactgaagtg gcttagcagt aagggcattt gtgtacattt     5580
atacaactat aatttcttgg gaacatacag tttaatgaaa tcaacccaat ttgagatgga    5640
gtgcttaaac agatcaattt tcataaaaga aaaaaagtta gcagttatac ttcaacaaaa    5700
ataccaggcc cagatagttt ttcaggaggc ttctaccaaa cctttagaaa tcagaggtaa    5760
gatctagata gtcccagtgc tacacaagtt gttttagagc acacatatta cgtaatgtat    5820
gtatatacat aaggaaagct tcctgataaa gacagcttga aggggcttcc attggtgaaa    5880
tgtgaacatc aaaataatca agttcagtta tgaattataa accactgaaa tataaagaaa    5940
tctgtgagtc catattgata aaaaaaaaat aaatggtggg aaaggttctt gcttaccata    6000
aagttagaaa atcgtcattt ggcaacagtc atgatcaaga ttggatcagg cagaagcagc    6060
agtggatgct aaatccaggg agcagttttt tgaacttttt atttttgaatt gattttagat    6120
ttacagaaaa gttgtaaaaa tagtagagtt tctgtatagt tctctcccca gtgttaacat    6180
cttacgtaat aatttcagta aaattttaca agccaggaag ttaatatttg tacagtacct    6240
ttagtgagac taaagagtat ttgaaccctca cctggtagtt ttttcactga tacccgtttt    6300
ttttttatgt tccagaatcc cactcaggat cctacactgc acttaattgt tattttcccc    6360
tgattttctg caatcagcaa ctgctcctca gtctttctct gtcttttgag aacactgaag    6420
agttttgatc cattattttg ctgactgtct gatgtgtctc atgattggac tcaggacatg    6480
catccttagc aaaaagacca cagaaatggc tccatgcctt ttcactgtgt gttatatcac    6540
tgggcttgtg atgtgccata cctggtgatg ctgactttga gaacctgata ttagaggttg    6600
ctgctgggct ttttcattat acaagagaaa gtgagatgag gaacacaata cttgcatggt    6660
cttaaagtta cttccacaaa ctgcatactg gttgcaaagg gaggggaaaa ataattata     6720
aagtgggaaa atcaggcaac acatttgact gggtgatcag actcatacta ccagtgaagg    6780
acagatggta tcacatgcct ccaggtgtaa tactccaaga aggacacagt atcacttgta    6840
ttctggccaa gaatgcgtaa actcaagtct actcacgagg aagcatcaga caacagaaaa    6900
tgaggaatgt cctgtcttat aaaaatctat tttcacggtg ccattaactt ggtagttcca    6960
gtctgtccac taaagaaaaa aatgttaagc cttccaatat agcaaggata cttaatctta    7020
cttgggggctt ttctggtggc tcagatggta aagaatctgc ctgcaatgca ggagacctgg    7080
gttcagtctc tgggtgggga agatcccctg gagatgggaa tggctaaccc actctagtat    7140
tcttgcctaa gggaatcccg tggacagaag agcctggcgg gctacagtcc atggggtcac    7200
agagtcggaa atgactgagt gactaacaca cacttggttt acttttgcat tttaaaatgc    7260
```

```
agtaaaaagg taactgaata aggtcaaaaa ctaagactgc agatcatgta actagaggga   7320
ggaggacgaa acaggaatag aggacaggag gaatgggaga gagccagcat ttgtttggaa   7380
cctgctgtgc actagaactg cacagggtcc tctctgcctg tcatctaatg taaccettct   7440 agcagtgctt tgaggcaggg actagacacg cataacaggt tagataactt gaggttgtaa   7500
agctaatata tggcaaagcg aggattcata tctgggtctt ctgattctgg ggccagtttt   7560
tttcccgtat gccatgttgc cttctcttaa aactgaattt tttcaagaag agtcagggtt   7620
tctcagcctt ggcactgtgt atattttaga gtggataatt ccttattgag ggaggttgtc   7680
ctaagcattg taggatgttt aatagcatcc ctggcctaca cccattaggt gacagcaccc   7740
ttccagttat aacaactaaa aatgtctcca gacattgccc tgtataccct gcctggggtg   7800
gaggtaaggg ggtaatccct ggttgggaac ctctcctcta ataagggtta tgtcaagggc   7860
tattggaggt tccaggcgga gcagtcagct acttccttat taagtattta agaagggaga   7920
gagaaactcc agtcagaaag accaggcaca tgtagaaggc ttctgtggta gtcctttgtc   7980
tggatattat caacctcatc ttctcagttt tttctggctg ctgctgctta atcactgaat   8040
gtttgtgctt tttttatctt tacattttct ccctggatga tcttacatgt tcccattgac   8100
ctctttcctc tctgagctct actttggcat atccagttat caacttgaca tctccacttg   8160
gatatcttag aaatagtagt tctgagcccc acatcagatg tgctaaatca gaaactgcaa   8220
gtgagggtct ctgttttaac aagccctctg gaagatttag atgcttgctt aatcccaaat   8280
tttcaccatg tcagtaaatg gtgtcaccat ctagccagtt agttgcttaa gccagaaatt   8340
tgagttctcc ttaattttc tttttccttt atcaccacag ccatttcact tctaaaccat   8400
gaggaaatct gtctttgtct tagtccattc aggctgctat aacaaaatac agtagactgg   8460
gtgacttata acaacaatta tttctcatag ttctggagac caaaagtcct ggatgatggt   8520
tccaatatgg tcaagtaagc gctctcttct ggatttcagg cttcacattg taccttcata   8580
tggtagaaag agcctgggag ctctgtggga tctctcataa gagctctaat cccatttgtg   8640
ggatttccgt ccttatacct attcacctgg caaagtctcc acctccaaat accattacaa   8700
tgggtctgaa gagtccaaca catgaatttt ggaggacata aacattcaga cccgagtaaa   8760
gtcctcctga tcaagctctc aaatatatct tcagtgtact gattttcaaa ttaaggtggg   8820
gttatatccc aataaaccca ttttaagttg aaaatataca ttgaaaaata tcgtaaatcg   8880
aaaatgcatt taatacacct accaaacatc gtagcctaac cttaccttaa atgtgccaag   8940
aatactttaa tattagtctt cagttgggta aaatcatcca acagcctgtt ttttaataaa   9000
gtcttgaata tctcatgtaa tttattgaat actgttctga aagtgaaata ctgaatggtt   9060
gcatgggtgc agaatggttt aagtgtattg gtggtttatc cttgtgatcc caagctgat   9120 cactagccca ggaaagggca aaatttgaa atacagtatc tactgaaagt gtatcacttc   9180
tgcaccactg taaagttgaa aatcaaagtt gatccaatgt tttaagttgg ggaccacctg   9240
tacttcatct tacaaagtac ttcaaactac agtagctatt tttacagttc tgaggactag   9300
aagtccagga tcacagtgtc ggcgttgttg gttcctacta aggctgtgac tatccgtttc   9360
acgcctcttg cctagcttct cgtcgattgc tgacaatctt tgagattcct ggccttgcat   9420
cacccacccg tggtttctgc cttcatcttc acatagcgtt cttgctttgt atgtgtttct   9480
gtcccaagtt tccattcttc taaggacat tagtcatatt ggattagggc ctacccatgt   9540
gacctcacct taactaatta cacctacaat gaccctgttt ccaaataaaa tgacattctg   9600
```

```
aggtgctggg gattagaact taagcatgaa ttttgcaggg gaacacagtt cagctcatga    9660
cttctctgat gacgtcagtg taggccatta tctctctatt gatcactgta gcaatctcct    9720
agcgtatttc tagttcattc ttaaaccctt ctatagtgta gtttctgcca taggaggaag    9780
actgatttat tttttaaaca tctgtcatgt ccctctcctc ttttctcttt agttacttct    9840
gttgcatttc gacaaaaatc tgaacttcct accatggcct acaagattct tatcatctgg    9900
ttctctcgaa attcatcttg tgccactctt ccttactact tttcatccaa attggtcttt    9960
aaaatttttt ttcaggccat ccaacttgcc aaacgccttg ctccttcagg acctttgcgt   10020
gtaacaatgc cttcatctga agtgtcttcc ttttccccct ttgcataacc agctttttct   10080
catcctccaa ttctctatat ggaaatgtcc tccacctcag agaagctttc tccctgacta   10140
ctctagcgga agttgcctcc ctttcctcaa ttactatctg tttcagtctt ttcaaccatt   10200 tcttttctg atttttttc ctgttatcct ttttgcttct gtcttactgt aaactgagtc   10260
agactgtgtc tgtcttgttc attcttgtat acctaatgct gaggaagagg aacatattca   10320
gagtatttgt tgaatgaatg tatatcccca agaacatagc tcaataccta gtgctgatta   10380
aatacttaat aaatgtttgt agaatgaacg tatgaataaa tttcatcttg accacccagt   10440
atcatcttat gatccaccct ctataatgtg aacacatatc ttattttga tgcctggagt   10500 ttctgaaaga tatgattctg acagatgagc gttttcata ttgggagttt aggtcattca   10560
aatagggaaa ttgttgccag acttgtacct tttccttccg ttctttgtag ctgactgacc   10620
tccttcagaa tcaggcggtg agaggaaaaa ctgctggagc actgctgaaa gccatcttca   10680 aagtaataa taatgcctct tctctctctg ggttcactgg tatgtttgtt tacttttggc   10740
tcctattgct actctttgta ttgcttgaag ccccgctgaa acttttctgt tttggggatt   10800
ttacagaatc aatagcacta tcttgtggac ttaaataatt tttctaaggc aggtagaagt   10860
ggctatctga gattgtattg ctagttttag aacctgtaaa ggttgtactt cataaaatac   10920
ggtttggttt acttgtgctt ttaagcttgt ggagaacggc aatgtttaat acttaatctg   10980
tgtttaacaa gaggctaggg agctctgagt taaagaaatg gaataccta gttgacttat   11040 ttagagatgc ttaattccca gtggggaata tttgtttctg tatcttgaac aagggccagt   11100
tttatattgt ggcagattgt aactcacaat cattttataa attgtagtag aataaaattc   11160
tataagcaca aattaaaagt ggctttagac tcttaggagg ttatttaac ttggtttatt   11220 tttcttaccc cctcaagtaa ttgggtcttg ccttgcaagg gttcaaaaac acatatttaa   11280
aatttggaaa cttttaaat gactgttctg tagaaatatc tgagaccagg aagtaacaga   11340
gaatcaggag ctgctgccta tgtatactaa gtgaaagtaa taagagtaaa actgggaaca   11400
gattatcatg gctcccactt gtgtaactaa ccttattttt accttattta aaatcataga   11460
tttggaaatc tgagtttcaa attagcatga attatcgaat atttatggaa actgcctcat   11520
aactatttta atcctgttaa atcagtgctg tgaaggacca atagttagct aatgatacgt   11580
tttataaaat tgagatataa tccatgtact aaaaaattca ccctttttaaa gtatatatta   11640 ttttattgag atgtaattga catcataaaa ttcacccact taaaatatca attcatcggc   11700
ttttaatata ttcaccaaga tgcacgcctg tcaaattttt cgagtatttg tattatccct   11760
gaaagaaacc ttacattcct tagctgtcac ctcctaaatt cctgatccac tccagcccta   11820
agaaaccact tatctgcttt ctgtctatag atttgcctat tctggatatt tcataaaagt   11880
ggaatcatac tgtatgtgtc ctttgtgact ggctgctttt acttcctgta aggttactaa   11940
gattcgtcca tgttgtaacc tgtatcagta tttcatttat ctgttgaata atattccatt   12000
```

```
atctgaatag atcatacttt tccattcatg aatgggtgga catttaggtt atctacactt    12060
tttagcaatt atgaatcctg ctacaaattt ttgtgtaaaa cattttcatt tctgtttggt    12120
aaatatttaa gagtagaatt gctaggtcat attggacaca agcgaagcgc cttagtagca    12180
gtggcagcat ggtgactctg tgtctaagtg tttgaggact gatgagctgt tttccaaagc    12240
tgctgcatcc tgtttccatc actattgaat aagaattccc aatgcccaca tcctttgtca    12300
acacttgtta ttgtcttttt cattctagcc actctggtga gtgtgaaggg gtatctaatt    12360
gtgggtttga tttgcatttt gctgatggct aatgatattg aatatctatt cttgtgctta    12420
ctgaccattt gtatgtcttt ggagaaatgt gtgttcaaat tatttgacct tttaaaaatt    12480
gattgtcttt ttattactga gttgtaatat ttaaatgttc tagatatagg tcccttatta    12540
gatgtatgaa tcacaaagtt ttttttccatt ttaggttctt ttcattttt taatggtatc    12600 ttttgatgca tgaagtttta aattttgatt ttttttttta attaaaaaaa attaattttt    12660
tgtagcttgc acttttggtt tttatctaaa agatcattgc ttaatccaaa gttacaaaga    12720 tttataccctt ttcaagattt cttgaaaaga tttcttgtgt tttcttttca agattataat    12780
cttagctttt acatgtaaaa cttttatcca tttttgagtt aattttttgta tatgatgtga    12840 ggtaggagtc cagcttcatt tttccccatt tttttcttct ttttaaaaaa tatttatttt    12900
atctggctgt gctatgtctt agttgcagca tgtgggatct agttccataa ccagggattg    12960
aacctaggcc gcctgcattg ggagcacagt cttagccact gaaccaccat agtacccttta   13020 ttgagaatca attgcccata gatgcgaggg tttatttctg gactcagagt tgtattccct    13080
tgatcgagat gtgtctcttt gtgtcagcac cacactgtct tgattagaat agctttgtgg    13140
taagctttaa aattgcgaag tgtaagtcct ccactgtttt cttttttaga attagtttgg    13200
atattctggg tctcatgagt tctcatatga attttaagat tagcttgtca atttctgcaa    13260
aaacggaaac tgagtttttg gtagggatta tgttgaatct atctatgaa agtattgcta    13320 tctttatatg tcttccatta ataaacatga catatcttc catttactta ggttctttt     13380 catttctttc aacaatattt tgttcttttc agagtacaag tgttgcacta ctttattaa    13440 atttattctg aagtattctt tgagtgtgat tgtaaatgag attcttttct taatcttctc    13500
attgttcagt gctagtgtat agaaacacag tagatgagta tattgatctc atatcttgca    13560
accttcctgt acttgctgat tagttctagt agtttcttt ttgtggagcc cttataaaca    13620
aaattatgtc atcttcaaat agatgtaact ttacctcttt ctcaatctag atgccttta    13680 tttttctaac ctagttaccct cagttggaac ctccagtaca gtattgaata gaaatgctga   13740
gagtgaacat ccttgttttt ttccctgatt tcaggggaa atctttcagt tttttattag    13800
caagtatgat gttaagttag ttaagtctct cacttagtca tgtccgacct ctttgcgacc    13860
ctgtggactg tagcccacca ggctcctccg tccatgggat tctccaggca agaatactgg    13920
agtgggttgc catttccttc tccaggggat cttcccgacc cagggatcga acccaggcct    13980
cccacattgt gggcagacac tttaacctct gtggtttttt catggatgcc ctttatcagg    14040
ttaaggagtt ttccttctat tcctagtttg ttgagtgtt tttttttttt aatcatgaaa    14100
cagtactgaa atttttcaaat gctttctctg tatctgctga ggtgatcatg tgacttctat    14160
cctttattct atttatgtgg tatatgaaat tgattttcat acattgaacc agtattgggt    14220
tactgggtta aatccagttt ggttagagag tacagtcttt gttttatgtt ggtgaattta    14280
gtttgctaat attttgttga ggattttgc atctgtagtc acaaggaata tcattcatag    14340
```

```
ttttcttaga atgtctttgt ctgctactgc tgctaagtca cttcagtcgt gtccaactct   14400
gtgcgacccc atagacggca gcccaccagg ctcccccgtc cctgggattc tccaggcaag   14460
aacactggag tgggttgcca tttccttctc cagggcatga aagtgaaaag tgaaagtgaa   14520
gttgctcagt cgtgtccaac tcttcgcgac cccgtggact gcagcccacc aggctcctcc   14580
gcccatggga ttttcgaagc aagagtactg gagtggggtg ccattgcctt ctccggtctt   14640
tgtctggttt aggtataaag gtaatactga cctcatagac tcagtttgga aatgttacct   14700
tctcttctgt tttttggaa gagttgctgt taattcttta aatgtttggt gaattcaccg    14760
gtaaagccat ttggttctgg acttttcttt gtagaagagg ttttattgct aattcagtct   14820
ctatttataa gtctgttctg gttttctatt atcttttta gtcaattttg ataactttgt    14880
gtctttacag caatttattc atttcatatg ttgtttattg tattacttta ttttatttt    14940 ttttaatttc tgcaagatta gtagtaatgc cactctcatt cctgatttta gtaatttgat   15000
tcttctctct ttttttcttg gtcagtctga agatttttca actttgttta tcttttcaaa   15060
gaaaaagatt tggtttcctt gattttatt attctattct ttcatttatg tctgatttta    15120 ttttatatt cttttcactt ggtttgactt tagtttcatc tctttataat tccttatggt    15180
agaagcttgg gttattgatt tgagatcttt tttaatgtag gtatttacaa ctgtaggttt   15240
cgttttaagc tctactttag ctgtattcaa taacttttgg aatgtgtttt tttcttccca   15300
ttcacctcaa ggtatttttc tctcttttcc tgctgacttc actcagtgat gatgttttga   15360
agtaaagtat gttacttaat ttgggttatt ggatcccgaa aagctttaag aaatattaga   15420
aggtgttcct tcttctgcac tataaaatta ttttaaaaat taatggcatg gatggaagtg   15480
tacagaaaaa ctggtatttc agttttctgt ctaaattaaa aaacttttc aaagctccta    15540 aatattggct gttctaagta ccatagtaag tattttgata attctgtttc tgtattcaac   15600
tgcaaagctg tttgttattc ctgtttgccc ttcaaccttg tcagacttct tcctttttc    15660 tttctttgtt tctgtgctac ctgttgaaaa tgataaggtt taccctgttc tgaggaagct   15720
ggagctctta agagacttaa gatatacagt tgttgtatcc agttgttgga atcaggggat   15780
ttacagaaag aagtagcatc tgaaatcaca ggattgctaa tgctggaggt gagatggaaa   15840
acaaaactgt tttggttttg gttgaatttg gagcggggtt ggttatatgt tgagggaggg   15900
aaaatgtaaa cgtctcagac ccaccatagt tcctacttac aagtaagaac taccgttcta   15960
aaacaaaata gccgatgaat gagccataaa ccacctagat gtttatgtta cgtttccagt   16020
atcatggaca tgtgtctctt tcaagagctg gaatatttaa gaacatcagg gaactaatgg   16080
aagatcctga ccttttgaaa tcctttacca gagcagaatg attccctgaa tcacttttag   16140
aacccgtttt gggcttcaat gccagttctg tcaactcagc aaaagactga ttttggaaa    16200 gaggtatcaa acatctagat atctgctgaa tgttttttaa tcccatgaac tttaggttca   16260 ccgtttccg ggacagctat tggttgaatt agccaatgag tttgttagtg ctatcaatga    16320
aggcaagctc acaaacggaa aatctttgga gctgttgccc gtcattctca ctgcccttgg   16380
taccaaaaag gaaaatctga cttatggaaa aggtaatttt tcttccaatt tcagtggctt   16440
gttctttctt cacttaatcg gatttattct tcagtgtatt ttgcatttct aggtgaacta   16500
agtggggaag aatgtaagaa gcagttgatt aacaccctct gttctggcag gtaagtcctt   16560
aataatatga agaattttc tcaggactat aagtcaccaa aaaaaggaat accattattt     16620
tgggaattta tatcactgaa gttttagtcc attttttgt ttatgattta ccactataaa    16680
accatttagt ctgtgatgag ttttgagag aggttatttg ctgtattctt tattctaaca    16740
```

```
ttatacatat agtctctact tacttaactg tcatcctaac acagcaattt agccctatag   16800
tattatttgg agtcccaggg tcttcaaggc tagaaagtca ccttgccact atcttttatt   16860
ttggggcggg ggggatatat aagtgatatt tttatcatta agcctgatat ttgtatcttt   16920
aaacctgaaa tacaagtgtc tatgctaagg aaaaactgca ttgtataaga aagtcttcat   16980
acatgaacat ttcaatacag aaatttgtga ctagcttaag gacacaataa tagagatatg   17040
taagttgtgg tatgtaagct ataaaagagc cactccatgc aatttatacc cattaaaaat   17100
gaaatatata aagacatata gcgaagatga aagatctttg tgtatatatg tatatatata   17160
gtaaatcctt aatacgtgtt tttatatata tagcctgaaa tgaatagaat actaagttac   17220
ataatactgt gattatactt caatatgttg aaaggaacta gattatccaa accagagata   17280
actgctttca tggttcataa ggtctcttac agaaataatt ttaagcatgt atcagctcag   17340
gtatgtttat ccatttattc ttaattacac aaaatattat tcattctaca ttgtaatgta   17400
ccttgcattt ttcatttaac acatatgttc atgtcagcat atactacttt acatcattct   17460
ttttaatagt tccatagtat tctaatattt ggctaatctc taattgttag attatttagt   17520
ttttgccagt aaataatatt ggctatttgg gttttgcta ttataaaaga tgttgcagtt    17580
aacattcttt tatgtctggg tgaccttta taagcatgta catgggatat attcctaata   17640
gtaagctggg tggctctttg gttatgtgca tgttaaagt cggtaagtag tattgccaac    17700
ttgtcttccc agaaggatta tatcagtgta tgttccacaa aatagtatgt gaagtgtttg   17760
ttcaccaaaa tctcaccagc actgaatgtc atcaggcttt gattgtgcca gtccagtagg   17820
ttaaaagctg ttatttcatt gtttaaatg tcatttcttt gatgttattt cccagtagca    17880
gcaaatcaaa cttgaaatgg ccctaattct tttcttcctt gctaatttta taagtaaca    17940 tgtaaataag ttaaaacaac ataaactttt cttttcatt tttaatcaga tgggatcatc    18000
agtatgtaat ccaactcacc tctatgttca agtaagtatc atcattccct tcttttttaa   18060
tcctgctgtg agaacttacc tgctagaaat tgaaatgtag taagctcaaa taccactgtt   18120
cctgagtaag agtattgata cctctgtttt ctgttacaag atttccccc acccttttt     18180 gctttaattt cttatttaaa gtatatgatg ttttatttcc aagataactt tgctgaggaa   18240
agattattgg tttccttaa ggttctccat tagagaaaaa tcaaaagacg caattaacaa    18300
cattctgata tctcccaaat tggtctctaa cctttagaat ctttgatcca cagggctgtc   18360
cctctgacta cagaagaggt ggaatttgtg gtggaaaaag tgttgaaggt gttctccaaa   18420
ttgaatcttc aagaaatacc acccttggtc tatcaacttc tggttctctc ctcaaaggta   18480
taaataaaat attttttaa actctggtgt aatgaccaat tattaccatt cagtttattc    18540
atactcttta ttttatgtac taggacatag aaactttcat ttcacatatg acaatttggt   18600
ctactaaaaa tgtcatggtc ctcagagtga atgtgtgtta tctctggtct cgtgtgtgtg   18660
gtaggaagag ggatgaagag ctctgaaagg gtggattgta ggcccttag agtctgatat    18720 taagatgtat ttcaaactct gtttcaaaaa gtgtttttat gaaagtgttc tataaattct   18780
tagtgtgagt ctagcttata atttatttaa attcatactt gaaaattctt taagttgaaa   18840
agtagtttaa cttgcccctta tttatttgt tttattcttt ttcagggaag ccggaagagg    18900
gtcttggtag gaatcatagc tttcttcaac aagctagatc agcaacacaa tgaggaacaa   18960
agtggtgatg agtgagtcaa agagtataga aataaaatca ttttttccaaa ttcatcatct   19020 cattatctaa ctcttcagtc cctaccttcc cctcagctgc tcagtaataa agttaaaaaa   19080
```

```
tagtgtagtc tcctcaactc ttattttaat ctttcctgga aaacagcaat aatgactctg    19140
tagttataga cttcaaaggc atttattaag tgtttactct gtgccagaag ctattggacc    19200
tgggacagtg atgaaccagt caaagttcct gctctcatgg agaaatttta atgagaaaag    19260
aaaagaaatg acaagaaaag tattagagtg gaaagggcta tgcatacgtt tcaagtggat    19320
gacgtgacag tgacagcatg gctacgttag gttgaggggt cagggaaacc tctgagaatg    19380
tgctgtgtta cctgaagcct gaaggataag agccataata tgtagctcaa ggaaaaaaac    19440
attctcagtg gaagagttag tccaaaggca ggacacagca cggtatggct ggaaaagagt    19500
ttttgaagca aatatttgta gaatgcttgc tgtgtgccaa gtactgtttt ttagcacttt    19560
aaacttcaca gcaactccat tttgtctctc ttttatacat ggagaaacca aggcacagag    19620
aaattaaggg atttcctggg gttatatagc cataaattgg tggagctgtg atttgaatgc    19680
aagcaatttg tctgcagcat ttgtgctttt aatcctatct caatctacta acctggaata    19740
acaattttaa gttgttgtac ttgagcagtt gatgagaagt tgttcttgta tactgagtca    19800
ggaaagactg acagaacaag caggtttaga ggagaagaag ctcagttttt accatggaag    19860
tttgagatat gtattagtat cttatatgaa ggtgctgagc aggcagtctg gagtttcagg    19920
gagaggttgg gaccagagat acagattgga agggactgaa gcctgcaggc tctttagggt    19980
ccctggggaa gttgtgaaaa gagaaaagga acccaagatt gaactctcag aggcattcca    20040
ccacttgaag gatgagccag cacaaataat ttgaggccag tgcagtgcc ccaggagcta    20100 agagaagaac atgtttccag aaagaaaggg attaactgtg tcagatctac tgaggcttta    20160
attagggtga gacttgagta ttgattttga caatgtagag gtcatttgta gcccttgcaa    20220
ggataatcaa atagcattgg aagggaggtt agggagggca cagaagctta attgagttgg    20280
atttaactgg ggagaggtaa acaagtggaa ataatgacca tagacagttc attcaggaag    20340
tttcatgaaa aggagcaaag aataagtaga ttttgtactt tctgcctgcc tccagtgatc    20400
ctgttagttc agcctgagtt tttctattcg ttcatgtgag caaatgcact gttgtctctt    20460
ggtcaagcta tagctcaaac ctttctgttg aatctttag gtacttggat cttattactg    20520
taccattgga tgaacttcgt cacgtggaag gcaccattat tctacatatt gtgtttgcca    20580
tcaagttgga ttttgagcta ggcagagaac tcctgagaca cttgaaggta gtaaccagac    20640
tcttaaggtg atccaggatc tctatgaaac aaggacgttt gaactcaagc ctctttttat    20700
gccgtttaat gactggaaac caatacatag aaatactata gaaagaccct gggtctagag    20760
ggtctctttt ttaactttga aagtggaaga tacatgatac cactcatttt ttaagcaagt    20820 cccttttttaa aaccagacct taagtgttct agtgtttttc tgtttgtttg tttgtttaaa    20880
gatgaagact gttctgtagg aaattcaaaa tttagcctta gctccattat tatatgaact    20940
tcactcttga cttgtttcct tatttgcaaa ttggggaaat tgtctctttc tcatagtaaa    21000
tcatggagtt ttgtgaagct aagtcattgt taaatatttg tgaagtagta agataaaaat    21060
tagaaatgtt ttgaactctt aagtattttg ctacatttac cttatctcac ctctctcaag    21120
tatatttttt ctgaaccatt taaaagaaga aatattgaca cttcagtgcc tgaatatgtc    21180
cacatgtgtc tcataagaat aaggattaat acctttttat tgaattttt taagaatcct    21240 gcccagtttt cttgtgtctc atattgtcag atttgtctta ttgtctcccc atgattagat    21300
tcaagttaaa cattttttggt gagaaatatgt ctcaagtgct gttgtgtttt ttctcttgtt    21360
ggagtcagca aactttctct gaaggaccag ataaactatt tcaggctttg cggatgacat    21420
ggcctctgtc accactacac tactcttgta gcaagaaggc agctggagac aacacatgaa    21480
```

```
tgaatgagtg tggctgtggg ccagtgaaac tatatgggca ctgagtttta attttattta   21540
attttcatgt gttatggaat actattactc ctttgacttt tctcccctca acaattaaaa   21600
atgtgaaaag cagtcttagc tcatgggctg tacaaaaaaa ggtggtgagc tagatttgtc   21660
ccagaggctt taattctatt gcatcacatc aaaaggctca tagtatcagg cagtcttagc   21720
caaatcattt tattaagaca aggaccagca gttttcttca cttgcaaaga tatatgtttc   21780
cctttgtaat tagaaattaa tccatggggt cataatttga gacatgtgaa aatcctttcc   21840
ttagcaatct tccacacagt ggattttggt ttcccatcta ttaatgattc ttgtcctaaa   21900
tcagtaatta tactgggagt tgcaaaatgg tagaattaaa atcagaagtt tttattggtc   21960
attccttcta gttggttttc tgtgaaaaga gccccacacc tccctctttt tttttttga    22020 atattgttat gcaaccatga accttttaaa attccatgta ctcataaaca gtacccagaa   22080
tgatccatat ttggccattt ggatccctga ggttggctta tgtgtccttc taacatggcc   22140
atgttagtct ttgagcactt catggcgtaa gctatccaaa acacacctgt gctttcctta   22200
ttgcatctga tttctccaag gagcctcagg tcccttttgt aggagaagat atttaaagac   22260
caaatgtgaa aagtagcctt taaagctcct ttatcttctc tgtgtctata tactcttttt   22320
ttatttaggt ttctagtaac tgttcttttc aaagaacaag ctttgtattt gtttactgtt   22380 ttattttgt tttttggttt tctcttttat tcatctttga tttatttttt tcttttgttg    22440
tctgccattt cttttagggc tcaaaaacct attttttaac tttattgagt tacaatttat   22500
gtaatataga atacactcat tttaaagtat aattcagtga ttttttcttaa gtttacccag  22560 ttgtgcaaca accatcatca taattcagtt gtggaacatt ttcatcacct tgtaagatcc   22620
ttcatgcctg tttctataga tttacctttc ccagacattt catatgaatg aaatcactta   22680
atatataatc ttttgtgtat agcttctttc attgagcata attttttcaag gttttttatcc 22740 atgttgtagc atttaccagt atttcattct tgtttgttgt tgaatggtct tccactgtgt   22800
gtgtgtgtgt gtgtgtgtgt gtgtgtgtcc gttgattaga tgtccaccag ttgatggaca   22860
ctgcagttgt ttttactttt tggctattag gactaatgct gctgtgaaca tccaaatgca   22920
tgtctttgtg tagagacata tgttttcatt tctcttgata gatacctacc agtagaattt   22980
ctgggttttg taatacattc atgtttatat tttaagaaaa ctaccaaaact gtcctctaaa  23040 gtggctacaa cattttacat agccaccagc actgtatgag gactcctttt tttcccacat   23100
cctggccaac atttgttact gtctgttttt ttatacctat tctgatagct ataaaacagc   23160
ttattggcca ttctaatatc tttggtattg cagagtcaga catgacttaa cagctgaaca   23220
gcaacatcaa caatctttga tgaaatgtct attcaaatct tttccccatc ttttgattgc   23280
atggcttaca cagtttttaag atttctttgt atattatggg tacaagtcct ttatcgtgta  23340
tgtgattagc aaatatttt ttcagtctgt ggcttgtttc ttaatggtgt ttcttttgaa    23400
gcaccagagt tttgattttt aatgaggccc agttatcag tttttactt acataaatta     23460 tattttggc attgtatctg agaaatcttt aatccgaact cttgaagatt ttctgctgtg    23520
tttcctttta tttttttttc ttgtttccag ttctttatat ataaacaaat tctatccttc   23580
caaatgtaag ctatacatta cttccccccaa gtttattcaa ttcacatgtg aaaaattat   23640 gatttaaaat accaagctgt gtttcctttt aaaagttttt gtaggctttt tttttttttg   23700
gtcatactgt gttatatggg atcttagttc cccaaccagg aattgaacct gcactccctg   23760
aattggaaac acagagttaa ctgctggact gccagcgaag tcccaaaagt tttatagttt   23820
```

```
tagctcttag gtttaggttt ctgatccact taaggacctg ttattaagta gaatatgttg   23880
tatttttcaa atgtaagtta tgacttcttt ttggtttgtc tgttctaggc aacacagcaa   23940
ggagatttca gcagtatttg tcctttcagc atcgccctct tgctctctgt aacaagaata   24000
caaagatttg aggaacaggt atttatgagt gacttttggt ttccttctgt agttgataag   24060
gagtgtaaga gcctgtttat ccttttcctaa ataatttcac tcccatcctg ccagcagcaa   24120
attcccctgt aagaatgtag gcccacactc ttctctggga gctgcttgaa gacttcttca   24180
gatacttgat ttatacttct gtttcaaact atgtggcaag ccagaggctg agatgggaat   24240
agcagtggga acatcacaca gtccaggtag caagaatggc aagtttagct gggtattcat   24300
agcagtcgta ttatgttgta gctttctaag aaatattcct tgaccaagtt gaaattaatg   24360
agaataggtt tcaacttggt caaggaatat ttcttagaaa tattatttgc aagaatgaaa   24420
atataaaatc ctttacccctt ttttctcata cgtgtttccc tgggtgtggg taatattgat   24480
ttttagccat ttttctctca agtcaggcat gtcttcagct ccttttaagt tctcactgaa   24540
agttataatt tttgcgtcat gctcatctag tgaaacagtt atagggatat gagtgtgtgg   24600
cagcaagtag gaacagttac agggttaaga ttctctagta tgggctatac attttttgctt   24660 cattttccta tttcttttcat tatgttaggt gtttgacttt ttaaagtctt cagttataaa   24720
aaactttaag gatcttcagc ttctccaagg ctcaaaatat attcagagtc tatttcctaa   24780
tgaatgttgt atttcaacca tgatcttgga agtggtaaat aataggtaag tttatgaacc   24840
ataaggttta agctatttag tgctagaaaa tgcagtgcgg taccatactt atggcccatc   24900
agagaaaact gttgactata gttgttgact tcacatatca aggtttaaat cccttaaaat   24960
tgatcaagca gacttcccct gtatcaacag attctaaaat cccaaggctt gatttcttgg   25020
ccaccttgtt agcaagaata cgaaactgaa gtcggctcct ttagtactat tactgctctg   25080
ttggtctaag tcttcattgg ctttttaggt aaataaaaaa cagatttttt tactgtaact   25140
gttggagttt gggaatgatg gatggaattg aattagtagt tttagacaac tgacgagcag   25200
ttttaggcaa atctatcttt aaccaaatat agaagtaaaa atagaaaaaa tagaaaaaaa   25260
actggttacc atcctggttg ttattttcat ggttaatgtt gtatttcatt gtatacatgt   25320
atacatcagc cgttataata ttctttactg agtcatgctt tttttgtggt tttggtttgc   25380
tgtatttagc tctgttgaca atttctgtgc ttacctgcag ataatctgaa ggtgcaaaac   25440
attaatgtac taggaaaaaa atcactatga accaatacaa cttctaggtt gtacttactc   25500
ccatctgtac caatcacata tgaactcttt cacattacag ataagacatt ttgtagcaaa   25560
atggattgta actgcctctt ctctccaaaa tgagaacttt agggcacaat ttctccactt   25620
ccttcttgtt cagcattatt actaacaagc aatacttact tagacttcat tattttactg   25680
gtttctttgt ttgcatttat cttttgaatc tcatactttg gcccatctga tttctgcttg   25740
gtgtttaatg tacccttcca ctataaggat tcatgtattt cctcttgaaa tgttttttctt   25800 cattttttt gagtactctc tcctttttct cttggaatat cttgctctgt atactatgtc   25860
tcaatttttc tttcatactt tatgtatttt tgtcttttg tgtcaagttc tacaaaaatt   25920
cctgggactt tgctcatggt ccagtggcta aaactccatg ctcccaatgc aggagccctg   25980
ggtttgattc ctaatcagag aactagatcc tgcatgccac aactaacacc tggcacagcc   26040
aaaataaaat aaaaattcct gagctcattc tttagttact tcttcagttc tgtgcatttt   26100
attcttaggc catctgctga ggttttcact ctatccatca tgtttttat ttccaaaatt   26160 tccacttggt tgttttttca taacagttta ttttttgttt cttgcaatag tctttcttct   26220
```

```
ctgagaatat tcattagact tttaaaatct tctatttgtt ccattaatct tttcccatag    26280
gattggttct ctttgttgag tttggtgctt ctctttcctg gtcgtattat tttcttgtat    26340
ttggtgatta cttatttcct tattatcata tttgacgttc cccattagtt tgtctgagag    26400
tgctgtattt atttaacaca ctctacctca gggatacgag ggtagcagta ggatgtacca    26460
ggggctgatc ttctaggtat ggtgtctccc tcatccttca gcatgttgtc atcctctcag    26520
agtgctgctc tgcctctcag gccccagatg cagtgaggtc ttggagaaaa aggtggagaa    26580
ggttgatgtg tactgaactt catccagggg tatcctagcc agtcaccaca aaagttgccc    26640
cagggttcct tccagttccc agcataccta cccttggcat ccgcttttgg aggcacccct    26700
tcagtctgca taatgctgtc tatgatttct tttttccttc tattactttc attttttaag    26760
gattcttcat aatttctaga cagtcaaagc acctcttatt tttccacgtt atcatggatt    26820
gtatgcatgc accacatata gacattcaca cacagttata tctatctttt ctgtcatttg    26880
taagtattca ggttgggaaa aatggagcat gtactcattt tattatcttg atcccagatc    26940
cccagagtgt gactgttgtt aaaatctgtc agaatgttat gagaatctat tcacaactct    27000
ttcattcttt aatgctgcat tataatttgt tgctgtttag caggtagatg taatgatata    27060
aaggttatta taaacatgat ttccactata gtgggtaaca ttaagtggta taaaatcacc    27120
agggattctc ttgcttttcca aaggttggtt gtagttttat ttcatgcttt tgaaatccag    27180
tcattcatca gaccaattcc tactataaat atgaatatga aataaatatg aatataaatg    27240
ttcctattat aaatatttac cgagtacctt ctatatgcca gaatttgtgc taggctctat    27300
gagcaaaaat atgactacag tgtgctctcc accatagaga atctcaatct agagaggaag    27360
acaaacttgt aagcatatgt atatgtgttg ttattggcat gagggaata gtagaagcag    27420 aaattaaaat gtagtcatga aatcttgagt ggcaatctct aatgatctgt acactgaaat    27480
attccagttt cttccatatg ttgcttcatg ttccatagtt tctggatttt catggtgatc    27540
tgtcggtaga gattgcttgc ctaccaattc cccattactg ttcctccaaa aattcagaat    27600
tttgccagat taagggtaca tgaaaaggaa agactcatgt ggggtgttgg ttatacaggt    27660
caggtttggg aaatgtgtaa catggcaaag agtgtagagg taaggtgttt tattaagttt    27720
ttcttcttaa ctaaactttg ttttcctgca gtgttcatag ttgggatcat gttactcagg    27780
gcttggtaga atttggcttc attttaatgg attcctatgg gccaaagaag attcttgatg    27840
gaaaaactgc tgaaaccagc tcaggtcttt ctagaatgcc aaaccagcat gcttgtaagc    27900
tgggagctaa tatcctattg gaaactttca aggtgagact cgagttcagc aaccattccc    27960
tcattttgtt gtattatact acaaatagga cattcacctg ggagtttggg ggactgggca    28020
atttgagtat gtagcagttt ctgagaacag aaactgggat aatagttgaa acattaatag    28080
atgcagtttg atgaatactt tctcagtctt tatctgagtt tttcatctat tctaatttct    28140
gttctttctg accatttctt agaagtttga atataggtta gcttccttat gatttcctct    28200
tcttcctcca gcagtaaatc atttctgaat ttttttttat acccttatac aaaaaataat    28260
cttttaggtc gctgtagaac atcaaatttg aagaatcatg cctattggtt tattgttttt    28320
gaagaacccc aaatgggaaa ttcatattct tttaattcat taccatatta cgattgttat    28380
ctcaatctaa ataagatcat atctgaggct aaacaaattt gctttgctag tgatttctct    28440
aagtcatctt gacatccatt cttcagtgta tctacatacc aaaagtatct gctaacagtg    28500
ttatttggag gtcaatttaa atgtaaatct gatgttctga tccagaagta aagtgaatac    28560
```

```
catataatag tccttgaggg ttgtatgtta gatacacatg actctttaac agtaatctga    28620
ttttaaaaca ttcttagaat aagagactta atattttttg ttttaaaatt agtcttttt     28680 ttaaatcaag gttctacttg gttcacacag ttgttggcct tgtcacggta tctgtagaac    28740
atagaattta ctaataatca aattattaat ccagagtctg aaagaaatca gtctctaccg    28800
aaagtaatca agttcaggta tgaaatttag ctaaagttca agtaaaaatt caaaacaggt    28860 ccttttaag gcaactactc tgcttctaga aactgaggac agggttattg aagattttct     28920
agattttcag ggttttttta tgggctttta aattttaata tgaaagttgt gcatactgtc    28980
agaaatatgg acgttgacct aatagtagat acctaggtag aattattcct gtttgctgct    29040
ggaccttaca tgtagcagta ctttcatatg atctctctat aaggctaata aaagtttgcc    29100
tggttaatga atcatttgag tacaggatga taattcaatg attctttcca gatgattcgc    29160
ataatgtttg tctttgaaat aagcagtcca gttttaccca tattcaaact tttctttatt    29220
ctgcctaata ggtattaata caattgtaag ctgaagttca ccaaggaata ttttattgat    29280
tcttctgctc cttttagatc catgagatga tcagacaaga aattctggag caggtcctca    29340
acagggttgt taccagagca tcctccccca tcaatcattt cttaggtatt gaactttgaa    29400
agggtggaaa aagttgtcag gaatattttt atttaaatgt cataatgctt tggatcctgg    29460
gaaaaaacct gaatgatata gtagattaat gcaagatctt tgattatgat gccagtaaaa    29520
ataaattctt ttatattgtc tatggttgtc aagaaggaaa ggagcatatg agtgaaactt    29580
ctactttgca tcagctttct ctcttttttg ttttaataat tgtcaagtga gtcctgtcct    29640
tctgctgtct acttattgac ctcccactct cttaacccct gacattctga cttcattggt    29700
cagagtgacc agtggtcatt tggtgacctc tttggtctct ttggtgacct ctgaatttt     29760 tgttttttc gtacatattt cctaatgcct aaatccactc atcttaatca tcaacttcct    29820
taatttcctt ttcattctac actatttata actctcctga agttctctga taactgtaat    29880
agtttgcatc tttatcctg cctttgatca gtttttcttt cttcttagag attggttttc     29940
tttcttctat ccttaaatgt caaggttctc caaagttcta tacttgacat tcattctac     30000 tttttctttc tttacattca gctttactga aatacaatga ggtacagtaa tgtacacata    30060
tttacagtat aacagtttga cttttggtgt gtgtgtacac ccgtgaaatg agaccatca     30120 ccacagtcaa gatgaacata tctgtgtggg cgctaagttt tcagtcatgt ccaacccttt    30180
gcaacctcct ggactatagc ctgccagagt cctctgtcca tgggatttcc ctggcaagaa    30240
tactggagtg gtttgccatg ccctcctcta ggggatcttc ccaacctggg tattgaaccc    30300
ttatctcctg cattgcaagc agattcttca cctgctgagc cactggggaa gaccatgaac    30360
ctatctatca cccagaaatg tttcctggtg cctttttctg atgtattctt gcatctctct    30420
tttccttccc tgacctatct agtctggtct gctttctgtc actataaatt ttaaatattt    30480
tgtgtaaatg gaatcctaca atatgtacct tttttttct ttttccttt ggtttagttt       30540 tttcagcata attttgaaat ttttccaaat cctttgtcag atacaggttt tgcaaatatt    30600
ttctcctggt ctgtggtttg acttttaatt tttgtaacaa tgtcatttga agagcaaata    30660 ttttgtcag ttcatcaatt tctttgtata gttgctgctt tttgtgtcat gtatttaaaa     30720
aatttttttg ccaaatccaa ggtccctaag gtttctccta tattttctac tagaagtttt    30780
atattttcat ctgttgtact taaatatatg atccagtttt gttaaattct gtgtatggta    30840
taatataaca gtttgttttt ttgcttatag ctatccaatt gttccagcac agttttttga    30900
aaagattatc tttccttcat tgaattacta tggcttcttt attgaaatca actaactata    30960
```

```
taatgtgtgg atctatttta ggaatcttct attccagtga gctatgttat gtcttgattg    31020
ctatagcttc atattgagtc ttagaatcaa tagtgtaagt cctttaactt tgttcttttt    31080
caaaataatt ttggctattc taggtccttt atatttccaa gtaaatttac taatcagttt    31140
gtcaagtttt ataaaaagtc tgctcaagtt ttgatggaga ttgcctcaaa tctatggatt    31200
aatgtggaag agaattggca tcttaaccat attgagtcgt ctaactcatg aatacagtat    31260
atctctccat ttatttaggt cttcaatttc tttcaacact gttctatatt tttagtgtgt    31320
gtatcttgta tcttttgtca gttgatccct atttcatttt tttgacactg ttgtaaatag    31380
tatttaaaaa tttttcaatt tgtagattgc taactgttgt catgtagaaa tagttgcttt    31440
tttaatgctg accttatccc ctgcagccat gctaaaccca tttattagtt ctagtagctt    31500
ttcagcaatt cttcaagatt ttctacatag aaatcacgtc atctgcaaac tcaggcattc    31560
ttgatatcag tgatttgtct ttttttcttt atcaatctgg cttagaaact tgtcagctta    31620
cagcctttca aagaatggga ttttagtttg aattttctct attggttttt tattttcaat    31680
ttcaccaaat tttgcttttt attatttcct tcctcttgct tgcattgggt tcattttgct    31740
tttttaaagt gggtgaaaaa aatcaataga agaatatttc tgatacatga aaatttttaga   31800 tttcagagtc cataaaatat agtattattg gaatactgtg tttaccagca agaggtttcg    31860
gagaaggcaa tggcacccca ctccagtact cttgcctgga aaagcccatg gatggaggag    31920
cctggtaggc tgcagtccat ggggtcgcga agagtcggac acgactgagc gacttcactt    31980
ttacttttca ctttgctgca ttggagaagg aaatggcacc ccactccagt gttcttgcct    32040
ggagaatccc agggacgggg gagcctggtg ggctgccgtc tatggggttg cacagagttg    32100
gatacgactg aagtgactta gcagcagcag caagaggttt atcaattta ttgattttt     32160 tctaagaccc tgcttttcat ttcattgagt ttctctgttg ttttctgtt tttagttttt     32220 attgatttgt gtgcttttt gggtcctttc cacttcttac cttgggttta gtctgtgcta     32280
cctttggtta aatgcatgtg tcattaattt gaggtctttc tcttttttt caatacaggc     32340 gttacactgt aaatttccat ctaaacattg ctttagctgc atcctataaa ttttgttttt    32400
tattttcatt ccgttccaca tacttttca tttctcttgt gatttgttct ttaatgcatg     32460
ggttatttag aagtgtgtta tttaggtttg gtctactaat tctatcattg tgttgtttct    32520
gatatgtttt tgttgattta tgtcgtcttc atcatgagtt gtgttttcct gcttctttgc    32580
atcattaata agttttgatc agatggcaga ctttatgagt ttcacattgt tgatttgctg    32640 gattttttt tccttcaaat attcttgagc tttaagttcc ctggtgactc agatggtaaa    32700
gcgtctgccc gcaatgtggg agacctgggt ttgatccctg agttggaaag atccctgga    32760 aaaggaaatg gcaaaccact ccagtactct tgcctagaaa attccataga tagaggagcc    32820
tggtgggcta tagtccatgg ggtcacaaag agtcagacac aactgagcga cttcactttc    32880
acttgtttct tggaaagtat ttaatccttt tgatgattat ttctgtgttg tgtaatgaaa    32940
gaccattcag cttttaatct agggctaact tgatgctgca attaaggcaa tgttccttgt    33000
atattatgag gtgtgtacag tgtgggtgtt gtgaatgtga actatttcct gcccttatg    33060 acctcagaga atggatttgc ctactccttg ccagtaactt ttagcttcac tcaggttgtt    33120
ttttcacata catatgctga ggagcactca gctcacatgc aaggagagcc ccctgcacat    33180
ctccagggtg ctttcactgc agcccttttcc tttctagtgc tagctgcctt ggctttcctg   33240
aattctcaac tctgtctcta actcaggaag accactggct tctgagtttt tctctgtgtt    33300
```

```
cctgtctaga agctctccag gcagtaacat gggacaatta taagcctctc ctcatgtatt    33360
tccctctctc agggatcatt ttgtgtactg cttattatct agtgtttgaa aattgttgtt    33420
ttatgtaatt tggcttgttt tgttgtaggt gtttaaagtg aagataactg gttagtgtta    33480
ctccatcgtg gtggaaagtg tctcttcctc tttttataca ttctcttact tgtagatatc    33540
atcacctctg ttctcacgat ttcagttttg ttttggtttt tttttgtggg ggggagcttt    33600
tgtgggcatg gctcccaaat ctttatgtca ggactatttg cttagttcag tgcctgagtg    33660
ccttcattcc tgctagctgt ttccatttag cttttttttt ttttctttta tttcaaatgt    33720
aatactgttt ccttcgaaca acctctttct ttgtccctat ttctgttagc tgaaacatgg    33780
atgtctgagt cccagaggct agaatttctt ttagtcttct ggaatacatt tggtacctaa    33840
gttctctcat tctttccctc atggttttta tcttcttttt tataccctcc ctgccacaca    33900
cagacatcaa tttgtctaat tcccaacttt atataacctt ccatttaggc tactgcagca    33960
gcttcctaac tggcttccct gctttctttt ctctctgcag caattcaccc tgcaaattgc    34020
taccagaaca gtattcccaa aacatctgtc tgtcacccag aaatcaccag taccttgttt    34080
cataaattac caggtcttta tcctcttact tcaagttctt gatggagcac cctggctgtc    34140
cggtggttag gacttggtgc tttcactgat gtgagcctgg gttcatccct ggtttcgaaa    34200
cttaagatcc tagatgccac atggcatggc caaaaaaaaa caaaaaagtc cctgacaatt    34260
tgattgaatc tcactttcca gcattaactt ccattattta ctttttctgaa tccttcaccc    34320 cacctccaca gagttcccca ccatcctttg aatatgtctt acacttacct tcctgtactt    34380
ttacttggac ttttccctgt ttctttgtgc attctttaga atataactta aatttccttt    34440
tcctctttgc tcacctaaag cataccatcc cataatgatc actttcttta cactcctatt    34500
taaattctct actgtttcat agacagtgaa cagtgttttgg aattattaga tacttgatat    34560
gattttgtta cttctttcat tcttttaaaa tattttttttc ttggaagatg ggagggaggt    34620
ttcagaggga gggaatataa gtatacctgt ggctgattca tgttgatgta tggcagaaac    34680
cagcacaata ttgtaaagta attatcatcc aattaaaaat aaaattaaaa aaaattttttt    34740 ttcttgattt tcatctaaat tatcattctt gaaggaagag agaccgtgtt ttgtgtttct    34800
gtatattcct tgtaggacca tataattatg cttgtttata ataaaaattc ataaatattt    34860
attgatttat ttcagcttgg aaatatgaag acaatgtgtg ctggttgttc aggcactata    34920
atgagtttct tccttccttt tagacataaa attttttaaa agtatctggt taccattgac    34980
cttacagtat ataggatcag cagaaatgta tattacttgc cttatttgag aaaggagcag    35040
aaaacttttt tatcatttct ttttctatat ttatgctcct tttatttaaa acctctttag    35100
ttatttgagg caactgatca tagcttccat ttttcagacc tactttcaga tatcatcaag    35160
tattccccat tagttcttca aagttgttca tctaaagtta cagaaacttt tgactatttg    35220
tcctttctac ccgttcaaac cgtacaagga ctgctgaagg cagtgcaggt aagtcttttg    35280
actcctaagc agctcatgaa caaggttgca gtggaagtct gatgtatttc ttcataatta    35340
cgtatgtata agaaatcctg tttcccttga ttctaagaca gaaccttcta ttaaaagagc    35400
agaagcactg agctagggtt tattttccaa gtttatcccc tcttcatagt actattctct    35460
ctcctttgat tctgtttcaa gtcagtgaag taattgaaag gctcttagga aattattaat    35520
tgaagacaat agatataaag gtattcacaa ctagtttcaa tttagcatta gtattaactc    35580
ttcttattac taagtgcaat aaacattgca gcgtgtttat aaaatggaac caagcttttct   35640 taagccaaat ggtgacagta ttgaatagaa atgtgctaag gctaataaac aaattgctgt    35700
```

```
ttttaacact gattcttcct ctttcagccc cttctcaaag tcagcatgtc aataagagac   35760
tccttgatac ttgtccttcg gaaagccatg tttgccaggt atgtagcatc ccctgagatc   35820
ctaggaaatg acgctctcta atgttaccta aagtcctctc tgcagtcacc tctagtacag   35880
cagtcatgca aatttctaaa gcacgatcga gatgacagta ccatctccta aagggattat   35940
gagatgagta ctgtggaaag aatttgctac tttaaggata aaataccaaa ttattgtcac   36000
attgtccata ttatagtaca ctcatgggta ttcagaggag caactagtaa gcagccaaat   36060
gctgtttctc catgttgtag agcggacagt ttttgttagt cctttcccag aagcgtgtgt   36120
gataggccag cattgtatgt tgtagtctca gtgagatgaa tggtttctct ggatggaggg   36180
tttacaaggt gccaagcact gcactcctct aagtagaagg gaagtctcct ttagactcag   36240
aaaatcaaca atttcctttg ttgtttagta cttatgtttg acttatcaac tcattgtgca   36300
gcctctcagg actcttgttc tcactgccca caaaggcttg tcagcaggat agagaagagt   36360
agagatggtg tcatgaggtt aagtagataa aaacttcagc tgaattcctg tccttcctaa   36420
ttgatgtgaa cagctatgcc ttgtttagta tgtttatttt gctctgttct tcattgttaa   36480
tacacattct ttttctgtat aaaactaact ggattttttct gacacaaaag cttattcctg   36540
tgaaatcagt actgtttggt aacttcttct ctgtctattc ctgagctagc cagcttgatg   36600
cccgaaaatc tgcagttgct gggttttttac tgctattgaa gaacttcaaa gttttaggca   36660
gcttgtcgtc ttctcagtgc agccagtcta ttggtgttag ccaggtaagg acttttttttc   36720 acaccagctt atcatgtgtg tactgatgca gtagttgatg atgtaaagat ttttttactc   36780
gggttctggt tgtacagatg atcctgaaac tgaggatctg atgatgataa tatcagccat   36840
cacttactga tggcaaattt gctgtatggt agcctctagc ttcaagttgg ctcttgaact   36900
gtatgttgat tgaaatgtgg ctagttcaaa ttgagttgtg ctgtatatat aaaacaacac   36960
actggatttt gaagacttag tgtgagataa aagtgtaaaa tatatcataa ttttttattt   37020
tgattatgtg ttgagataat attttggctg tgttgggcta agtaaaatgt taaaattaat   37080
ttcaccaatt tcttttttact cttttgattt ggctattaga aaacttaata ttatatatac   37140
agcttgcatt tgtaatttgt attgtgtttc taatggacaa cactgtgcta gacactgttc   37200
tgagtgcttt acatttatttt tctcatttaa ccttcacagc agttctctag gtaaatactg   37260
ttactgtcct cagtttttaat agtttatttta tttgcacacc tgataaaacc tgtaatctaa   37320
gaaaacaaag cttttttacaa taatatgata atctaggctt tgcagcagta aaattgtcat   37380
ttaaattcag tactaatatg atttgtaaat aagagacatc tgtatagcag tttcttttagg   37440 aatcctttat tgctgttaca acagctcacc acttttgttt ataacttatg ccatagatta   37500
aatattagga acactggata tcatttatga atggctaata tccctatttt aaatataaga   37560
aaactgagac agagagaggt taataatttg ccctaagtga tatagccagt aaagtgtaga   37620
actaggattt gacctcagaa ggaaatggca acccactcca gtgttcttgc ctggagaatc   37680
ccagggatgg gggagctggt gggctgccgt ctatgggtc acacagagtc ggacacgact   37740
gaagtgactt agcagcagca gcagcagtat taactacctc actaagatgc ctgaaataag   37800
gattagggtt cttggtctat aattgctgaa attattatgt aaatcaaaca ggcagtatta   37860
ttctttgtca tgtccatatc taaacaaaac tacctgcctc taaacctctc aggagttcat   37920
ggaaccctca gaagagctca attctcagcc ttttaagtaa aattaagttt attatgacta   37980
ctaaattcta gtggcatgaa ataatctgtg tgccttccta agtaggtgac ttaggaatat   38040
```

```
tgtaccacat tgccaaggaa atcttaagg aatgagtaag ttaattttttt ttaagtgctt    38100 gaaaattctt attccaaaat agaataagat acttatcatg gcttgataat gattatagtg    38160
tctgcctcag ccctgggttt tgccatatgg ggaaagctaa atgtaaggtt ctttaaccaa    38220
aaataccagc tcattttact ccttaatgga actattaata cttactcagg taagatcttc    38280
atgaactgac ctctcttcct ttcaggtcca tgtggatatc catagccgtt acaattctgt    38340
tgccaatgag accttttgcc ttgagatcat ggatagtttg aagagatgct taggtcagca    38400
ggcagatgtt cgactcatgc tttatgaggt aaatcaatag ggtgaaagag atgtagtact    38460
ccactcccca actccactga tccttttaat tttaataatt tttcttacca gagtacagta    38520
gatatgctct tatttagtgc agtgaggact agtagttatt gatgcttggc caaaaattca    38580
ttgaaggtga ggaagcataa agaatagttg aaacatgtta aatgttttca tttgaaatat    38640
ttaaatgtac tgttaattta ccagccttttt gttttaagga aaagttcttt tgcttttgag    38700
tatgaaaaat actccagatt agtcttagta gagaaatctt ctaaatgtgt ttagtttttt    38760
ctgtttttag aattgtctta cccctccccc aatccatcag aaatcagttt tacagattta    38820
cttttattaa atatttccaa aatattcaac ttagttttca taaaaacaac ttcttggggt    38880
tttttgtttg tgtttttagt gggtttttggg ttttttttggc catgcttgca tgccttgtgg    38940
gatcttagtt ccctgaccag ggattgaaca cacacactca ggaatgaaag agcagagttc    39000
taaccgctga actgctaggg aattccccca gacagcttgt cattttgctc ttggtttcca    39060
acagtttaca gaatgtcttg agtagattac gtaatgacag tacaattagc aaaaaatgaa    39120
tggaacaaat attactactg acttgtaatt aggatatat tcagccagtg gaacaaaagt    39180
ctgcagtcat gggagactgc agtacaattt ctagcattta gtatgctttg tgcttcagca    39240
cacatatttt ataggatgga gaacattagg taatctagca ggtagattaa gtgcaagtca    39300
tttcagagca cagctatact ttcatttggc attttttaaaa tagcatttat tgagctactg    39360
tagttgccaa gcaccacacc tgacattgga ttttttcaggt ttattgtaaa aaatatagaa    39420
agtatagaaa aaattttttt ttattattac tagtcctacc actcatatgc atacttacac    39480
aaaattggaa tcatagattt ctctagcttt ttatctctta atattatgct gtaagcattt    39540
cctattttat taaatgttct ttgccacata attttgaatg ctaaaaagtg ctctttttgt    39600
atacagtaat ttatttaact ttttttttatt ttggggggcat ttttgtggct tccagttttt    39660
cactatgaat attgttgtac cacattgact gtttgacagt aatgtaccac tgtgaatgac    39720
cacattggcg ggttaaagat acaacatttt caggtctata gcatatgctg tcaagcagtg    39780 aattttttttt tttaatgatt aagaatacct ttgttttaac atttgtgatg aaaaatcgca    39840
gatactcttt gcaaatgagg attagagggg aaatttctca atttaataaa agggtctat    39900 gaatcctaca tctaattttaa atagtgagag aacttaatgc gtttctcctc tggtcaggaa    39960
caggatattt gttcacaaaa cttctgttct acattgaagt gaaggtctga tccaatgcag    40020
caaggcaaga aaaagaaata aaggcttata gatttgaaag tatgaagtaa agctgtcttg    40080
attcacatag tgtacataga ccataccaaa gagtctacaa aaaatgatat agtaaggttg    40140
tagaatacaa gatcagtaac catgtaatag tcacttatag ttctgcttac tagcaacaaa    40200
cagttcaaaa ttgaaagtag tatttatagt agatgaaaaa tacttaagga gaggttccac    40260
aaagtatatg caggatatgt acactgaaga cctcaaaata tcactgagag aaattaaaga    40320
agagttaagt aattggaaag atacgcagtg ttcacagaat agaataatca atattgtcaa    40380 tattttttaag tatcagaaag atctgtaaat tgagtgaaat cccaggcttt tttggtagaa    40440
```

```
attaagaagt tgattctaca agttatatgg catgtaagca cctctaagat gaacagcaca   40500
attgaaaagt ataaagttgg tcagtagagt tttgacaaag atcccaaggt aattcaatag   40560
aaagaggata gtcttttcaa caaacaatgc tggaacaatt gtactggcgg ggggtcccc    40620 aaagccacct ctatttaaaa atttctttag gagtcataaa acagaatgta tttgttctca   40680
tggctaagat tatagttaag aatacaaagc aaaaatagc acaagcaaga ggctcataga    40740
ggaaagtcct caggaaacca gattcctctt taagaacata aactatattg tttatacagt   40800
ttaggcacag taagcttctc attgttttgg gagttttata tcagtataag aaactgttga   40860
tcagccagat tcacagccac cagccaaagg gctaaccttt ccatggaagc ggaccttacc   40920
aaggatagca gtctcagact actaagttaa ctcttctcca cagtcatctg tattaaaaag   40980
aagaaatcct caacccttat ttagctccca atttaaaaaa ttactttgta atgtctcgta   41040
gtcctaaatc tgttaggata ttggtattca tttattcatc aaagacttaa gttagtactt   41100
ttgatttgta aaaaactcta cgtattatta acataaatac cttttgtcat acttgttgta   41160
agtacaggcc agattgccat ttgcttttt ttttttaatg ataatcattt tagagctaga    41220
aatttagatt ttacagtttg gttgtaatct tcacctttga gatacctact gtctctttg    41280 tgtggagtcc atatccttcc agtgaatatt tactagcatt ttcttttatt tttttaatg    41340 cttttgttta actaaattct tctgcagttt ttatattaat atataaagac ccaactcctc   41400
cgagattagc catttctttt ttcaggtata atatattgcc tctttcatgt gtactgagtc   41460
tttctgtttg tatgctatgc ctttattttt ctgtaatttt tgtgccagga acacagttgt   41520 cttttttatta ccattatact tttataaaat atcctaatac ttattagggc tgatcatcct  41580
ttgtttttta aaaaaaaat gggggggggt ggtcaattct cattttctgt ttctcactgg    41640
tagactgtat aacctctgtc tcaggttcca aaaagaaaag cgtccccagg attttaatct   41700
gagcagtttt aaactaagac tgggaaattt tggatgggaa gaaatgtcat agtcattcac   41760
attagggtgc ttaggtccag gaggcacttt tgaatcactg gagagtaggg gagtgcccta   41820
aaaaggaagg ctgctaatgt atgataagag gaaaaaatga ggtctgggaa agggaaaagt   41880
accccaaagc cagacgagac ctgatgtcta acagttgtga ggattatggt cagtttataa   41940
tccagttctc attgtcagag atctcacatt agcgtaggcc aataacctaa actttctgaa   42000
ttgtttctcc ctctagcata tacggcctcc atctttttt cagagagctg agaataggta    42060
aagaaacaca aagttatttt aaagttaaga ttgtgcaaat cactagtgac tctgatagag   42120
agcttatttg tcctctgatt ccttttaggg gttctatgat gtccttcgaa ggaattctca   42180
gctggctaac tcagtcatgc aaactctgct ctcacaggta aattatattt tcatggatat   42240
aagggaacag gtaccaaggc attaagtaat tgacatttt aataatttc aaaatataaa     42300 ataattccta agtagtccac tggtacgttg taaacatgcc tagggtacat gatgctatt    42360 catgttgttt tattttaatc actgtttatc tgtctaccat attgccattg tctgacaatt   42420
aaccttctca gttaacatcc taagtcagaa gggcattttg tagaaccatt tatacaaagg   42480
ccatcagtag tagtatctgt tatgtttatt tctgataaag aagagtgatt tggagaaaac   42540
agtaaaatat tgacatttct caaatctgag tgacatattc atgagtgtct cttaggttat   42600
tttctatatt tctcagcttt tttaaaaagc tgcaaattat gaaatatttc aaaggaccat   42660
caagatgaga agaatttagc tgaagagttt ctaatgtgaa taagaccttt ttactctcag   42720
catttattat taagcattta tttgaattag tgaattcaca aagtgcaacc atcaccagtc   42780
```

```
aattgagaac gttttatctt ctcataaaaa accacaccgt ttagctaccc cccccttttaa   42840 ttttcccatc cttcctcaaa ccttctaccc ctaagcaatc atcagtctta tttttctctc   42900
tatagatttg cctattctgg acatttcata taatagagtc aaacaatgtg tggtctttta   42960
tgactgactt ctttcactta acatgatgtt ttcaggggtc atccatattg tagggtgcat   43020
cagtctttat tccttttat ggctaaataa tatttcattg tatgatatat atatatttt    43080 tttttaatat atgttgagag agttcaagag actattatgt actaatagta ataacaacag   43140
tacttaatgt ttagcactta cagaggggca agcaatttat gaatggtata tggtggatga   43200
tctcatttag tcctcacaaa accctgtgaa ataactgctt agttccattt tacagatgta   43260
tgttttaagg ctccaagagg ttaagtaatt taatttgccc aaggtctcac agttaataag   43320
tgatggagct agaatttgaa ctcagatctg gctcaagagc tgaagcatgt gtttctccta   43380
tttggagttg attaagctat ttgaatcttt taagttgatg cttgtcacca aatttgagaa   43440
atgtccattc attatttcat cagattattt ttcctatcc cctctttctc tccttttctt    43500
ctggggcttc agtggtatgt atattggaat gcctgatact gttccacaga tcttggttca   43560
tttttcctca atattttac actgttttct tcagatttta tattttctca taatctgtct   43620
tcaagtttac tttcttctgc catttcagtt ctgttgtttt actcttgaat gcatgttaaa   43680
ttttatcaga tgttttctg tatctattga gatgaccata tgattttct cctttaatct    43740 gttaccgtga tgaattatat tatttgatct tttaaaaaaa cattgcattc ctagaataaa   43800
ctcaaattga ttatattacc ttttttatac actactgggt ttgatttcca tttaggacat   43860
acatacatct gtacaagaag gaatggccta taatttcat ttttcatact gaatttcttt    43920
ggtttagtat gagcttagta aaatgattgg ggatgttccc tcttttctg gttttgtaa     43980 aatttgaaat ttcctttatt ccatttcccc ccttacttgt ttcaaagtta aacactttct   44040
ttaaactttc agctatattg tctaatgatt tggacagtct taactctaaa ataaccctat   44100
atttgaagtc atgtgaattc tagcctcagc taactaactt atggttagaa agtccctgag   44160 aagactttc cccccttcacc tgaagtcaga ggtaggtagg taagtacata tcccctcact   44220
atcttcctcc atgtggtgga tttattttt aggttcatcc actaaggata tctgcttttg    44280
agaattccag cttttctgtga aggtctctga tacaatctca gatacaatct ctgatacaat   44340
ctagatataa tctctgatac aaccccatgc ggacccctagg ctctgtcttt aatttcatga   44400
tttcttttac tttcctttta tcttagctat ctatttaata aatgtatcta tataaaaatt    44460
ttaatgcagt gtttttat ctttactgcg agggtttctc taaaccctag cccaccattt     44520
tgctataaat ggtacttctc gtcccctctc gctcttcctc cttttttatg ccgttgcttt    44580
gtgctaattc tgctaaagaa gctccatttg gaagtggaga aatgattgga aggtcttaca   44640
ctatcaaaag ttttttcagtg gaccttggac ctgatcttat ataaaattta tatcttgtta   44700
tattttatct ttcaaactaa tgatcagtcc atctacattt gcacattaac atggcaagtt   44760
atgactgaaa gcatagagca gtgcttccca actcaggtta gtatgtggac caataaaatt   44820
atatagactc caaaagttaa aaagaggaaa atggcaatta acatttttttt ttatgaaagt   44880 atagttgatt tgcagtgtat ttgtttctgg tatacagcaa agttattcag ttacatatat   44940 attcttttc attatgagtt attacagtat attcaatata attccctgtg ctatacactg    45000
ggatcttatt tatctatttt atatataata gtttgtttct gctaatccaa aagtcctaat   45060
ttatcctttc cccaccccct ttcccttttg ataaccataa gtttgtttc tgggtctgtg    45120 aatctatttc tattttgtaa ataagttta tttgtatcat tttaaagatt ccacatataa    45180
```

```
gtgatatcat atagtatttg tctttctcag ttgacttcac ttagtatggt catctccagg    45240
tccatctatt ttgctgtaaa tggcatcatt tgattctttt ttatggctga gttaactaac    45300
tttttttgag ctctgttatg tgctaaatag tatttgaagc tccttacatg tgttagcaca    45360
tttaatcgta tacaaatgtt tatgcttata ttaataatat cctcatttca cagatgagga    45420
accaagacat ctacctttct tgaattaata agtagtggta ctgggatttt agattcagtc    45480
agtctgactc tggagcctct attcttatta accaagctgt actgaaagtg cttgatagcc    45540
tatacaaatt aaggaactgg tgtgagagag catggtgttt tataggagag gtgatgaagt    45600
ggactaggaa aggtgtcagt cagtgcactg cctgatgcaa gggcaaagga aggacagggt    45660
tgagccaaag caacagattt tcctgcagtg ttctttggac agttgggaaa caatgtctta    45720
gaaagcatta aacattaaag ttgccattag cttgaccagt taaaaaagtg aaaagcattc    45780
atgaaccgtg atgtcttttt ctttcccata cacagttgaa acagttctat gagccagaac    45840
ctgatgtact gcctcctctg aaattagaag cttgtattct gacccaagga gatcaggtct    45900
ttctacagga accactggtg agccattctt tcctcctccc ataaccatta ttttttactct   45960 taagtaaaac taccagccct attgatatgg ttgagcttca gaaagagatg acttctctgt    46020
gaaacacctg gtactcccag tgaattttta ctcttgactc ttccctgacc catcaccacc    46080
ttggttctgg tggtgagata tctgcatatc aacacttgac taataatcaa ggcatctatc    46140
acttctccca aggagcattt tacctcccat taatggctct ttgattgcaa gtactaaaca    46200
gatatacttt agaattggaa gaaggaggtt acccagaagc aggtgaaccc aggcgatctg    46260
cttcattagt ctggagtgta tgatttaggc tgagctagaa ctggcattct gttgaacctt    46320
cagagaaact gggacagttg gttttctatt ctcatctagc gggaagaaag aaactgaaac    46380
tcctgagtga cttacaacag atgtcctcag cctagagaga agctatggtg gtctcccaaa    46440
gattccctta acctaaatcc atatgttttgg aatagccttt gggactcaaa ggtgctgctg    46500
ctgctgagtc acttcagtcg tgtctgactc tgcatgaccc catagacagt agcccaccag    46560
gctcccttgt ccctgggatt ctccaggcaa gaacactgga gtgggctgcc atttccttca    46620
ccagtgtgtg aaagtgaaag tgaagttgct cagtcatgcc cgactcagtg accccatgga    46680
ctgcagccta ccaggctcct ccatccatgg gattttccag gcaaaggtgc tggagaggat    46740
ttaatttcac aacctggctc cttggtattt gtaccagatc agagatagca catttgatgt    46800
tacattctta ggtgtcagct acttgtgaaa ccactgtctt tgggaaaggc cagaaaacaa    46860
tgcctctgtt agttccattc tttttttctg ttttgtttg ttttaactc cagattgact     46920 taatttgtga tgctaatgaa taactttatt tagccttata gataaggatt atttgtcagt    46980
tatcaacagt ttgataggtt atcctttaac aagaatattc agttattatc tttttcttcta   47040 caggattatc tgctatgttg tattcaacac tgtttggcct ggtataagag cagagtggta    47100
ccattacagc aagaagaaga ggaggaggaa gaggggttct accaatactt agatgatatg    47160
ttggagtcga ttacgaatag aatgattaag agtgaactag aggacttcga actggtaatt    47220
gctaagtcta agctgtgttg agtaatggag gtttttagta gcttactaat ttttatcttg    47280
tgtcttttag gacaaatcag cagacttttc tcagagcact ggtattggca tcaaaaataa    47340
tatctgcgct tctcttgtta tgggaatttg tgaggttcta atagaatata atttcttcat    47400 aagtaattc aggtagggta tactctaact ctacttgtag ttcattttgt gtgtgggagt     47460 gtgtttctt aacactaaca ataggctagg tatgaacaga ctacagcgca tgacactctt     47520
```

| | | | | |
|---|---|---|---|---|
| agatggacct | ctagcctaag | accaaactat | gttctttcta | ccagggaaca tccaagcaca | 47580 |
| tgccaaacag | gctcgtgaat | tttgtctctc | catcaggctt | tactttactg aacattcccc | 47640 |
| agaccttgaa | cataacaacc | cctgatttta | atagagaaat | tttgattggt ggtagtattg | 47700 |
| aactttcatt | ctctgcaatg | actgatacaa | ataaaggggg | aaaagaaatg acccagttgg | 47760 |
| gtattaccta | ggagtactgt | gttaatagtg | aagatcgatt | catttgtaat attgggtcta | 47820 |
| aagtatgaca | tctaaagaag | tattgtgatt | tccttattac | tgtcttgaaa gtaaaccata | 47880 |
| atattctgat | gcctgtcctt | ggtggactct | ttccttttat | acagtaagac taagtttgaa | 47940 |
| acaattctga | gcttatttat | gtgttacaag | aagctctccg | acatccttaa tgaaaaatct | 48000 |
| ggtaaaggca | aaacaaaaat | ggccaaccga | ccaaccgata | gttttttgtc catgaaattt | 48060 |
| gtgtctgatc | ttctcacagc | tcttttcagg | taaggttcta | acacagggct aaagacagc | 48120 |
| cttaaggtga | gggttaaaaa | cacctactga | gggtcactga | tattacctag tttggattca | 48180 |
| caattcttag | catatataca | gtaaaaagta | agtcaacggg | gttgtaattt tcttgaaagc | 48240 |
| agaacacata | ggcatttaaa | gagatgcttt | gaattactaa | agggaacatc agaaacagtg | 48300 |
| aactagtgga | tgaaaagata | ggatagattc | caagaaatca | acctaagtag catgaaaaga | 48360 |
| agggaaagaa | aagcttgaat | ttaaaaaaaa | aggtgggggt | gacaacaaaa aaaacattac | 48420 |
| agaaagttaa | ctaagactga | cctttaaatt | tcatcaaagt | taaaggattg agggaagggg | 48480 |
| gagaaaggga | ggtaacgctg | agaataatat | ttgtagaaag | acagccttgg cagtgactct | 48540 |
| tggtgtgggc | tgcctggagt | ctgtcttttta | gaactggctg | ggtgctattg tgaactgtcc | 48600 |
| ctagaaaacg | taatttcaag | tcccagtagc | aggggaatct | ttctgtctct tttttcctgt | 48660 |
| ctagggacag | tacccagagt | catgaagaga | gcctgtctgt | tctgaggtcc agcaatgagt | 48720 |
| tcatgcgcta | cgcagtgaat | gtggctctga | tgaaggtcca | gcagctaaag gaaacagggc | 48780 |
| atgtgagtgg | ccctgatggc | caaaacccag | agaaggtctt | tcagaacctc tgtgacataa | 48840 |
| ctcggtaagc | cccacacacc | cttagagacc | tgttccactt | gctgtggcat ctccaagaga | 48900 |
| ggaaatcgac | gacggggggtg | gggagagaaa | ggtggtttga | agttgggtag ggagaaaggt | 48960 |
| ggtttgaagt | tcggcatacc | caaggtgga | agtgcagtca | ctcactatgt tgggggttttt | 49020 |
| tcctagtcct | gttttggtgt | ggattgttgg | ccacatataa | aatgttaatc taataccagg | 49080 |
| aataaaaagg | gatattacat | aatgactaaa | taattcatca | agcagacaga acagttttaa | 49140 |
| atgtatatgt | acttaatagc | acctaataac | agcttcagaa | tacttaaggc aaaaatggta | 49200 |
| atactgaggg | agaaatacac | aaataataat | ctacctctct | cagtaatcag tagaattaga | 49260 |
| tagaaaatca | gaaaggatgt | agaagactcg | aacaacacta | tcatccagct tgactttaat | 49320 |
| caatatttat | agaacattaa | ataagtattt | aagatagtga | gttattgcca gaatcagtgg | 49380 |
| aacagatggt | tcagaactga | tctacacaag | tatggtcttg | acttttgaca aaggtgccaa | 49440 |
| ggcaatggaa | tggagaaaga | aaagtctttt | caaacaggtg | tttctggaac aattgtacag | 49500 |
| gaatatgtga | aaaaatgaaa | ttaaaagaca | ctgtttggaa | gaaaagctat gcccaaccta | 49560 |
| gacagcatat | taaaaagcag | agacatgact | atgccaataa | aagtctgtct agtcaaagct | 49620 |
| acggtttttc | tagtagtcat | gtatggatgt | gagagctgag | ctataaagaa agctgagtgc | 49680 |
| caaagaattg | atgcttttga | atcagttggt | gtgttgaaga | agactcttga gagtcccttg | 49740 |
| gactgcaaga | tcaaaccagt | ccgtcctaaa | ggaaaccagt | cctgaatatc cattggaagg | 49800 |
| actgatgctg | aagctgaaac | tccaatactt | tggccatctg | atgtgaagaa ctgactcatt | 49860 |
| tgaaaagacc | ctgatactgg | gaaagattga | aggcaggaag | agaaggggaa gacaggatgt | 49920 |

-continued

```
gatgtttgga tggcatcacc gacttgatgg atatgagttt gtgcaagctc tgggagttgg    49980
tgatggacag ggaagcctag catgctgcaa tctatggggt cacaaagagt cagacacgac    50040
tgagcgactg atgtgaaaaa aaattgaact ttgatccatt tctcatgtta taaccaaata    50100
ttgaaatgaa tcagaggcat aagtataaaa ccaaatattg taaaacatct agaagacaga    50160
aaaaccttta caaccttgtt ttaggtaaaa aatttcctag gtataatacc agaagcacaa    50220
tcaatatttt ttttaaattt aactctgttc cttgaaaaac attcctaagg aaatttaaag    50280
acaagccaca aattaacagg aaatatttgc aaaacacgtg tctgatgatg gactggtaac    50340
cagagtatat aaagaactca aacttgttaa gaaaacaatc aaattgagaa atggataaa    50400
gtgttttaac agacactttta ccaaataaga tatatagatg gcaaataaga acatgaaagg    50460
gtgatcaaca taattagtca ctaggttagt gcaaattaaa atcacaatga gatatcacta    50520
aacacctaat ttttttttctt ttaaaaattt acttatttgt tttaattgga ggctaattac    50580
tttacaatat tgtggtggtt tgccatacat tcacatgaat cagccatgag tgtacatgtg    50640
ttccccatcc tgaaccgccc ccctccccc tatcccatcc ctcaaggtca tcccagtgca    50700
ccagccctga gcaccctgtc tcatgcatcg aacctggact ggcgatctat ttcacatatg    50760
ataatacaca tgattcaatg ctgttctctc aaatcatccc accctttgcct tttcccacag    50820
agttcaaaag tctgttcttt atatctgtat cttttttgct gtctcacata tagggtcact    50880
gttaccatct ttctaaattc catatatatg cgttaatata ctggattggt gtttttctttt    50940
ctgacttact tcactctata ataggctcca gtttcatcca cctcattaga actgattcaa    51000
atgcattctt tttaatagct gaataatatt ccattgtata tatgtaccac agctttctta    51060
tccatttgtc tgccgatgga catctaggtt gttttctttgt cctggctatt gtaaacagtg    51120
ctgcgatgaa cattggggta cacgtgtctc tttcaattct ggtttcctca atgtaaacac    51180
ctattaaaat gcctaaaagt ttagattgac tataccaaag tgttgtcatg gatgtggaag    51240
aatttaaact ctttgttttt tggttttttaa tgtttatttta tgtatttatt tttggctacc    51300
ctgggtcttc ttgctgtgcg ggcttttctc tagttgagtg agaggggggct actctagttg    51360
aggtacacgg gcttctcgtt gccgtggctt ctcatgttgt agaggacggg ctcttgagca    51420
cacaggcttc agtagttgca gctccgggct ctagagcaca ggctcaagta gttagttgct    51480
ccactgtatg tagaatcttc taagatcagg gatcaaaccc aggtctcctg attggtaggt    51540
ggattcttta ccactaagcc tccagggatg cccagaattt aaactctgat acactgttga    51600
cataaatgta aaatggtgca gccacttttgg aaaataattt gtcagtttct taaaaagtta    51660
agcacacacc tatcttacgg tacacccatt ccacctttct atccgtgtcc tccatctgtt    51720
cagttcttct cccccagtag ctaaatatct tttagtgtct tgtgtaaaga attctttat    51780
tcctgtacag caatatgaat atagcttctt atgctcaacc ctaccctctt cacacaaaag    51840
cttttttcagc atcctgcttt atttattat tacatttaac actgtattct ggacatctgt    51900
attctacagt aatcactgta ttctgggaaa tattttttata tcagttcaca gagaattttc    51960
atttagcctc tgaagttttt ttccctgac agatcaaaac ctgaattctt actggtcatt    52020
ttaccttaa acatcactgc atttcagtgt cttggtggct agaagcctat cccaaataac    52080
tgctgaagca gaaagctgag tgtgtgtcta gtgaaacatg acctactagt ccaaggcctt    52140
aagcttcccc aactctttc ttttgcccct ttctttttt ttcccctgc tccctttaa    52200
cctcctgtgg cctcttggtt cctaaaggct aatttgactg tcactgtggc caggatctta    52260
```

-continued

```
ttctcctatg cctctattag cttagtattc ttaaagatgt ctcagatgca gagagtgctg    52320
ggcatgggaa gaggaagaag ggcactttag ccccaaactg tggtgggagg ggccagggaa    52380
gctcaaataa cagcccagac cccaggacct ttggccctta atgagggcat ttgagaattg    52440
aatcataggc tatatttaag aaaagaatca gtaattcagc tcgtaacttt ggacttactt    52500
ttatgctgtt tttcagtaga gtaccacttt agatccaggc atatgtttta gtaggtgatt    52560
tgtttagact tgcaaaggcc tagagctctc ttagtctgat agcacctagg tctgtctttt    52620
gaatgtttct ataatatcct aatgatctcc agtttgtgca gatgttatcc tggacatcta    52680
agatttgcac ggaaaacagt tgcggtaagt ttcctgccat atttcctttt tcaggtttat    52740
ataaaatcat cagcaccaaa caacatttag aaaattacac attcaccgga gtatccaaaa    52800
cttcaaatac acaaaaccag ccccaagggt tggtaagaat acagtgcagt tgaacctctc    52860
attcactgct gctggaggtg tcagttggta taaccactct gggaaattat ttagcaatac    52920
ttaactacta aaattaaaca taggcttacg atcaagcagt tccactccca gcataagcag    52980
gtgggaaaat tctcacagca gtactgttct aataggcaaa accaaaccca gacgtctgtc    53040
agcagtcaaa tgggtcgagg ggttgcactg tgcgcgcagt gggacactgg acggcggtgg    53100
gagtgaacag actccactga cacgtgacat ggaggagtcc ggcgcacacg acactcagca    53160
gatggcagac acagacagag gacttactgc atggtgctac ttagatcgag ttcaaaatca    53220
gacaaaactc gatatgaggt tacaaggcag aatgacagtt tccttggtga ggaggggagt    53280
gtcctggggt gctgatattt cttgacccgt atgctagtta tatgttgaca gtgactaata    53340
aatgggaaac atccccctca tttgcacctg tgggtcgaag tgtacctttg tggacccgct    53400
gcctgggttg gagtgtgtgc agcatgggga tgttgtgcct gaaacatgac aggctagcat    53460
tccagccagg ccacccccac ccgctacagg actgacttgg gttataactg agttttcttt    53520
ccttcctact cctagaggat gcctcctttt gcaagggcat gctgagtttg ctcttcaacc    53580
tccatgtttc gtgtaagagt cctgttggtc tgctgcgtga cttgtcccag gatatccatg    53640
gacttcttgg agacatagac gaggtactgt agtgagcctt cagtatggag ccctgagttg    53700
ggagtagagg ccagggaac agccttactg tcattcatc tcacctctct ttccgttccc    53760
aggatgtgga agtggagaaa acaaacaact ttgcattggt gaatttgaaa acagctgccc    53820
ctactgtctg tgtaagtgtt gatccctggc acttgggaaa tagccttgtc atcccttcca    53880

ttttattccc tgtgaggagt gaattacagt ggctaaagtc ctgaggcctc taacccgccc    53940
actggtggcc gtggctatca tgttacacca gcagctgtgt gcagtgagcc atgccaggcg    54000

ттттттттcтт tcacagctgc ttgttctgag taaagctgag aaggtcctag aagaagtgga    54060
ctggctgatc accaagctta agggacaagc aaatcaaaaa atcataccag gtaacatggg    54120

ttgagggagg ggttccagga attgtgatca aagcaaagcc aactaaaacc tgaactggaa    54180
gagacataaa ggcagagccc ctgagctctg tctgtttgtt tgtgctagac ttcctaagta    54240
atgaaagtag aagatataat tattaatgta ttctgcatcc agacttccta gttaatgatg    54300

tttagttggt ttctaaatct ctttgacttg aactagaaaa taaggtcagt tgggtttgaa    54360

tgtgctaatt aacттcaтттт cctttcagaa gaggcctctt tcaggcagc ctaacaaac    54420 catcccatgg agaaaaccac catcatacag ttgggaactc tgctcacatt tttccacgag    54480
ctggtgcaga cagccctgcc atcaggcagc тgтgттggaca ccttgttaaa ggaccttggc    54540
aaaatgtaca ccactcttac agcacttgtc aaatatgtga gtatcggaga gtcagtcacc    54600
accatcattc tgccccaccc agccaggaca ctgcccctgg tgctgaacac cccagggcag    54660
```

```
aacccatgtc tacatctctg caagtcacag tttgaccagt agatggcagg tgactccaca    54720
ggcctggaaa taacagttga ggcataattc taaatctgtt tttagagctc catatttctt    54780
tagcatatga gcatgttgct catatgattg agtataatga atgtaaatgc ctcttaattg    54840
agtataattg agtataaatg ccttttcaaa caccttctaa gactcagtct aaactttagc    54900
tatagaattt aatctgattc caattacaca aaaagttaga caatttcaga ccagtctgga    54960
caccgaaagg gtatttgtcc tttaacaagt aggtgttaaa tgcctcacag gtcaggtaca    55020
cgagtaggga ataagtttat tttttgaaaa tacaaggtat acttgccctg agtttaagtt    55080
aatgcttctt agtatccgtt aacaagaaac ttttttttgta tttgcagtat tttgattctc    55140
agcagacatt caagagtgct aggaactacg taatttagat ccgattctag caatgaccca    55200
cattacttag gaaggcacgg acaaccaaag aaagatggtg gaccgcctca caccatgtac    55260
ccaaacagca gcgctgccat ttctgagaag gtgccgctct ggctatagtg tgtggctaac    55320
tagcttctgt ggtagaaata cggagaacct ctataatctt tattggcttt ttctaaaaga    55380
aaaacagcaa agtcattggc tttctagatt cagggactat caccctgaag gattttttaaa    55440 gcaataaatg gaacaagtca gaaacttaaa tctttcattg cctcctgtct gggaagcttt    55500
ggagcttagg ggagggaaaa aaggaagcct ggagtcttaa gattctgcac gaatctgggt    55560
agcttatttt cttttcctct ctccagccag agcaatagtc atacaccatg tgctcactga    55620
gtcactacct gtagtttcat gggacatctg tgtaggaata gcattctaaa tctggattcc    55680
caggtggctc agtgataaag aatctgcctg ccaatgcagg aaacgtacga gatgcaggtt    55740
caatccctgg gttggaaagt atcccccagg gtaggtaatg gcaacccact ccagtattct    55800
tgcctgggaa atcccatgga tggaggagcc tggtgggcga cagtccatag ggtcacagag    55860
ttggacatga ctgagtatgc atgcatgtaa gattccaacg ctttccccta gaactttatg    55920
aaacctttga gagaagtggg tgtcctgcca ttgcctaata ctgaatcttg gaatcttttg    55980
ttagtatctc caggtgtatc agccctccac aggaattccg aaaaatatgg aaaaactggt    56040
gagttgagaa tgccttttcct aggaatgggg aaagcatctt attcctacag ttactgaatt    56100 cttctctcctt tgctgcaggt gaagctgtct ggttcacatc tgacccctct atgctattcg    56160
tttatttctt atgtacaggt aagtgattgt ctgtatcaca gtgtatcttc aagtgagaaa    56220
ggactccttg tattcccagg ggactgatca ctaagtttga tttagagaga aaaagtgttt    56280
ggtatgcttg cacttggagc agaggagaaa catgcatcct taggctcagt gacttggtct    56340
atttctgggt gattccaaac ccactccttt gggaatgtga gtgaagtagt agcaggcatg    56400
gtgaggctaa atgaggtaac ttgtggaaag tgcttaacac aacaccaggc aggtgttctc    56460
taaatatttg ctgttccaat aaaatgaaca tgacccttaga gcatcatttc ccaagctgtc    56520
agacataagg ccaaaaacag aaaggttaag attccgagct tctgatatag ggggcgtggg    56580
tttgatcact ggttggggaa ctaacatccc acgtgctgtg tggtacggcc agaaaaaggg    56640
gcaaagctga ggttcgaact gggttctttg actccgtgac agtggtctgc aaactttctg    56700
caaagggcca gatggtaaat gctctgggtt ttgcaggcca tagagtcact gtcacaactc    56760
aactctgccg ttgtggaata aaagcaccca tagtcaatat acaatgaagg agcttggctg    56820
tgttcagtga aacttctgaa aaacaagcag gagctggatt tggcctcttg gttgtagttg    56880
gccagcccct gctctggaag catacttgac actcactgac ttgtaaaatg ctgggaggtt    56940
tgggtttttg tgtttgaccc attctcaagc ttttcttctg cttatcacta ggcaccttcc    57000
```

```
agactatctt tttttctaca ttacacaaaa actggtttat gtattcttcc ttggatattt    57060
ctccccttct caatctgtgt ttgacttaaa gccttatttg acaaatcagc tgatccacag    57120
gcacttttg tctttgtgag atgtgcttaa tgagtcaaga gcccaaggtt ccattaactc     57180
tctccaactt ttatctagaa atctggattg catttgccac atctttcaaa gagctgctta    57240
ttctctttta gctccttttt tcccatagcc ttggatctca gtgagaagaa agcagtgaaa    57300
gccattgctc caaacccgt agcttagcat cctgctcagg actgtatacc tttaaaagat     57360
acttctcttc ccactacagt tttagtcctg cctgaatcag cagaaacagg ccatagctgg    57420
gattgattta gggagtttca acaaggtccc atctggggta caacttttag gaagatggct    57480
cacttcccat ttggtcacat gagttctact acctgtgctg cttctctgcc cctcccctac    57540
aaagtattca ccctctaccc tgccttccag ggccaaaaat aagtttcttc acaccagcat    57600
ctctgggatc cctacatttt cttatttcc agaacatgcc atgtgaacca agcctcctct     57660
ctctcacatg gctgtagtag tgtgattcct ctctgtttgc aggcctctgt ttttaactgt    57720
tagttgtccc atgggccgtg gtctgtcatt cctagagggc acagaactcc ccttcaagta    57780
aaaggttcct gtttgtgtgc ctcacacttg ggtggtctct gcctcacgtg tcccttctct    57840
cctgccttat cagaatcctg tacttcctgg tcccttctt gattgttcct ttctccagga     57900
gcccctttatt ttgattatct gcaacatagg gaaacaaagt gtttctatga cctttaaacc   57960
gtcctggagc ctgtaaccac ttgtcatgtg agacacatgg ctctgagaac aacctctcca    58020
gcttcctatc ttttctctag cccttttagc gaatatccca gtagtgaaca cctagtccta    58080
ctcccccctt gacagttctt tgtagctcat gagtcccttg gctgccctag tgttaataac    58140
ggtgggtcct aacctcactt ccctgtgata gacccatcca agagcaagac tgtaaatctc    58200
ccaacaacaa aaagcgggaa aatatctgag gattatgaag tgtcccagaa tgtttcccat    58260
tgcccagcat ctgcttcagg agaatctctt cacccagact tggcccccta agagttctcc    58320
cgttatcgct ataatcatcg tattagaaaa ttaccactag cctggtagct ctacagaaaa    58380
accttcagga atgagagaac ttgtttcctt ttctttagaa caagcacagt aggagcctaa    58440
aatgtaccgg agaaaaggag aaaaccgctg ccggccccac agccatcgta agttgctgac    58500
agtgaccaag acgtggccac tgggaattcc ctggtggtcc agtggttggg actctgcgct    58560
tccactgcag gggggcacca gtttgatccc tggtcaagga actaggatcc tgcatgccgt    58620
gcagtacaac aaaaaaaaaa aggttgctaa tgaaccttga aaatacgtta agtaaaagaa    58680
gccagtcgga caaagactag gtgttatatg aatccattta tataaaatgc ccagaaaagg    58740
caaatctaaa aagattagtg gttgcctaga actggggagc aggagtggtt aggggatgt     58800
tagagaaact gggaaggtgc ctgctaaaat gggtatagga tttcttgtgc aggtgggttg    58860
tgtgaaaatg ctgtaaaatt atggtgatgg ttatacaact ctgtgaatgc acaaagaaac    58920
acacacaaaa aagcatgcaa tataatgggt aaatggctgg tatgtgaatt acatctcagt    58980
aaagctgggg aaaatgtgct tatttgtgta tggctgcttc tcaactcatg gactttgttc    59040
aaatggaaca tcttttcct ctgtatatgc tctattcagg aagtaccagg aaatcttgaa     59100
ctcttcaaaa atagaaatag cttaggataa ccactgggaa ggagctgatt ttaggaaaag    59160
ttagtgagtg caaaaggtgc cccttaaagg atgtgaaaga ttggtgccgg aaagtggatt    59220
ctccagggta ctgctggcaa agtaagaatt gagtcctctc tcaaggggaa catttagcaa    59280
taactgttca catgcaccag tctttaatgc agcaattcta cttgtagaat atctctattg    59340
tcaaggcctg tgtatattca gtcctagtaa tgttgtaagt aaaagtgaaa tactgggaaa    59400
```

| | | | | |
|---|---|---|---|---|
| actaagatgc | ccacaataga | gggctggctt | ttacagtata | tttatactgt agaacaaact | 59460 |
| atgcagacat | gaaaaaatac | aaagctaaat | gttcagatac | agaattctaa gataatgtta | 59520 |
| aagaaaaaaa | agatgtaaag | tgtcttcatt | tgtagtttaa | aaatataaa aacatgtcta | 59580 |
| tatgcataag | aaacatatgg | aaggatctac | aagctacaat | tcaagttgag gggagagaga | 59640 |
| atcgcagcta | tgaaaacgca | tctgtagact | agagcggaag | cagagccagt gcagaggggc | 59700 |
| tcatcatcac | aagaatccca | agtcagagag | gcagccagac | acccacacca cggcccttcc | 59760 |
| ctcagccagc | ctctagaaaa | cacaggttta | ggaattacaa | gtagaaagga ttaattgcca | 59820 |
| tctccattag | catttaggtc | ctttgatgaa | actgaactgt | caaaaaaaaa tcttaatgac | 59880 |
| tggtgtataa | gtaaaactgc | atttcattgg | aagttagact | ctctttccct caaagccaca | 59940 |
| agcagttctg | ctataggcag | tttcagagca | ctttaccacc | cctgaacccc aaatttaggt | 60000 |
| cttctcttct | ttgccctgta | ggccagagct | cttcgggaaa | ccaagccaat tcctaatctc | 60060 |
| atctttgcca | ttgaacagta | tgaaaaattt | ctcatccacc | tttctaagag gtcaaaggta | 60120 |
| agcatattct | gtaattttc | tactgatttc | cacttagcct | gtgagggac ctggcaaact | 60180 |
| gaagcaacac | aactgcactg | gggggaggcg | actgcgtttc | ttttgtttct ttgctatttc | 60240 |
| tgatctgatg | gcctgaagcc | aaacattgac | acaggggacc | tgatgtgaag tctagtgggt | 60300 |
| gtgtacttgc | ttctctagga | actgaagggt | ttatccggga | tggcttaggc agtcctgggc | 60360 |
| aggttttatt | ggtggcaaac | tgtgcctgtg | tttacaatcc | tgtcccaggt gaacctgatg | 60420 |
| aagcatataa | agctcagcac | ctcacgagac | ttcaagatca | agggaaacat cctggacgtg | 60480 |
| gttcttcggc | aggaggagga | tgaaaatgaa | gaggtcagtg | cctgctcaga ctagagtgca | 60540 |
| ggaggcttca | gctgccctcc | tggctggctg | tcagtagcct | gtcagggagc agccacagag | 60600 |
| aaagagccaa | aaggtggtca | aagacgaaac | taagcattct | caagagaaag gttgtaaacg | 60660 |
| gtgaaccatc | cccgaagttt | cccaggcttg | tatacccttta | gggtggacat ttccagaaag | 60720 |
| ggaatgttga | aaacaaggtc | ttactgtggg | tcttctcccc | ataacctttt aaaccattgg | 60780 |
| aaaattatga | gcctaagcac | tctggctcag | aaaccagttt | ttccctcttc taccatgctg | 60840 |
| tcattcaaag | tagggccact | actctgaatg | agggtcagca | catttcttag cctcctttcc | 60900 |
| cctctgctga | gactaaaggg | agaggaacag | cacgctatga | gccctacagc atctctgaag | 60960 |
| cagaacccag | tgtttcctta | cctctggtgc | ccagaatttc | tatcacctta catatatcca | 61020 |
| agataaactg | gaagttgaca | tcaaccaccc | tggatttcta | gcttctcaaa aaatcctgaa | 61080 |
| tctacattct | tccatttacc | acactctaag | ccataataca | cctggccctg tccactgcct | 61140 |
| ctgcctccct | ggcatttgag | ttcaggggag | ttctgcagca | tcttgatgcc ccttctctgt | 61200 |
| caccgtgttc | cctgcgtcat | tacagaagtc | caaaggaag | gagtcagcac caccttgctc | 61260 |
| tgctgcagag | cttgccccca | tctccaacag | ttacctcccg | tgagtgggac ggggagaaa | 61320 |
| gcatgaccaa | cacaggcttt | gatgagaaga | taaggattt | ctgttttat ttccactgcc | 61380 |
| tctgaacagg | cttctcatgt | tacagcgtta | cttctctccc | cttctagggc actgcatcag | 61440 |
| agcatgaggg | gcagaacaaa | gaaccagcca | agaagaaaag | gaaaaggaa atgaaatgcc | 61500 |
| tgagttaatg | tgaactttgg | ggcttctgct | ttcttttac | ccaacaagca acaatgcccc | 61560 |
| cttgtcctgc | tgcctgcacc | acattggcat | cttggttctg | aactcaattg caccttcagt | 61620 |
| ttagaggcaa | tcattcttgg | caggctctgc | tactgaaaaa | tggctggcct caggccagcc | 61680 |
| cttttgcaaa | aagcagagct | gaaagcctga | gtttaggag | cctgcactgc cccaatgaag | 61740 |

```
ctccatggga gcaaatacag agcctccagg cagggctata gtccaggctg gcttcatttc    61800
tccagggagc ctttggtgag ttcaattatc tggtaaatat ccagcgcttc acctgaaaaa    61860
tagtgcaatt cgttaggatg cccctcacg aagcagtcag aagtgagaaa cgcttaatgt    61920
taaggtcaaa aaggattgcc aagaatggta gggtcatatt tggggaggat ctgttttctt    61980
tatttataaa atgtttgtct tagatacatt ttaaatagac tttaagcttt ctaatttgtt    62040
tggcattcag agcataattt tgtcacctaa gaacccactg tgactttaaa ataaatctcg    62100
tttaaatctt ttgtgtgtgt gtgtgtggtt aaagaagaaa gaaaccggag tcaaacactt    62160
cgtttactag gaacatcttt ctagaaacac atgcctttgt gatctgaaca ttatgctcac    62220
tttggactca gggcccgtta taaaccgaac cagcccagta catagcccaa gatagggtt    62280 accctccagt ccccaagcct ctgttgtctg agaccacttt ctagtccacc tcccgtccca    62340
tgtgtaataa ggaaggaagg tgttgtgctc a                                   62371
```

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgttagccca gcagagga                                                  18

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
attctgaatc cactagatgt c                                              21

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcacacacct atcttacggt ac                                             22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gggagaagaa ctgaacagat gg                                             22

<210> SEQ ID NO 7
<211> LENGTH: 24
<212> TYPE: DNA
<213> ORGANISM: Artificial Sequence

```
<220> FEATURE:
<223> OTHER INFORMATION: Description of Artificial Sequence: Synthetic
      probe
<220> FEATURE:
<223> OTHER INFORMATION: N-term HEX; C-term IABkFQ

<400> SEQUENCE: 7
agtcccagtg tggctaagga gtga                                          24

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: N-term FAM
<220> FEATURE:
<221> NAME/KEY: misc_feature
<222> LOCATION: (9)..(10)
<223> OTHER INFORMATION: A ZEN quencher is present between these two
      positions
<220> FEATURE:
<223> OTHER INFORMATION: C-term IABkFQ

<400> SEQUENCE: 8
ccattccacc tttctatccg tgtcct                                        26

<210> SEQ ID NO 9
<211> LENGTH: 33
<212> TYPE: DNA
<213> ORGANISM: Bos taurus

<400> SEQUENCE: 9
ttacggtaca cccattccac ctttctatcc gtg                                33

<210> SEQ ID NO 10
<211> LENGTH: 34
<212> TYPE: DNA
<213> ORGANISM: Bos taurus

<400> SEQUENCE: 10
ttacggtaca cccattccac tcttaggtat ttac                               34

<210> SEQ ID NO 11
<211> LENGTH: 34
<212> TYPE: DNA
<213> ORGANISM: Bos taurus

<400> SEQUENCE: 11
aaatttgcag gaaatggtca cctttctatc cgtg                               34

<210> SEQ ID NO 12
<211> LENGTH: 70
<212> TYPE: PRT
<213> ORGANISM: Bos taurus

<400> SEQUENCE: 12

Tyr Ala Val Asn Val Ala Leu Met Lys Val Gln Gln Leu Lys Glu Thr
1               5                   10                  15

Gly His Val Ser Gly Pro Asp Gly Gln Asn Pro Glu Lys Val Phe Gln
            20                  25                  30

Asn Leu Cys Asp Ile Thr Arg Val Leu Leu Trp Arg Tyr Thr Ser Ile
        35                  40                  45
```

```
Pro Thr Ser Val Glu Glu Ser Gly Lys Arg Glu Lys Gly Lys Asn Ile
    50                  55                  60

Ser Leu Leu Cys Leu Glu
65                  70

<210> SEQ ID NO 13
<211> LENGTH: 65
<212> TYPE: PRT
<213> ORGANISM: Bos taurus

<400> SEQUENCE: 13

Tyr Ala Val Asn Val Ala Leu Met Lys Val Gln Gln Leu Lys Glu Thr
1               5                   10                  15

Gly His Val Ser Gly Pro Asp Gly Gln Asn Pro Glu Lys Val Phe Gln
            20                  25                  30

Asn Leu Cys Asp Ile Thr Arg Leu Cys Arg Cys Tyr Pro Gly His Leu
            35                  40                  45

Arg Phe Ala Arg Lys Thr Val Ala Arg Met Pro Pro Phe Ala Arg Ala
    50                  55                  60

Cys
65
```

DETECTING THE BRACHYSPINA MUTATION

CROSS-REFERENCE TO RELATED PATENT APPLICATIONS

This application is the U.S. National Stage of International Application PCT/EP2011/066524, filed Sep. 22, 2011, which claims the benefit of U.S. Patent Application No.: 61/485,915, filed May 13, 2011.

SEQUENCE LISTING

The instant application contains a Sequence Listing which has been submitted electronically in ASCII format and is hereby incorporated by reference in its entirety. Said ASCII copy, created on Apr. 7, 2015, is named 028622-0280_SL.txt and is 170,361 bytes in size.

FIELD OF THE INVENTION

This invention relates to methods for the detection of a bovine that is affected by or carrier of brachyspina, an inherited defect with autosomal recessive inheritance. The present invention provides methods for determining whether a bovine is affected by or carrier of brachyspina by analyzing its genomic DNA or its RNA. The methods include obtaining a sample of material containing genomic DNA or RNA from the bovine, and genotyping said nucleic acid for the presence of a 3.3 Kb deletion (nucleotide positions 20537017 to 20540346 in the bTau4.0 genome build) eliminating exons 25, 26 and 27 of the bovine FANCI gene, the mutation causing the brachyspina syndrome.

DESCRIPTION OF THE BACKGROUND ART

Marker Assisted Selection Against Genetic Defects in Livestock.

Intense selection for desired characteristics in livestock often results in increased inbreeding which contributes to the emergence of novel recessive defects. Examples of such outburst in Holstein-Friesian cattle include bovine leucocyte adhesion deficiency (BLAD)(1) and complex vertebral malformation (CVM)(2). Calf mortality resulting from such defects causes important economic losses and raises welfare concerns.

Most inherited defects are autosomal recessive, and are typically due to loss-of-function mutations (symbol "d") in essential genes. Matings between animals that are healthy but carry one copy of the mutation (genotype "+/d", i.e. "carriers") will yield 25% of homozygous mutant animals (genotype "d/d") that will be affected. A diagnostic test that allows the identification of +/d carrier animals, can be used either to cull carrier animals thereby eliminating the mutation and hence the defect from the population, or to avoid "at risk" matings between carrier sires and dams. The recent development of highly effective genomic tools, now allows for the rapid identification of the causative "d" mutations at the molecular level (3). Once identified, effective diagnostic tests can be developed using a range of generic DNA-based technologies that are well known by the people skilled in the art.

The Brachyspina Syndrome and Locus.

Recently (4) a new genetic defect, referred to as the brachyspina syndrome, was identified in Holstein-Friesian dairy cattle. Affected animals are characterized by severely reduced body weight, growth retardation, severe vertebral malformations associated with a significant shortening of the spine (brachyspina) and long and slender limbs. In addition, affected animals exhibit inferior brachygnatism as well as malformation of the inner organs, in particular the heart, kidneys and testis. All reported cases traced back on both sire and dam side to a common ancestor, suggesting autosomal recessive transmission.

We previously positioned the brachyspina locus in a 2.46 Mb genomic segment on bovine chromosome 21 (5) using recently developed 50K SNP arrays and a statistical approach called "autozygosity mapping" (3). Based on these findings, we developed an "indirect" diagnostic test on the basis of a panel of SNP markers spanning the brachyspina locus. Such an indirect test, often referred to as haplotype-based test, can and has already been used to detect +/d carrier animals. However, because the association between the disease causing "d" allele and the SNP alleles is not perfect, such indirect test suffer from a lack of senstivity and specificity. Some homozygous +/+ animals may erroneously be called carriers, while some +/d carrier animals may be missed. Improved diagnostic tests, ideally based on the detection of the causative mutation hence having near-perfect sensibility and specificity, are thus needed.

Effect of the Brachyspina Syndrome on Fertility.

We previously (5) reported that cows inseminated with sperm from sires that carry the brachyspina mutation show a decrease in non-return rate (the fact of not returning into heat as a result of successful pregnancy), an increase in stillbirth, and an increased culling rate. All these features are thought to result from embryonic and fetal mortality of ~4% of conceptuses. In addition to causing the brachyspina syndrome, the brachyspina mutation or mutations thus has/have an important effect on male and female fertility, two of the most important economic traits in dairy cattle breeding. Being able to detect the brachyspina mutation(s) via an appropriate diagnostic test would thus have an important impact on improving fertility in Holstein-Friesian dairy cattle.

SUMMARY OF THE INVENTION

In view of the above, the technical problem underlying the present invention was to provide means and methods that allow for a selective and convenient diagnosis of brachyspina or of carrier-status for this disease in cattle. The solution to said technical problem is achieved by the embodiments characterized in the claims. The present invention provides for the first time the identity of the mutation causing the brachyspina syndrome in cattle.

Thus, the present invention relates in a first embodiment to a method of detecting brachyspina syndrome from a bovine biological sample comprising genotyping a polynucleotide, DNA or RNA, for a deletion causing Brachyspina. In particular the present invention provides a method for determining whether a bovine is affected by or a carrier of brachyspina (BS) by analyzing its genomic DNA, the method comprising the steps of:

a) extracting the DNA from a sample of biological material containing said genomic DNA obtained from the bovine, b) genotyping said DNA for a deletion in the interval between nucleotide positions 20537017 to 20540346 on bovine chromosome 21 (bTau4.0), and c) determining whether said animal carries the brachyspina mutation.

Equally preferred is:

A method for determining whether a bovine is affected by brachyspina (BS) or a carrier of brachyspina (BS) by analyzing its genomic DNA, the method comprising the steps of:
a) obtaining a sample of material containing said genomic DNA from the bovine,
b) extracting the DNA from said sample,
c) genotyping said DNA for a deletion in the interval between nucleotide positions 20537017 to 20540346 on bovine chromosome 21 (bTau4.0), and
d) determining whether said animal carries the brachyspina mutation.

The term "bovine" in accordance with the present invention encompasses all cattle or cattle breeds from the species *bos taurus*. In a preferred embodiment of the methods of the present invention the bovine is selected from the group consisting of Holstein, Friesian and Holstein-Friesian Cross breeds, British and/or Dutch Friesian.

The term "carrier of brachyspina" refers to a bovine that carries the mutation causing the brachyspina defect on one of its chromosomes (whether inherited from sire or dam), and a wild-type allele on the other chromosome.

The term "sample" or "biological sample" according to the present invention refers to any material containing nuclear DNA from said bovine to be tested. In a preferred embodiment the biological sample to be used in the methods of the present invention is selected from the group consisting of blood, sperm, hair roots, milk, as well as body fluids including nucleated cells. Even more preferred as a biological sample is a tissue or tissues including nucleated cells.

Thus, in a further embodiment a method is provided for determining in a biological sample whether a bovine is a) unaffected b) has brachyspina or c) is a carrier of the disease.

DNA extraction/isolation and purification methods are well-known in the art and can be applied in the present invention. Standard protocols for the isolation of genomic DNA are inter alia referred to in Sambrook, J., Russell, D. W., Molecular Cloning: A Laboratory Manual, the third edition, Cold Spring Harbor Laboratory Press, Cold Spring Harbor, N.Y., 1.31-1.38, 2001 and Sharma, R. C., et al., A rapid procedure for isolation of RNA-free genomic DNA from mammalian cells, BioTechniques, 14, 176-178, 1993.

The term "brachyspina mutation" or "brachyspina deletion" or "deletion" in accordance with the present invention refers to a deletion in the interval between nucleotide positions 20537017 to 20540346 (bTau4.0) on bovine chromosome 21. Thus, in a preferred aspect the deletion encompasses 3,329 base pairs (also referred to herein as the 3.3 Kb deletion) spanning nucleotide positions 20537017 to 20540346 on bovine chromosome 21 (bTau4.0) in the bovine FANCI gene. Preferred deletions remove exons 25, 26 and 27 from the bovine FANCI gene. The brachyspina mutation/deletion is predicted to cause a frameshift at amino-acid position 877 substituting the 451 carboxyterminal amino-acids with a 26-residue long illegitimate peptide. Moreover, the ensuing stop codon in exon 28 is expected to cause nonsense mediated RNA decay.

The term "genotyping said DNA for the brachyspina mutation" or "genotyping said DNA for the brachyspina deletion" in accordance with the present invention refers to a method for determining or identifying whether a particular nucleotide sequence is present in a DNA sample. There are several methods known by those skilled in the art, e.g. (6) for determining whether such nucleotide sequence is present in a DNA sample. These include the amplification of a DNA segment encompassing the mutation by means of the polymerase chain reaction (PCR) or any other amplification method, and interrogate the amplicons by means of allele specific hybridization, or the 3'exonuclease assay (Taqman assay), or fluorescent dye and quenching agent-based PCR assay, or the use of allele-specific restriction enzymes (RFLP-based techniques), or direct sequencing, or the oligonucleotide ligation assay (OLA), or pyrosequencing, or the invader assay, or minisequencing, or DHPLC-based techniques, or single strand conformational polymorphism (SSCP), or allele-specific PCR, or denaturating gradient gel electrophoresis (DGGE), temperature gradient gel electrophoresis (TGGE), chemical mismatch cleavage (CMC), heteroduplex analysis based system, techniques based on mass spectroscopy, invasive cleavage assay, polymorphism ratio sequencing (PRS), microarrays, a rolling circle extension assay, HPLC-based techniques, extension based assays, ARMS (Amplification Refractory Mutation System), ALEX (Amplification Refractory Mutation Linear Extension), SBCE (Single base chain extension), a molecular beacon assay, invader (Third wave technologies), a ligase chain reaction assay, 5'-nuclease assay-based techniques, hybridization capillary array electrophoresis (CAE), protein truncation assay (PTT), immunoassays and solid phase hybridization (dot blot, reverse dot blot, chips). This list of methods is not meant to be exclusive, but just to illustrate the diversity of available methods. Some of these methods can be performed in accordance with the methods of the present invention in microarray format (microchips) or on beads.

The invention thus also relates to the use of primers or primer pairs, wherein the primers or primer pairs hybridize(s) under stringent conditions to the DNA corresponding the brachyspina deletion (nucleotide positions 20537017 to 20540346 (bTau4.0) or flanking it (i.e. for instance nucleotide positions 20527017 to 20537017 and 20540346 to 20550346 (bTau4.0), or to the complementary strand thereof.

Preferably, the primers of the invention have a length of at least 14 nucleotides such as 17 or 21 nucleotides.

In one embodiment of the diagnostic test, two primer sets are simultaneously used to respectively amplify the wild-type and the mutant allele. The corresponding amplicons are respectively detected using a 5'exonuclease assay using internal primers that respectively recognize the wild-type and mutant allele under stringent hybridization conditions. "Stringent or highly stringent conditions" of hybridization are well known to or can be established by the person skilled in the art according to conventional protocols. Appropriate stringent conditions for each sequence may be established on the basis of well-known parameters such as temperature, composition of the nucleic acid molecules, salt conditions etc.: see, for example, Sambrook et al., "Molecular Cloning, A Laboratory Manual"; CSH Press, Cold Spring Harbor, 1989 or Higgins and Hames (eds.), "Nucleic acid hybridization, a practical approach", IRL Press, Oxford 1985, see in particular the chapter "Hybridization Strategy" by Britten & Davidson, 3 to 15. Typical (highly stringent) conditions comprise hybridization at 65° C. in 0.5×SSC and 0.1% SDS or hybridization at 42° C. in 50% formamide, 4×SSC and 0.1% SDS. Hybridization is usually followed by washing to remove unspecific signals. Washing conditions include conditions such as 65° C., 0.2×SSC and 0.1% SDS or 2×SSC and 0.1% SDS or 0,3×SSC and 0.1% SDS at 25° C.-65° C.

The term "base positions 20537017 to 20540346 on bovine chromosome 21" refers to the *Bos taurus* reference sequence (bTau4.0) which can be retrieved from e.g. the UCSC, Ensembl, and NCBI genome browsers. The Btau_4.0 was generated by the Atlas genome assembly system at Baylor College of Medicine Human Genome Sequencing Center. The sequencing strategy combined BAC shotgun reads with whole genome shotgun reads from small insert libraries as well as BAC end sequences. The nucleotide reference sequence of the present invention spanning base positions 20156961 to 22499122 of bovine chromosome 21 (bTau_4.0) as referred to herein is included within the scope of the present invention and shown in SEQ ID NO.: 1 of PCT/EP2009/058190.

The wild type allelic sequence of the bovine FANCI gene is provided herewith as SEQ ID NO: 1. This sequence is located in the interval between nucleotide positions 20,485,327 to 20,551,026 of the reference sequence bTau4.0 on bovine chromosome 21.

An exemplary and particular preferred mutated allelic sequence of the bovine "brachyspina mutation" or "brachyspina deletion" in accordance with the present invention in the FANCI gene is provided herewith as SEQ ID NO: 2. This sequence is located in the interval between nucleotide positions 20,485,327 to 20,551,026 of the reference sequence bTau4.0 on bovine chromosome 21.

In a further embodiment of the present invention a method is provided for determining whether a bovine is affected by or a carrier of brachyspina (BS) by analyzing its genomic RNA, the method comprising the steps of:
  a) extracting the RNA from a sample of biological material containing said genomic RNA obtained from the bovine,
  b) genotyping said for a deletion in the interval between nucleotide positions 20537017 to 20540346 on bovine chromosome 21 (bTau4.0), and
  c) determining whether said animal carries the brachyspina mutation.

In a preferred aspect the deletion encompasses 3,329 base pairs spanning nucleotide positions 20537017 to 20540346 on bovine chromosome 21 (bTau4.0) in the bovine FANCI gene.
Equally preferred is:

A method for determining whether a bovine is affected by brachyspina (BS) or a carrier of brachyspina (BS) by analyzing its genomic RNA, the method comprising the steps of:
  a) obtaining a sample of material containing said genomic RNA from the bovine,
  b) extracting the RNA from said sample,
  c) genotyping said RNA for a deletion in the interval between nucleotide positions 20537017 to 20540346 on bovine chromosome 21 (bTau4.0); and
  d) determining whether said animal carries the brachyspina mutation.

Again, in a preferred aspect the deletion encompasses 3,329 base pairs spanning nucleotide positions 20537017 to 20540346 on bovine chromosome 21 (bTau4.0) in the bovine FANCI gene.

"RNA" as referred to herein encompasses all types of RNA. Techniques well known in the art can be used for the isolation of total RNA, mitochondrial RNA, or messenger RNA. The person skilled in the art can select a suitable extraction method without further ado depending on the nature of the sample to be tested.

If a sample containing RNA is to be used in accordance with the present invention as a template for an amplification reaction, it will be necessary to transcribe said RNA in cDNA before amplification can be carried out. Again, techniques for doing so are well known to the person skilled in the art. As an example the RNA may be purified with RNeasy™ Mini Kit (Qiagen). The RNA will then be reversely transcribed to cDNA using, e.g. the SuperScript™ Choice System (Invitrogen).

In another embodiment of the present invention a method is provided for determining whether a bovine is affected by or a carrier of brachyspina syndrome (BS) by analyzing its genomic DNA or RNA, the method comprising the steps of:
  a) extracting the DNA or RNA from a sample of biological material containing said genomic DNA or RNA obtained from the bovine,
  b) genotyping said DNA or RNA for a deletion in the interval between nucleotide positions 20537017 to 20540346 on bovine chromosome 21 (bTau4.0), further comprising genetic markers that are linked to the brachyspina locus; and
  c) determining whether said animal carries the brachyspina mutation.

In a further embodiment of the present invention a method is provided for determining whether a bovine is affected with the brachyspina syndrome or carrier of brachyspina by analyzing its DNA or RNA, the method comprising the steps of:
  a. obtaining a sample of material containing said genomic DNA or RNA from the bovine,
  b. extracting the DNA or RNA from said sample,
  c. genotyping said DNA or RNA for genetic markers that are linked to the brachyspina locus; and
  d. ascertaining whether said animal carries the brachyspina mutation by linkage analysis.

Thus, in a further preferred aspect of the present invention the genotyping step of the claimed method further utilises genetic markers that are linked to the brachyspina locus.

The term "brachyspina locus" as defined in the present invention means a polynucleotide sequence in the bovine FANCI gene on chromosome 21 which when mutated or deleted is causative for brachyspina or leading to a brachyspina carrier status. In a preferred embodiment, "brachyspina locus" is the region encompasses 3,329 base pairs spanning nucleotide positions 20537017 to 20540346 on bovine chromosome 21 (bTau4.0) in the bovine FANCI gene.

The term "genetic markers linked to the brachyspina locus" refers to DNA sequence variants such as microsatellite markers or Single Nucleotide Markers (SNPs) that are located on bovine chromosomes 21 at less than 50% genetic recombination units from the brachyspina locus and which can be used in accordance with the present invention. In the bovine, 50% genetic recombination units correspond to approximately 50 million base pairs. Preferred genetic marker molecules of the present invention are selected from the group consisting of SNP markers located within 1 million base pairs from the FANCI gene.

The term "ascertaining" or "determining" "whether said animal carries the brachyspina mutation by linkage analysis", or "ascertaining" or "determining" "whether said animal carries the brachyspina deletion by linkage analysis" refers to the determination of which allele at any of the genetic markers linked to the brachyspina locus is associated with the brachyspina mutation in a known carrier parent (which can be either the sire, the dam or both), and determining whether such linked marker allele is transmitted to the tested individual using standard linkage analysis procedures which are well known by those skilled in the art. Standard linkage analysis procedures are inter alia referred to in (7).

Further provided is a method for determining whether a bovine is affected by or a carrier of brachyspina syndrome (BS) by analyzing its genomic DNA or RNA, the method comprising the steps of:
a) extracting the DNA or RNA from a sample of biological material containing said genomic DNA or RNA obtained from the bovine,
b) genotyping said DNA or RNA for a deletion in the interval between nucleotide positions 20537017 to 20540346 on bovine chromosome 21 (bTau4.0), further comprising genetic markers that are in linkage disequilibrium to the brachyspina locus; and
c) determining whether said animal carries the brachyspina mutation comprising linkage analysis or association analysis.

Equally provided is a method is provided for determining whether a bovine is affected with the brachyspina syndrome or a carrier of brachyspina by analyzing its DNA or RNA, the method comprising the steps of:
a. obtaining a sample of material containing said genomic DNA or RNA from the bovine,
b. extracting the DNA or RNA from said sample,
c. genotyping said DNA or RNA for genetic markers that are in linkage disequilibrium with the brachyspina locus, and
d. ascertaining whether said animal carries the brachyspina mutation by association analysis or linkage analysis.

Thus, in a further preferred aspect of the present invention the determining step of the claimed method further comprises linkage analysis or association analysis.

The term "genetic markers that are in linkage disequilibrium with the brachyspina locus" refers to DNA sequence variants such as microsatellite markers or Single Nucleotide Markers (SNPs) that are in linkage disequilibrium with the brachypsina locus in cattle populations. Linkage disequilibrium, also referred to as gametic association or association, refers to the non-random assortment of alleles at distinct genetic loci in the general population. In the present case, these are DNA sequence variants for which one allele is more often associated with the brachyspina mutation in the general population than expected only by chance. In the bovine these include genetic markers, whether microsatellites or SNPs, that are located between nucleotide positions 20 million and 22.5 million on bovine chromosome 21 (bTau4.0).

The term "ascertaining whether said animal carries the brachyspina mutation by association analysis" or "ascertaining whether said animal carries the brachyspina deletion by association analysis" indicates that one will determine whether said animal is carrier of the brachyspina mutation from the analysis of its genotype at DNA sequence variants that are in linkage disequilibrium with the brachpsina mutation. The association analysis can be performed by extracting linkage disequilibrium information from DNA sequence variants considered individually ("single point analyses"), or by considering the DNA sequence variants jointly ("multipoint analyses" including "haplotype-based analyses"). The principles of association studies are known by those skilled in the art and are for instance described in (8).

Furthermore, the possibility to detect animals that are carriers of the brachyspina mutation can be utilized for marker assisted selection to enhance fertility. We have indeed demonstrated that carrier-status for brachyspina is strongly correlated with fertility, one of the most important economic traits in cattle. We demonstrate in this invention that the brachyspina mutation is present in ~7.5% of Holstein-Friesian animals, which is more common than might be expected from the apparently low incidence of the disease. Thus, brachyspina is a much more important issue in cattle than reflected by the incidence of calves born affected. Detecting brachyspina carriers can thus be used for marker assisted selection to enhance fertility.

As a result of this invention, it is now possible to detect carrier animals for brachyspina by means of simple genetic tests performed on a nucleic acid extracted from biological samples originating from said animals and use the information obtained by the methods of the present invention for marker assisted selection for increased fertility.

The term "marker assisted selection for increased fertility" in accordance with the present invention refers to the use of DNA sequence variant information, corresponding either to the direct detection of the brachyspina mutation, or its indirect detection by means of DNA sequence variants that are either linked or in linkage disequilibrium with the brachyspina locus, to identify animals that are carriers of brachyspina following the procedures described above, and thereby obtain information about their breeding value for phenotypes related to male or female fertility. It is noteworthy that a novel form of marker assisted selection has been recently introduced referred to as "genomic selection" (see for instance reference 9). Information about the presence or absence of the brachyspina mutation can be utilized if the genomic selection procedure were to be applied for traits related to both male and female fertility. Genomic selection for such traits would thus utilize information that is disclosed in the present invention.

Thus, in a further embodiment the present inventions provides for the use of the methods of the present to perform marker assisted selection or genomic selection for increased fertility in said bovine.

In accordance with the present invention a method for increasing fertility in a bovine or bovine population is provided comprising
a) obtaining a sample of material containing said genomic DNA from the bovine,
b) extracting the DNA from said sample,
c) genotyping said DNA for a deletion causing brachyspina as described herein; and
d) identifying a bovine that is a carrier for brachyspina.

Another aspect of the present invention focuses on a method for the detection of the above identified brachyspina mutation/deletion comprising amplifying by techniques well established in the art, e.g., and encompassed within the ambit of the present invention, polymerase chain reaction (PCR), the isolated DNA obtained from the bovine with specific primers for said mutation. As a non-limiting example, the nucleotide sequences as set forth in SEQ ID NOs: 5 and 6 can be applied as a as mutant PCR primer pair for the detection of brachyspina. In accordance with the present invention, the nucleotide sequences as provided in SEQ ID NOs: 3 and 4 can be used as a wild-type control PCR primer pair. Preferably, the genotyping step is carried out simultaneously to detect the mutant and the wild-type allele. It is contemplated to design further specific primers or primer pairs for the detection of brachyspina. Thus, primers are within the scope of the present invention which are directed to the specific sequences adjacent to or flanking the above defined mutation. Preferably, primers are included binding specifically to a region within 1 to 500 nucleotides, preferably 1 to 100 nucleotides or even more preferred 1 to 50 nucleotides surrounding the mutation as disclosed herein.

In a further embodiment of the present invention a method for the detection of the disclosed brachyspina mutation is provided comprising amplifying the isolated DNA obtained from the bovine, e.g. by PCR and further utilising specific probes directed to the brachyspina locus as referred to herein. As a non-limiting example, probes like 5'HEX-AGT CCC AGT GTG GCT AAG GAG TGA-3'IABkFQ (wild-type) (SEQ ID NO: 7) and 5'FAM-CCA TTC CAC/ZEN/ CTT TCT ATC CGT GTC CT-3'IABkFQ (mutant) (SEQ ID NO: 8) can be used in accordance with the present invention. Again, in a further embodiment of the present invention it is envisaged to design further specific probes directed to nucleotide sequences flanking the above defined mutation. Preferably, probes are included binding specifically to a region within 1 to 1000 nucleotides, preferably 1 to 500 nucleotides, more preferably 1 to 100 nucleotides or even more preferred 1 to 50 nucleotides surrounding the mutation as disclosed herein.

In a further aspect of the present invention the probe is labeled with a fluorophore. Fluorophores are well-known in the art. Preferably, applied in the methods and uses of the present invention are: 6-carboxyfluorescein (FAM), hexachlorofluorescein (HEX), or Fluorescein isothiocyanate (FITC). It is also envisaged by the present invention that the probe or probes applied in methods and uses provided herein further comprise a quencher. Even more preferred is an internal quencher, having a distance between the fluorophore and the quencher of 20 to 30 bases. Most preferred is a ZEN™ quencher which decreases the length to only around 9 bases.

DETAILED DESCRIPTION OF THE INVENTION

Autozygosity-mapping Positions the Brachyspina Locus in a 2.5 Mb BTA21 Interval.

Between January 2008 and December 2009, we obtained biological material from six Holstein-Friesian calves diagnosed with brachyspina. As the previously reported cases (f.i. 4), the six affected animals traced back, on sire and dam side, to Sweet Haven Tradition, a once popular artificial insemination (AI) Holstein-Friesian bull. Genomic DNA was extracted using standard procedures and genotyped using a previously described bovine 50K SNP array (3). Assuming that brachyspina is indeed inherited as a autosomal recessive defect and genetically homogeneous in Holstein-Friesian (as suggested from pedigree analysis), the six cases are predicted to be homozygous for a common haplotype encompassing the causative mutation. We performed autozygosity mapping using the ASSIST program (3) and 15 healthy Holstein-Friesian bulls as controls, and identified a single genome-wide significant peak (p<0.001) on chromosome 21 (BTA21). The shared haplotype spans 2.46 Mb (bTau4.0: 20,132,767-22,588,403) encompassing 56 annotated genes (FIG. 1).

Targeted and Genome-wide Resequencing Identifies the Causative 3.3 Kb Brachyspina Deletion in the FANCI Gene.

Several of the 56 genes in the interval are known to cause embryonic lethality when knocked out in the mouse. We amplified the corresponding open reading frames (ORF) from genomic DNA of cases and controls but did not find any obvious disruptive DNA sequence variant (DSV). We then performed targeted sequencing of the entire 2.46 Mb interval. A custom sequence capture array (Roche Nimblegen) was designed based on the bovine bTau4.0 build, and used to enrich the corresponding sequences from total genomic DNA of two affected individuals prior to paired-end sequencing (2×36 bp) on an Illumina GAIIx instrument. Resulting sequence traces were mapped to the bTau4.0 build using Mosaik (http://bioinformatics.bc.edu/marthlab). In the targeted region, the coverage of non-repetitive bases averaged 90.45 (range: 0-336) for the first sample, and 61.28 (range: 0-189) for the second, to be compared with 0.01 (range: 0-24) for the first and 0.01 (range: 0-104) for the second sample outside the targeted region. The proportion of targeted non-repetitive bases with coverage <10 was 0.12 for both samples. We used the GigaBayes software (Gabor T. Marth, Boston College, http://bioinformatics.bc.edu/marthlab) to identify DSV and detected 2,368 SNPs and 572 indels for a total of 2,940 DSVs. One thousand thirty two of these corresponded to DSV previously reported in breeds other than Holstein-Friesian, and were therefore eliminated as candidate causative mutations. Of the remaining 1,908 DSV only one was coding, causing a serine to glycine substitution in the L00516866 gene encoding a myosin light chain kinase-like protein. This DSV was not considered to be a credible candidate mutation underlying brachyspina.

We then generated mate-pair libraries from self-ligated 4.8 Kb (±0.35 Kb) fragments of one brachyspina case and three unrelated, healthy controls and generated <3.7 Gb of sequence on a Illumina GAIIx instrument for each animal. Resulting traces were mapped to the bTau4.0 build using the Burrows-Wheeler Aligner (BWA)(10), and alignments visualized with the Integrative Genomics Viewer (IGV)(11). Analysis of the reads mapping to the 2.46 Mb interval readily revealed a 3.3 Kb deletion removing exons 25-27 of the 37 composing the FANCI (Fanconi anemia complementation-group I) gene. The deletion was apparent from a cluster of 27 mate-pairs mapping ~8 Kb apart on the bTau4.0 build, and from the complete absence of reads mapping to the deleted segment for the brachyspina case, contrary to the three controls showing normal, uniform coverage in the region. Retrospective analysis of the sequence traces captured from affected individuals confirmed the abrupt coverage drop at the exact same location. We designed a primer pair spanning the presumed deletion, allowing productive amplification of a 409 by product from genomic DNA of affected and carrier animals but not of unrelated healthy controls from the same or other breeds. Sequencing this amplicon defined the deletion breakpoints, confirming the 3,329 bp deletion (FIG. 2A). Retrospective analysis of the sequence traces captured from affected individuals identified several reads bridging and confirming the breakpoint. Conversely, primer pairs designed within the deletion did not yield any amplification from DNA of affected individuals compared to healthy ones.

Assuming that the deletion of exons 25 to 27 results in the juxtaposition of exons 24 and 28 in the mRNA, the 3.3 Kb deletion is predicted to cause a frameshift at amino-acid position 877 substituting the 451 carboxyterminal amino-acids with a 26-residue long illegitimate peptide. Moreover, the ensuing stop codon in exon 28 is expected to cause nonsense mediated RNA decay (FIG. 2B).

With its homologue FANCD2, the FANCI protein forms the ID complex that localizes to damage-induced chromatin foci. FANCI is essential for DNA interstrand crosslink repair. Like FANCD2, FANCI is monoubiquitinated by the ubiquitin ligase FA core complex, and phosphorylated by the ATM/ATR kinase (f.i. 12). Missense, nonsense and splice-site variants in the FANCI gene underlie ~2% of cases of Fanconi anemia (FA) in human (12,13). FA patients exhibit heterogenous symptoms, including growth retardation, skeletal abnormalities, renal, cardiac, gastrointestinal and reproductive malformations (reminiscent of bovine brachyspina), as well as bone marrow failure, early onset of cancer and mortality at a young age.

Development of a Diagnostic Test Directly Interrogating the 3.3 Kb FANCI Deletion and Confirmation its Causality.

We developed a 5' exonuclease genotyping assay that simultaneously interrogates the mutant and wild-type allele. The assay uses 5'-TGT TAG CCC AGC AGA GGA-3' (SEQ ID NO: 3) and 5'-ATT CTG AAT CCA CTA GAT GTC-3' (SEQ ID NO: 4) as wild-type PCR primer pair combined with 5'-GCA CAC ACC TAT CTT ACG GTA C-3' (SEQ ID NO: 5) and 5'-GGG AGA AGA ACT GAA CAG ATG G-3' (SEQ ID NO: 6) as mutant PCR primer pair, and 5'HEX-AGT CCC AGT GTG GCT AAG GAG TGA-3'IABkFQ (wild-type) (SEQ ID NO: 7) and 5'FAM-CCA TTC CAC/ZEN/CTT TCT ATC CGT GTC CT-3'IABkFQ (mutant) (SEQ ID NO: 8) as probes (Integrated DNA Technologies, Leuven, Belgium). Allelic discrimination reactions were carried out on an ABI7900HT instrument (Applied Biosystems, Fosters City, Calif.) for 40 cycles in 2.5 µl volume with a final concentration of 250 nM for each probe, 500 nM for wild-type primers, 350 nM for mutant primers, Taqman Universal PCR Master Mix 1X (Applied Biosystems, Fosters City, Calif.) and 10 ng of genomic DNA. Typical results are illustrated in FIG. 3.

As expected, all available brachyspina cases were shown by these test to be homozygous for the deletion. The deletion proved to be absent in a sample of 131 sires healthy animals representing ten breeds other than Holstein. We then genotyped a random sample of 3,038 healthy Holstein-Friesian animals Carriers of the deletions accounted for 7.4% of the sample, while no animals were found to be homozygous. Assuming Hardy-Weinberg equilibrium, the absence of homozygous animals in a sample of 3,038 individuals has probability <5%. This strongly suggests that homozygosity for the mutation is not compatible with normal health, i.e. that the 3.3 Kb FANCI deletion is causal.

REFERENCES

Figure 1:
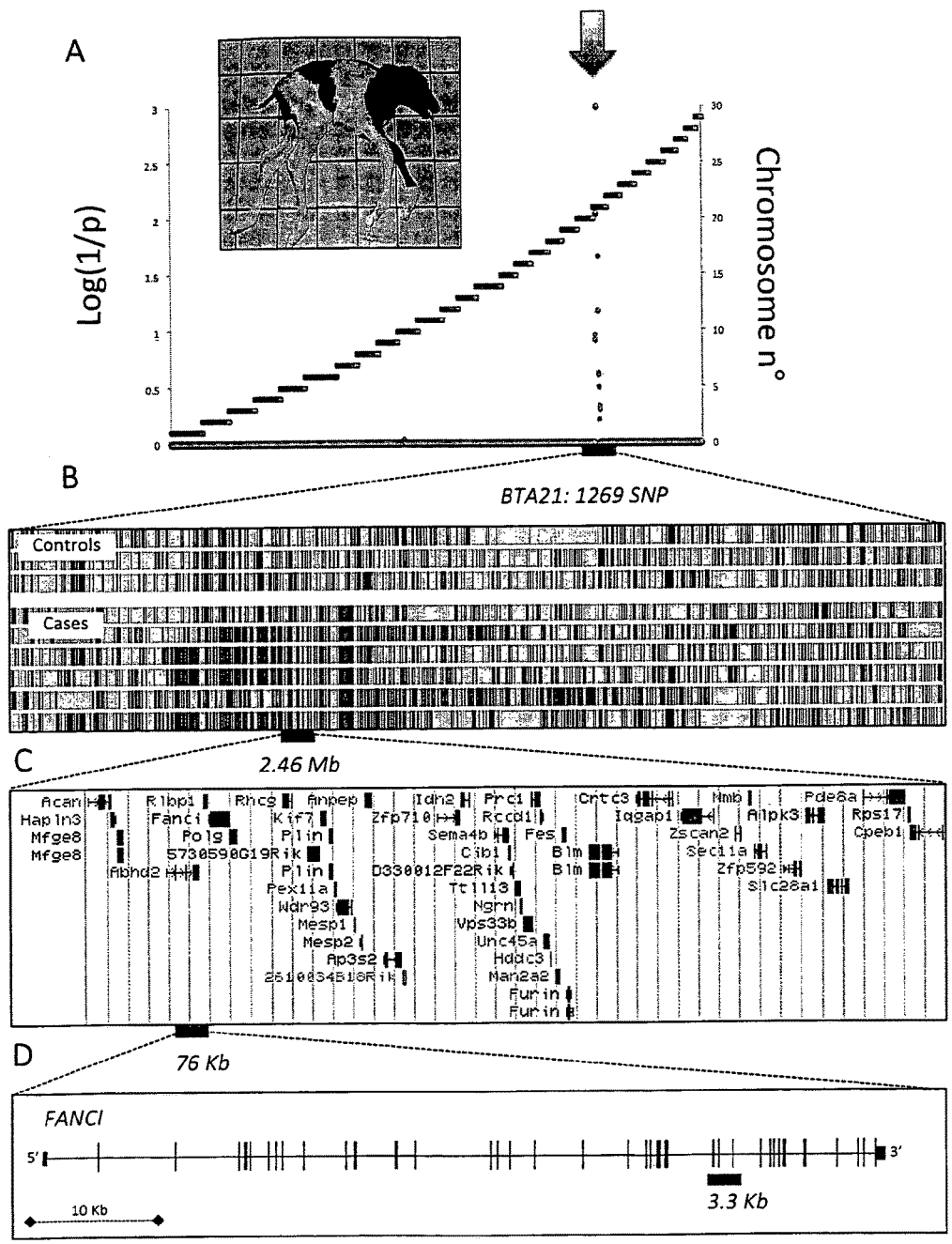
FIG. 1: Schematic representation of the brachyspina locus. Shown are: (A) the results of autozygosity mapping positioning the brachyspina locus on bovine chromosome 21; (B) the genotypes of six brachyspina cases and three healthy controls for 1,269 SNP markers on chromosome 21, showing the 2.46 Mb region of autozygosity in black & white; (C) the gene content of the 2.46 Mb region; (D) the structure of the FANCI gene with indication of the position of the 3.3 Kb brachyspina deletion.
Figure 2:
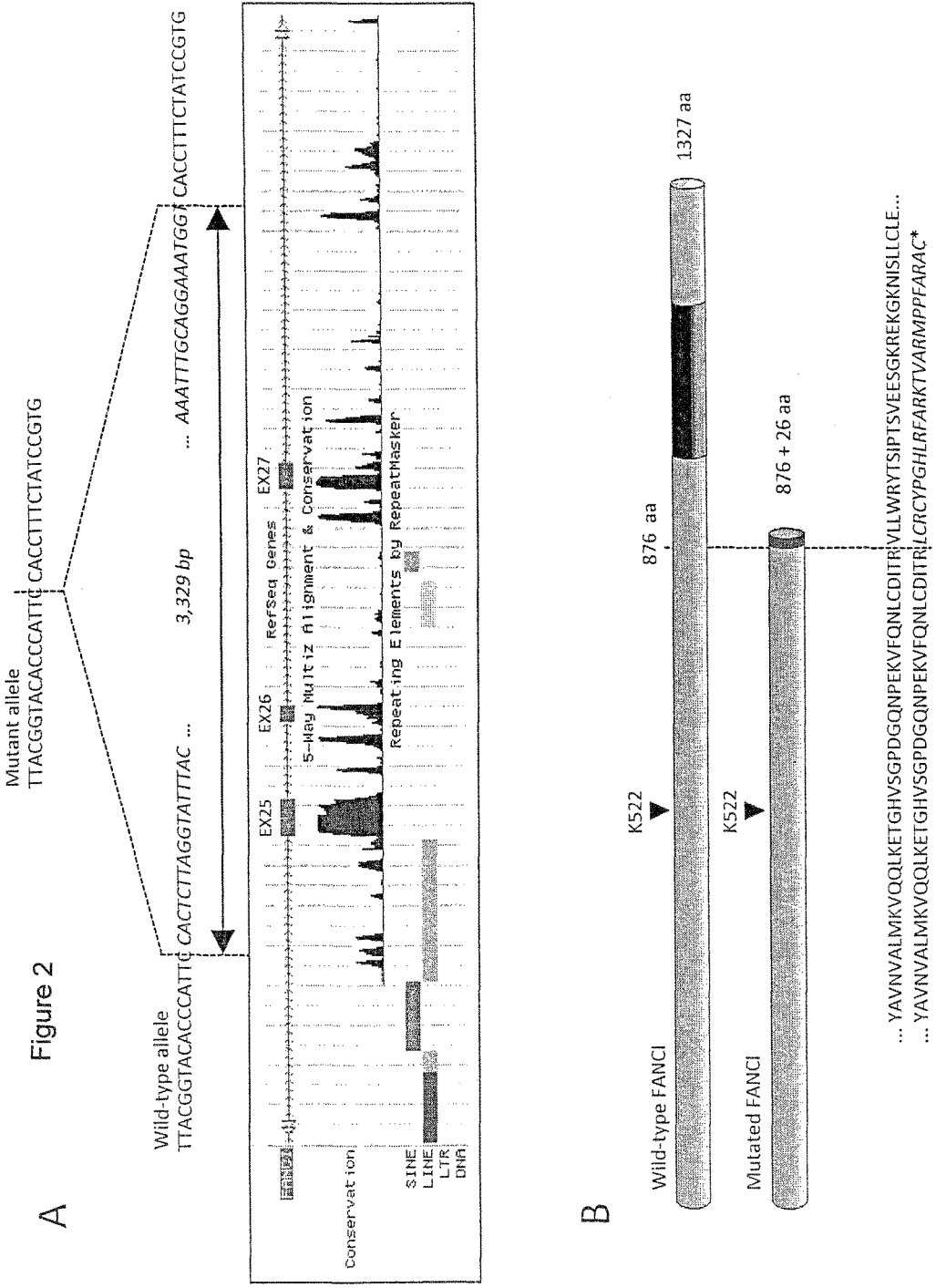
FIG. 2: Schematic representation of the brachyspina mutation. (A) Detailed view of the 3.3 Kb brachyspina deletion deleting exons 25, 26 and 27 of the bovine FANCI gene. The sequences flanking the deletion breakpoints are given (SEQ ID NOS 10-11, respectively, in order of appearance). The mutant allele is disclosed as SEQ ID NO: 9. (B) Predicted effect of the 3.3 Kb brachyspina deletion on the structure of the bovine FANCI protein (SEQ ID NOS 12-13, respectively, in order of appearance).
Figure 3:
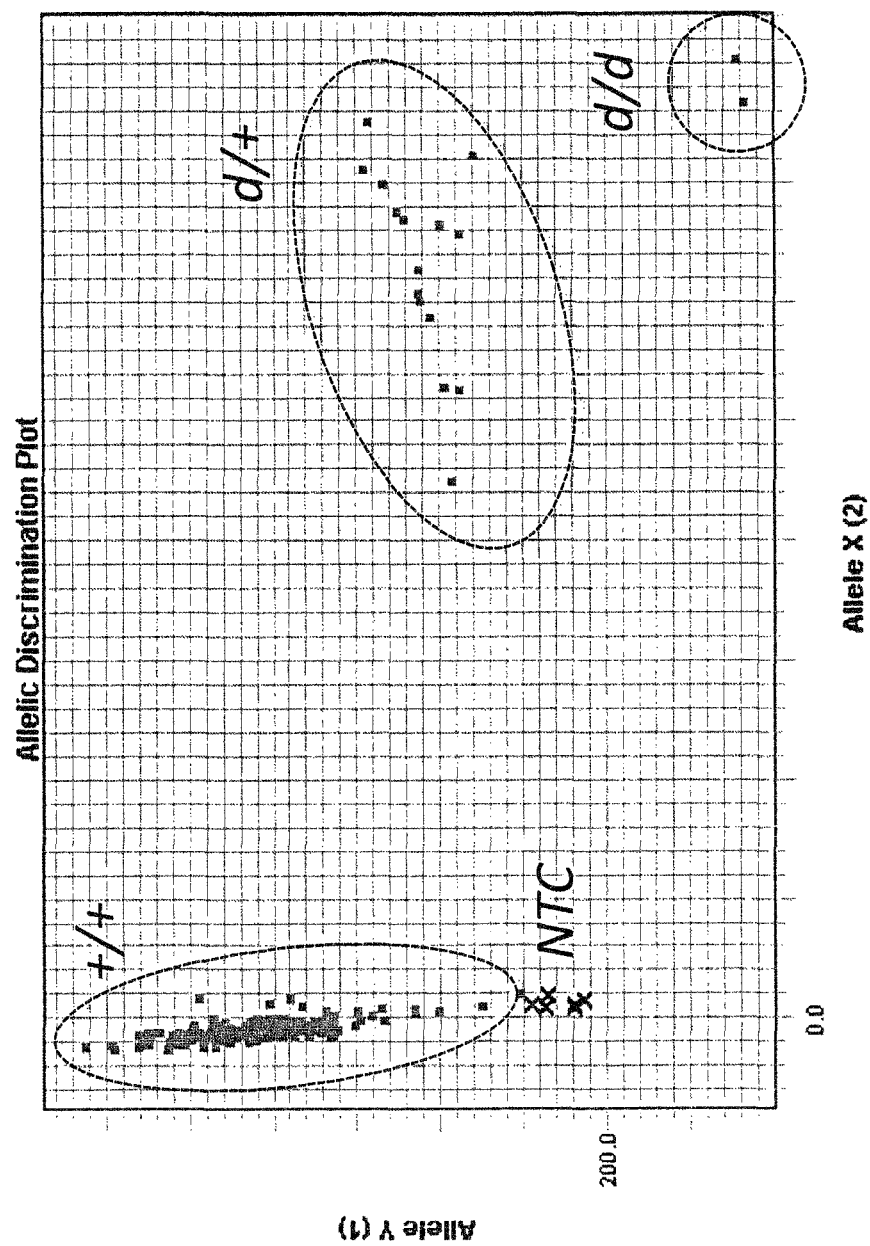
FIG. 3: Example of results obtained with the brachyspina 5' exonuclease test. Each animal is represented by a dot and the three clusters correspond to +/+, +/d, and d/d animals respectively; non template controls (NTC) are visualized as x.

1. Shuster D E, Kehrli M E Jr, Ackermann M R, Gilbert R O. (1992) Identification and prevalence of a genetic defect that causes leukocyte adhesion deficiency in Holstein cattle. *Proc Natl Acad Sci USA*. 89:9225-9229.
2. Thomsen B, Horn P, Panitz F, Bendixen E, Petersen A H, Holm L E, Nielsen V H, Agerholm J S, Arnbjerg J, Bendixen C. (2006) A missense mutation in the bovine SLC35A3 gene, encoding a UDP-N-acetylglucosamine transporter, causes complex vertebral malformation. *Genome Res*. 16:97-105. Epub 2005 Dec. 12.
3. Charlier C, Coppieters W, Rollin F, Desmecht D, Agerholm J S, Cambisano N, Carta E, Dardano S, Dive M, Fasquelle C, Frennet J C, Hanset R, Hubin X, Jorgensen C, Karim L, Kent M, Harvey K, Pearce B R, Simon P, Tama N, Nie H, Vandeputte S, Lien S, Longeri M, Fredholm M, Harvey R J, Georges M. (2008) Highly effective SNP-based association mapping and management of recessive defects in livestock. *Nat Genet*. 40:449-54. Epub 2008 Mar. 16.
4. Agerholm J. S. and Peperkamp K. (2007) Familial occurrence of Danish and Dutch cases of the bovine brachyspina syndrome. BMC Vet Res. 3:8.
5. Charlier C, Agerholm J S, Coppieters W, Georges M, Fredholm M. (2010). A genetic test for brachyspina and fertility in cattle. WO/2010/012690
6. Syvanen, A. C. (2001) Accessing genetic variation: genotyping single nucleotide polymorphisms. *Nature Reviews Genetics* 2: 930-942.
7. Ott J. (1999). Analysis of Human Genetic Linkage. Third edition. Johns Hopkings University Press.
8. Georges M (2007) Mapping, fine mapping, and molecular dissection of quantitative trait Loci in domestic animals. (*Annu Rev Genomics Hum Genet*. 8:131-162.
9. Meuwissen T H, Hayes B J, Goddard M E. (2001) Prediction of total genetic value using genome-wide dense marker maps. *Genetics*. 2001 April; 157(4): 1819-29.
10. Li H., Durbin R. (2009) Fast and accurate short read alignment with Burrows-Wheeler Transform. Bioinformatics, 25:1754-60.
11. Robinson J. T., Thorvaldsdottir H., Winckler W., Guttman M., Lander E. S., Getz G., Mesirov J. P. (2011) Integrative Genomics Viewer. Nature Biotechnology 29: 24-26.
12. Smogorzewska, A., Matsuoka, S., Vinciguerra, P., McDonald, E. R., III, Hurov, K. E., Luo, J., Ballif, B. A., Gygi, S. P., Hofmann, K., D'Andrea, A. D., Elledge, S. J. (2007) Identification of the FANCI protein, a monoubiquitinated FANCD2 paralog required for DNA repair. Cell 129: 289-301.
13. Dorsman, J. C., Levitus, M., Rockx, D., Rooimans, M. A., Oostra, A. B., Haitjema, A., Bakker, S. T., Steltenpool, J., Schuler, D., Mohan, S., Schindler, D., Arwert, F., Pals, G., Mathew, C. G., Waisfisz, Q., de Winter, J. P., Joenje, H. (2007) Identification of the Fanconi anemia complementation group I gene, FANCI. Cell. Oncol. 29: 211-218.

The invention claimed is:

1. A method for detecting the presence of a mutation in a bovine comprising the steps of:
   a) obtaining a biological sample from a bovine,
   b) extracting DNA or RNA comprising a FANCI gene or transcript from the biological sample,
   c) genotyping the DNA or RNA from the biological sample; and
   d) detecting the presence of a deletion mutation in the FANCI gene or transcript, wherein the FANCI gene or transcript comprises SEQ ID NO: 9 as a result of the deletion mutation.

2. The method of claim 1, wherein RNA is extracted from the sample and reverse transcribed to cDNA.

3. The method of claim 1, wherein the biological sample is selected from the group consisting of blood, sperm, hair roots, milk, body fluids, and tissue.

4. The method of claim 1, wherein the bovine is selected from the group consisting of a Holstein, a Friesian, a Holstein-Friesian Cross breed, a British Friesian, and a Dutch Friesian.

5. The method of claim 1, wherein genotyping the DNA or RNA from the biological sample comprises amplifying the DNA or RNA from the biological sample with specific primers comprising the nucleotide sequence of SEQ ID NOs: 5 and 6.

6. The method of claim 5, wherein amplifying the DNA or RNA from the biological sample further comprises using primers individually having the nucleotide sequence of SEQ ID NOs: 3 or 4 as a control.

7. The method of claim 5, wherein amplifying the DNA or RNA from the biological sample further comprises labelling a product of the amplification with a probe corresponding to the FANCI gene or transcript resulting from the deletion mutation.

8. The method of claim 7, wherein the probe comprises a fluorophore.

9. The method of claim 8, wherein the fluorophore is 6-carboxyfluorescein (FAM), hexachlorofluorescein (HEX), or Fluorescein isothiocyanate (FITC).

10. The method of claim 7, wherein the probe comprises comprises a quencher.

11. The method of claim 1, wherein genotyping the DNA or RNA from the biological sample comprises a detection method selected from the group consisting of allele specific hybridization, 3'exonuclease assay, fluorescent dye and quenching agent-based PCR assay, use of allele-specific restriction enzymes, direct sequencing, oligonucleotide ligation assay, pyrosequencing, invader assay, mini sequencing, DHPLC-based techniques, single strand conformational polymorphism, allele-specific PCR, denaturing gradient gel electrophoresis, temperature gradient gel electrophoresis, chemical mismatch cleavage, heteroduplex analysis based system, techniques based on mass spectroscopy, invasive cleavage assay, polymorphism ratio sequencing, microarray, rolling circle extension assay, HPLC-based techniques, extension based assays, ARMS, ALEX, SBCE, molecular beacon assay, invader, ligase chain reaction assay, 5'-nuclease assay-based techniques, hybridization capillary array electrophoresis, protein truncation assay, immunoassays, and solid phase hybridization.

12. The method of claim 7, wherein the probe comprises SEQ ID NO: 8.

13. The method of claim 6, wherein amplifying the DNA or RNA from the biological sample further comprises labelling a product of the amplification with a probe corresponding to the wild-type FANCI gene or transcript.

14. The method of claim 13, wherein the probe comprises SEQ ID NO: 7.

15. The method of claim 1, wherein the FANCI gene or transcript comprises SEQ ID NO: 2 as a result of the deletion mutation.

16. The method of claim 1, wherein the deletion mutation comprises a deletion of 3,329 base pairs spanning nucleotide positions 20537017 to 20540346 on bovine chromosome 21 (bTau4.0).

* * * * *